United States Patent [19]
Goshorn et al.

[11] Patent Number: 5,495,337
[45] Date of Patent: Feb. 27, 1996

[54] METHOD OF VISUALIZING MINUTE PARTICLES

[75] Inventors: Lawrence A. Goshorn, Rancho Santa Fe; Thomas O. Trozzi, Escondido; George T. Ayoub, Oceanside; Nicholas A. Newberg, San Marcos, all of Calif.

[73] Assignee: Machine Vision Products, Inc., Carlsbad, Calif.

[21] Appl. No.: 178,918

[22] Filed: Jan. 7, 1994

Related U.S. Application Data

[63] Continuation of Ser. No. 788,558, Nov. 6, 1991, abandoned.
[51] Int. Cl.⁶ .................................................. G01B 11/24
[52] U.S. Cl. ........................... 356/376; 356/379; 356/237; 348/126
[58] Field of Search ....................... 356/376, 375, 356/380, 379, 394, 237; 250/561, 562; 348/126

[56] References Cited

U.S. PATENT DOCUMENTS

| 4,105,925 | 8/1978 | Rossol et al. | 356/379 |
| 4,573,073 | 2/1986 | Corby, Jr. | 356/376 |
| 4,627,734 | 12/1986 | Rioux | 356/376 |
| 4,705,401 | 11/1987 | Addleman et al. | 356/376 |
| 4,767,212 | 8/1988 | Kitahashi et al. | 356/379 |
| 4,798,964 | 1/1989 | Schmalfuss et al. | 356/376 |
| 5,102,224 | 4/1992 | Uesugi et al. | 356/376 |

Primary Examiner—Hoa Q. Pham
Attorney, Agent, or Firm—Bernard L. Kleinke

[57] ABSTRACT

The visualization method includes generating a relatively wide beam of light directed onto an object to be inspected and determining the center of intensity of the wide beam of light reflected from the object for facilitating geometric dimensional calculations of a large number of such objects, such as solder deposits on the surface of a printed circuit board, in a very short period of time and in a very accurate manner.

15 Claims, 20 Drawing Sheets

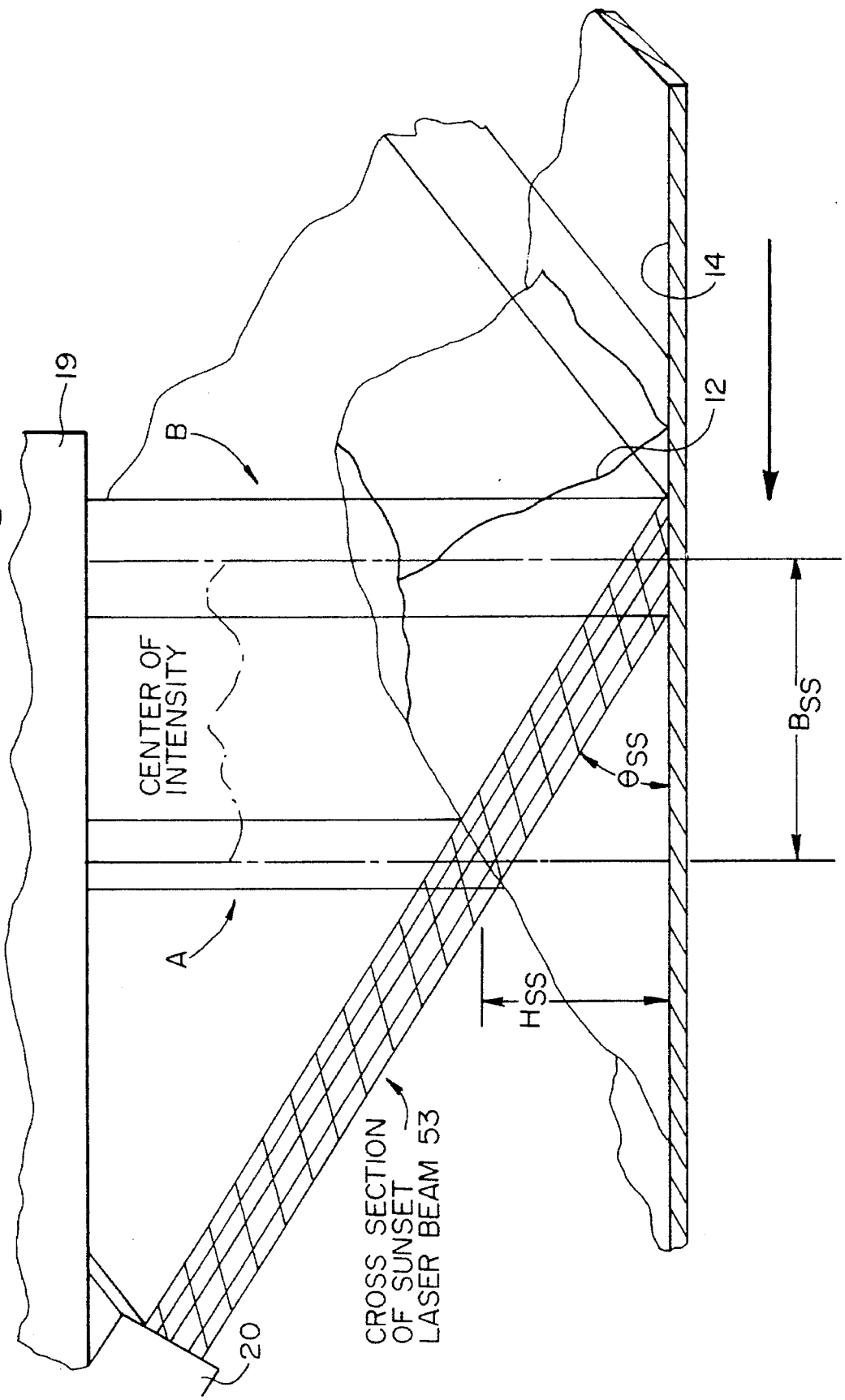

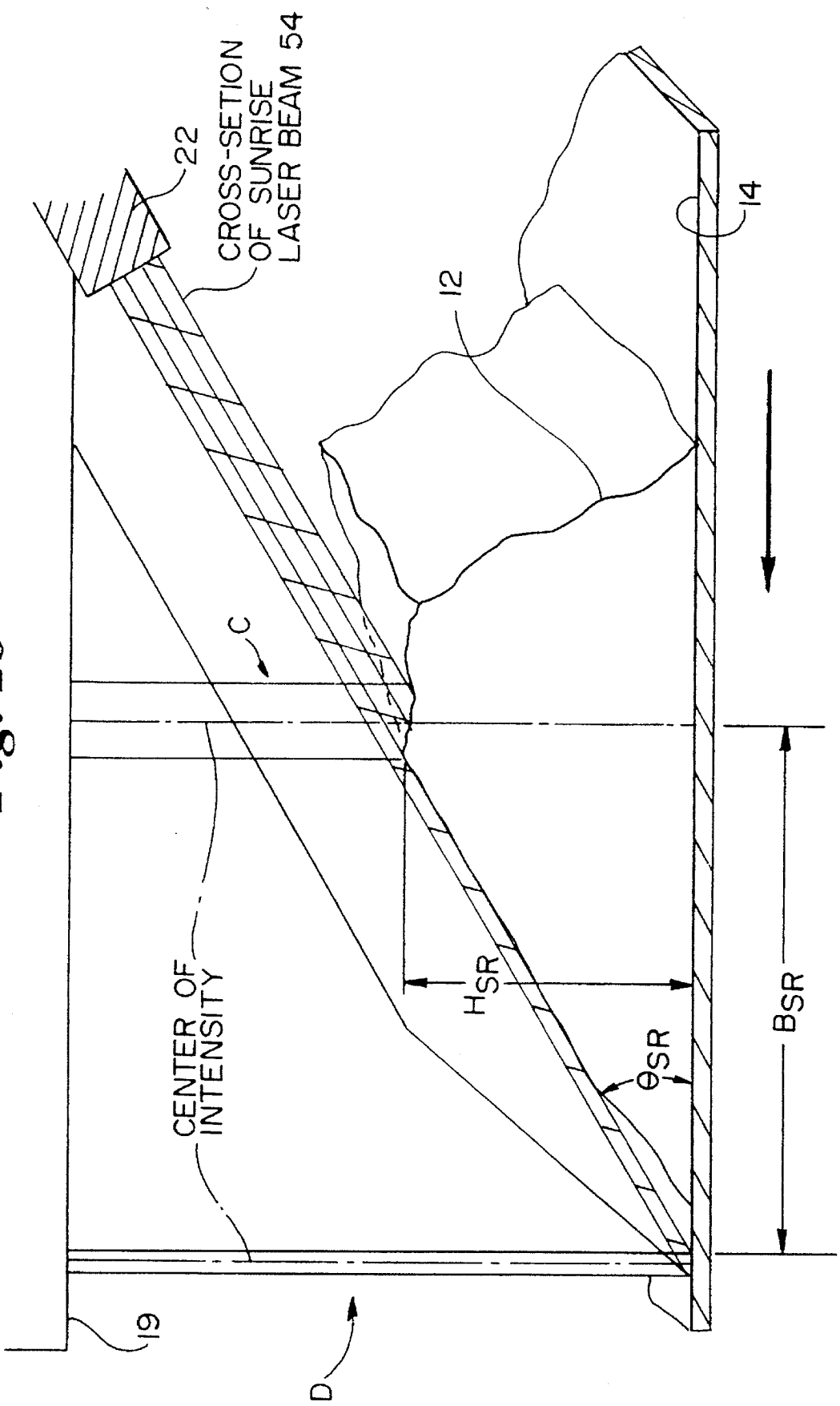

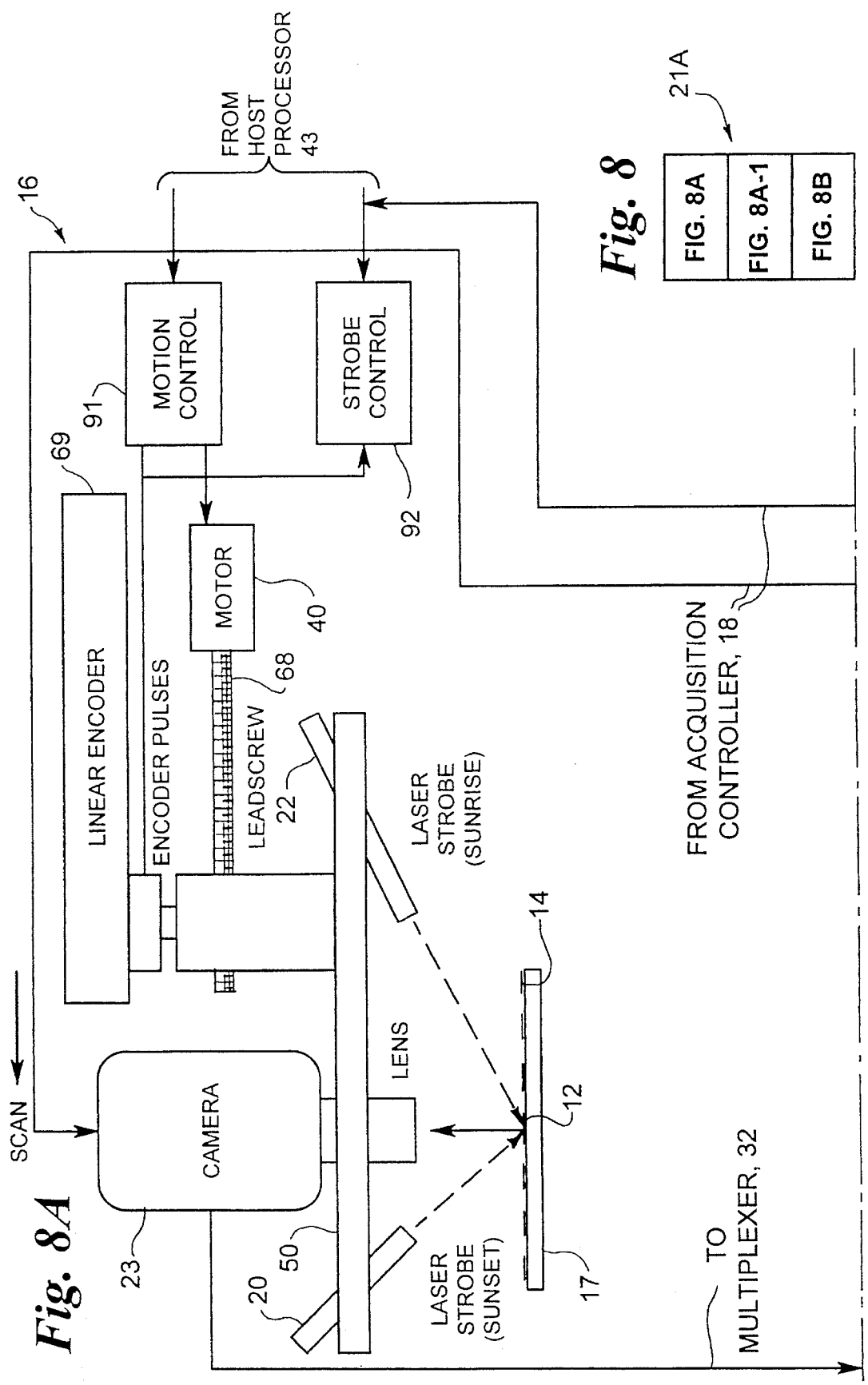

Fig. 9
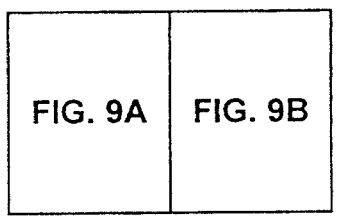
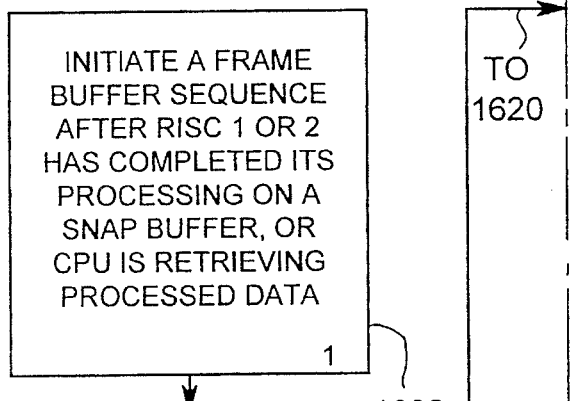
Fig. 9A
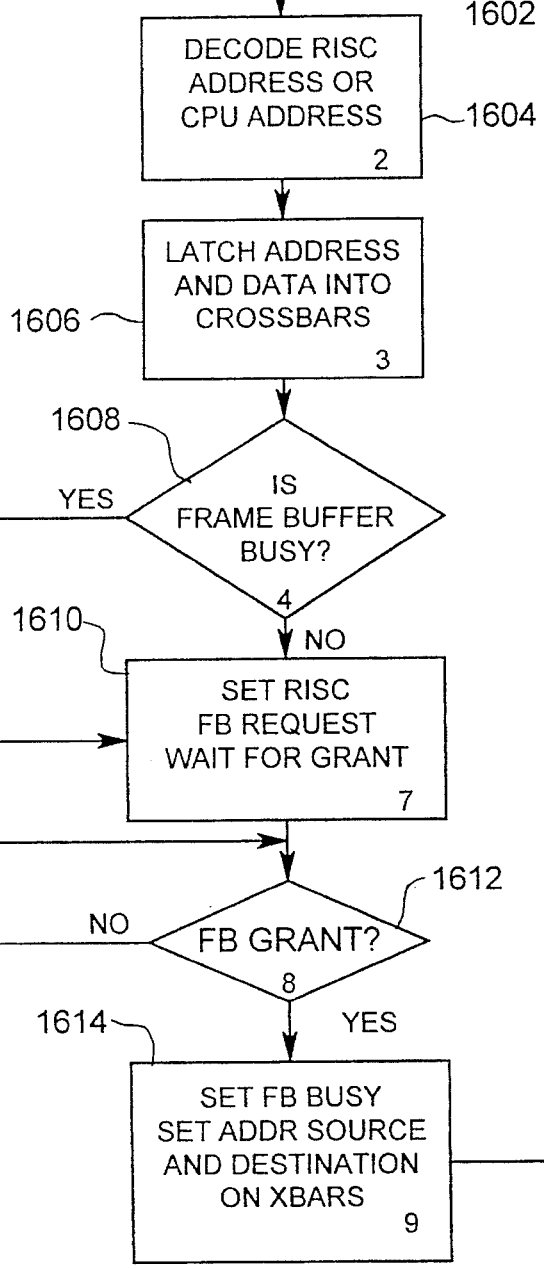

METHOD OF VISUALIZING MINUTE PARTICLES

RELATED APPLICATIONS

This application is a continuation of U.S. patent application Ser. No. 07/788,558 filed Nov. 6, 1991, now abandoned.

TECHNICAL FIELD

The present invention relates in general to a visualization method and more particularly, the present invention relates to a visualization method for inspecting small objects, such as solder paste deposits positioned on a printed circuit board in an extremely fast and accurate manner.

BACKGROUND ART

In modern printed circuit board technology, such as in surface mount technology, small electronic circuit components are attached electrically by soldering techniques to a printed circuit board. If the components are not properly mounted on the board, the board can then become rejected during the manufacturing process. Such a situation is very expensive, and of course, undesirable.

The rejects frequently occur as a result of the improper placement of solder paste deposits on the printed circuit board prior to the mounting of components thereon. In this regard, a metal screen process is employed to apply the solder paste to the board. In so doing, a larger or a smaller volume of solder paste may be applied inadvertently. If too little solder paste is applied, the electrical components do not have the proper electrical and mechanical bonding characteristics. If an excessive amount of solder paste is deposited, and heat applied, the solder paste flows beyond the electrical component lead and can form bridging or undesirable and unwanted short circuits, thereby leading to a rejection of the board.

Additionally, should the solder paste deposit be applied in an improper position on the surface of the board, rejections can also result. Thus, both the volume of the solder paste deposit and the positioning thereof are usually critical. Accurate solder paste positioning is especially important where very small electrical components having fine pitch leads, such as surface mount devices, are employed.

Therefore, it would be highly desirable to somehow be able to inspect both the volume and positioning of each individual solder paste pad on a printed circuit board. However, such an inspection must be made very quickly in a matter of seconds, in order not to slow down the throughput of the manufacturing process. For example, a three inch by five inch printed circuit board may have up to 600 small solder paste pads or deposits thereon, which all must be inspected for both volume and positioning in less than two seconds.

One attempted solution to verify the accuracy of solder paste deposit positions was tried, wherein a laser produces a small spot of high intensity light which was projected toward the surface of a printed circuit board. The intensity of the reflected spot was visualized by a camera to generate a signal in an attempt to verify the approximate height of the illuminated area relative to an expected height. However, as the amount of light reflected was extremely small, only a few such discrete inspections could be made per board within a reasonable amount of time, to determine whether solder paste deposits on the board were positioned within expected tolerance limits.

While such a system may permit a random sampling of a few solder paste deposits, it is unable to determine with accuracy the actual volume of the solder paste deposits within. Moreover, such an arrangement is only able to inspect a relatively few number of pads within a matter of a short time, such as two to three seconds.

DISCLOSURE OF INVENTION

Therefore, it is the principal object of the present invention to provide a new and improved visualizing system and a method of using it, to inspect small objects, such as solder paste pads on a printed circuit board, in a very rapid and accurate manner.

Another object of the present invention is to provide such a new and improved visualization system and method, whereby a large number of three dimensional, minute sized objects can be inspected for determining their volume and position in an extremely rapid manner.

Briefly, the above and further objects of the present invention are realized by providing a new and improved visualization system and method, wherein a large number of small objects can be inspected in a very rapid and accurate manner. The visualization system includes an arrangement for generating a relatively wide beam of light directed onto an object to be inspected. The arrangement determines the center of intensity of the wide beam of light reflected from the object for facilitating geometric dimensional calculations of a large number of such objects, such as solder paste deposits on the surface of a printed circuit board, in a very short period of time and in a very accurate manner.

By employing a wide beam of incident light to illuminate objects, a large number of image samples of the surface elevations of the objects may be taken in a very rapid period of time in a highly accurate manner. More particularly, the amount of light in the reflected beam is sufficiently large that only a small period of integration time is required by system cameras.

The image processing system of the present invention enables high resolution sampling of the objects, even with the utilization of a wide beam of incident light. In this regard, the processing system finds the center of intensity of the reflected light by a weighted averaging method and effectively narrows the beam to a single pixel address, thus, achieving the effect of a high resolution sampling grid.

Another advantage evidenced by the present system is throughput. In this regard, the center of intensity determination is accomplished as a pre-processing step in a pipeline mode. Thus, application processing for determining geometric dimension calculations of the objects, is a subsequent function in the pipeline. Such calculations can include the volume and relative position of the object. By high rate image acquisition and parallel preprocessing, a large number of objects may be fully inspected in a highly accurate manner, in a very short period of time. Thus, the present invention achieves a high throughput rate of inspection of a large number of small objects with relatively accurate measurements.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIGS. 2A–B are diagrammatic side elevational views of the system of FIG. 1 illustrating an object on the surface of a substrate, such as a printed circuit board of FIG. 1, in accordance with the principles of the present invention;

BEST MODE FOR CARRYING OUT THE INVENTION

The detailed description of the present invention is organized in accordance with the following outline:
A. GENERAL SYSTEM DESCRIPTION
B. GENERAL SYSTEM OPERATION
C. DETAILED SYSTEM DESCRIPTION
D. DETAILED SYSTEM OPERATION
E. OPTICAL SYSTEM
F. LASER BEAM PROJECTORS
G. PROCESSOR FIRMWARE

A. GENERAL SYSTEM DESCRIPTION

Figure 1:
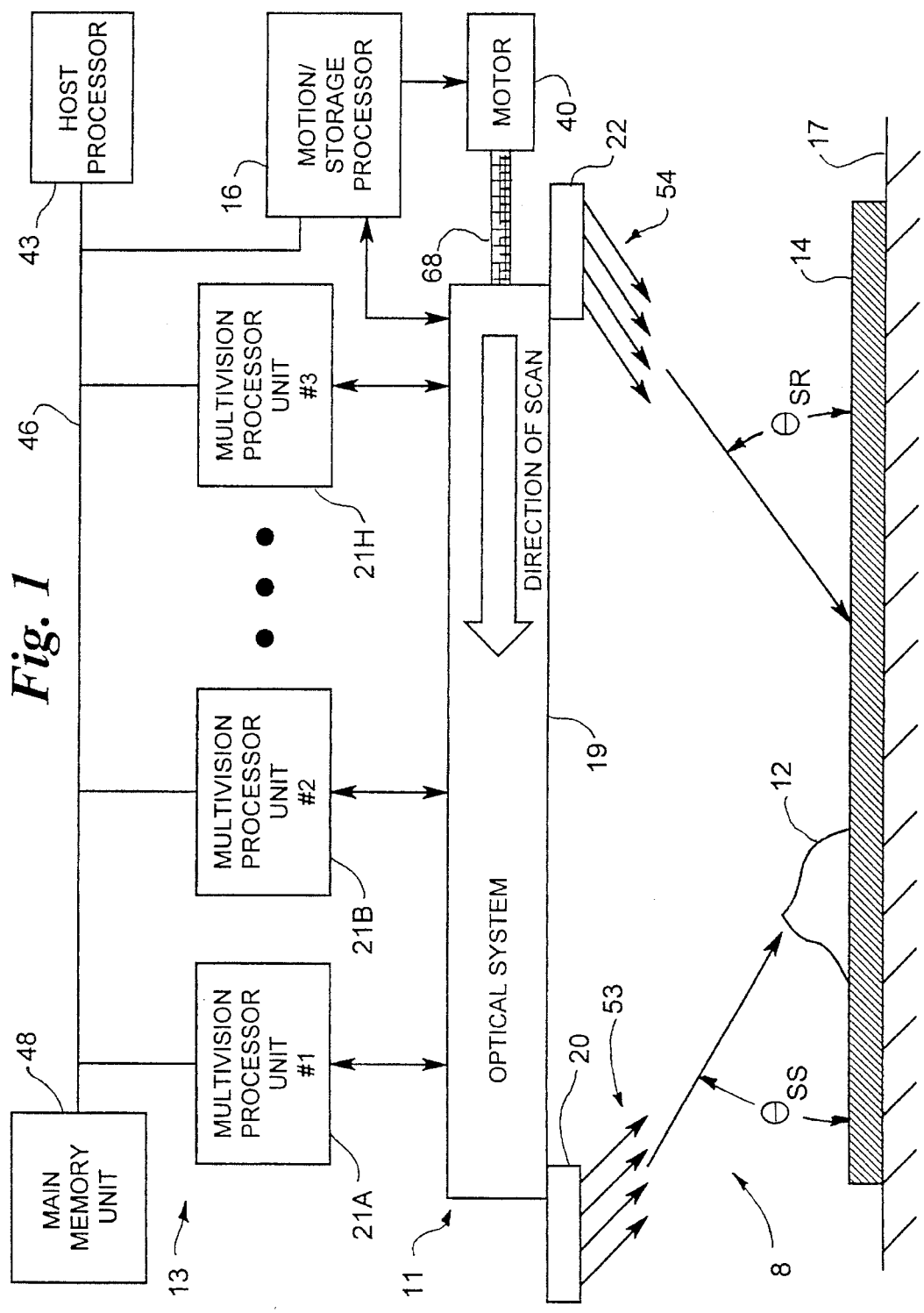
FIG. 1 is a simplified system block diagram of a visualization system which is constructed in accordance to the present invention.

Referring now to the drawings and more particularly to FIG. 1 thereof, there is shown a visualization system 8, which is constructed in accordance to the present invention. The visualization system 8 enables the positional location and geometric dimension of a minute particle, such as a solder paste deposit 12, on the substrate of a printed circuit board 14 to be determined and accurately measured. In this regard, the visualization system 8 forms part of a process feedback loop (not shown) in the manufacturing of surface mount circuit boards, and yields reliable information for controlling the manufacturing process. More particularly, the visualization system 8 provides highly accurate information not only on the volume, height, pad coverage and x-y translation of paste deposits, but it also determines the three-dimensional geometric shape of such deposits so that gathered visual information may be used to select and control the proper parameters of the manufacturing process.

While the system 8 is shown and described to be used in connection with the visualization of solder deposits, it will become apparent to those skilled in the art that the system 8 may also be used for visualizing quickly and accurately other types and kinds of objects as well.

As best seen in FIG. 1, the visualization system 8 generally comprises a visualization station 11 for visualizing three dimensional objects, such as the solder paste deposit generally indicated at 12, and an image processing system generally indicates at 13, for gathering and quantifying the visualization information developed via the visualization station 11. In this regard, the image processing system 13 determines the geometric dimensions of the visualized three-dimensional objects disposed on the top surface of the printed circuit board 14.

The visualization station 11 generally includes a pair of respective sunset and sunrise laser beam projector assemblies 20 and 22 for producing a pair of wide laser beams 53 and 54 respectively (FIGS. 1, 2A and 2B) which are projected angularly toward the top surface of the printed circuit board 14 at alternating times. Each such beam when so projected, extends transversely across substantially the entire width of the printed circuit board 14.

The visualization station 11 and the substrate moves horizontally relative to one another, in a spaced apart manner above the substrate in a single pass thereover.

The projectors 20 and 22 are disposed opposite one another for illuminating fully a given area of the substrate 14 and any solder paste deposits within the illuminated area, such as the deposit 12. The projectors 20 and 22 are mounted to a projector/camera micro-positioning stage or platform 50 (FIG. 8A) and are inclined downwardly at angles $\theta_{SR}$ and $\theta_{SS}$ respectively relative to the horizontal plane of a scanning table 17. As will be explained hereinafter in greater detail, the projector 20 and 22 are so mounted to effect a triangulation technique in which the position and intensity of each laser beam image projected on the substrate 14 is monitored or visualized to produce height and area measurements for scanned deposits.

For the purpose of visualizing the beam image reflected from the substrate 14, the visualization station 11 also includes an optical arrangement or system indicated generally at 19, having a bank of charged coupled cameras 23–30 (FIG. 3) and an image multiplexer unit 32 (FIG. 8). The camera 23–30 are mounted to the top of the platform 50 by a mounting plate 94 (FIG. 4), and are mounted orthogonal to the surface of the substrate 14. The cameras 23–30 are connected electrically to the multiplexer unit 32. In this regard, the multiplexer 32 produces a group of pixel image analog voltages which are indicative of the intensity of a group of image segments of a reflected beam image, such as a image indicated generally at 31 (FIG. 3), monitored by the cameras 23–30 respectively. In this regard, each camera monitors a given segment of the beam 31. Although in the preferred embodiment of the present invention only 8 camera are illustrated, it will be understood by those skilled in the art, that depending upon accuracy requirements and the size of the printed circuit board being visualized, a larger number of cameras, such as up to 32 cameras, could be employed in the optical system 19.

The visualization station 11, also includes a motion/strobe processor 16 for controlling the strobing of the laser projectors 20, 22 and the operation of a servo motor 40 to move the platform 50 relative to the scanning table 17. In this regard, as best seen in FIG. 1, as the optical system 19 and laser projectors 20, 22 are moved via the motor 40, the combined field of view of cameras 23–30 observes the entire surface area of the printed circuit board 14.

The image processing system 13, generally includes a host processor 43 for controlling the overall operation of the visualization station 11 and a group of multivision processor unit 21A–H for processing the image segments observed by cameras 23–30 respectively. In this regard, the multivision processor unit 21A–H operate in parallel under the control of the host processor 43 to produce a group of compressed height information signals which are processed to generate geometrical data for each solder paste deposit observed on the printed circuit board 14. As each of the multivision processor unit is 21A–H are substantially identical, only image acquisition unit 21A will be described hereinafter in greater detail.

For the purpose of enabling the host processor 43 to communicate with each of the multivision processor unit 21A–H, as well as the motion/strobe processor 16, the image processing system 13 also includes a shared memory buss 46 and a 4 Mbyte memory unit 48 (FIG. 88) for storage of information to facilitate the calculations of the volume and area geometric dimensions of the three-dimensional objects observed on the surface of the printed circuit board 14.

B. GENERAL SYSTEM OPERATION

Considering now the operation of system 8, with reference to FIGS. 2A and 2B, when a printed circuit board, such as the printed circuit board 14, is to be visualized, the host processor 43 via the motor 40, causes the cameras 23–30 and the laser beam projectors 20, 22 to be moved one micro-step at a time as a unit, above and across or along the entire longitudinal surface of the printed circuit board 14 in about two to three seconds. During this travel time interval, the laser beam projectors 20 and 22 are pulsed or strobed alternately ON and OFF allowing the cameras 23–30 to record a large number of reflected beam images.

When projector 20 is pulsed, a wide "sunset" laser beam or line 53 is projected toward the surface of the printed circuit board 14 at an angle $\theta_{SS}$. When the beam 53 strikes the surface of the printed circuit board 14, the beam 53 extends across substantially the entire traverse dimension of the board 14 illuminating any objects on its surface, such as the deposit 12. Because each of the objects on the surface of the board 14 are three-dimensional, they cause the image of the projected beam non-continuous along certain portions of the board 14. Stated otherwise, the position of the reflected beam varies across the transverse dimension of the board 14 and the deposit 12.

Referring now to FIG. 2A, when the beam 53 strikes the object 12 it produces a reflected beam A which is observed by one or more of the cameras in the optical system 19. Part of beam 53 also strikes the surface of the printed circuit board 14 to produce another reflected beam B. Under prior known systems, a binary process of the images A and B would result in the height of the object being determined relative to the geometric center of these reflected beams. The present system does not use this technique. Instead, the center of intensity of each of the beams A and B is calculated using a gray scale technique. In this regard, by determining a base measurement $B_{SS}$ of reflected images A and B relative to their calculated center of intensity values, a far more accurate determination of the height $H_{SS}$ of the object is determined.

Referring now to FIG. 2B, when the projector 22 is strobed, a wide "sunrise" laser beam 54 is projected across the surface of the printed circuit board 14. In this regard, the object 12 blocks or obscures part of the beam 54 from being reflected when it strikes the surface of the board 14. Because of such shadows, the beams 53, 54 illuminate the front and back sides respectively of the object 12. A reflected beam C is observed when the beam 54 strikes the object 12 and a reflected beam D is observed when beam 54 strikes the surface of the board 14. The center of intensity of each of the reflected beams C and D is determined and the distance between these centers is a base measurement $B_{SR}$.

Figure 16:
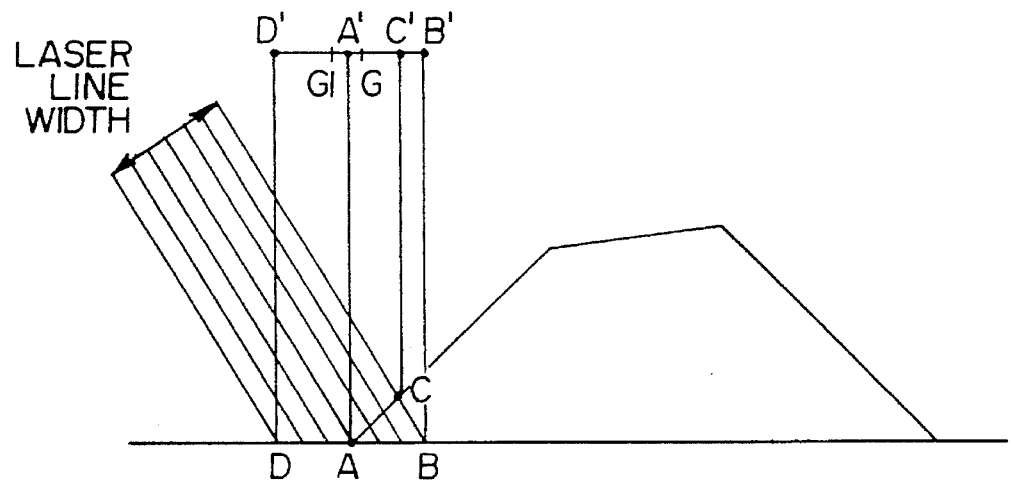
FIG. 16 is another diagrammatic side elevational view of the system of FIG. 1 illustrating an objection the surface of a substrate, such as a printed circuit board 14 of FIG. 1.
Figure 17A:
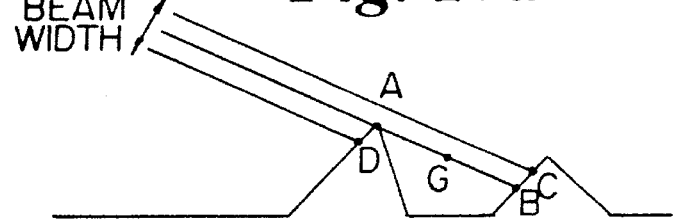
FIG. 17 is another diagrammatic side view of the system of FIG. 1 illustrating objects on the surface of a substrate, such as a printed circuit board 14 of FIG. 1.
Figure 17B:
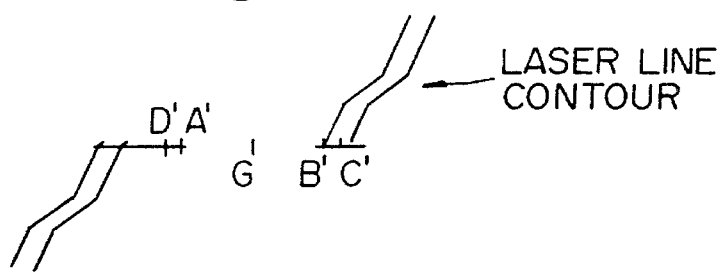

To further clarify the method of calculation the height of the object 12, reference is made to GIGS 16 and 17. FIG. 16 illustrates the calculation of a geometric center G1 of the beam as opposed to calculation of the center of intensity A of the beam, which yields a better estimate G. It should be noted the number of photos submitted by the segment AC is the same as the number of photons emitted by AC since A is taken at the middle of the laser time.

Figure 18:
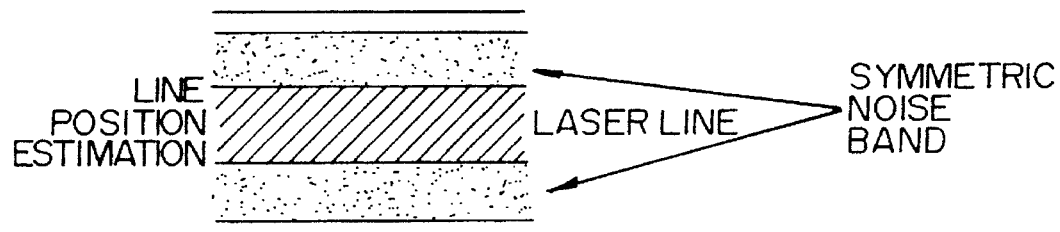
FIG. 18 is a laser line beam of the system of FIG. 1, illustrating robustness to symmetric noise.

FIG. 18 illustrates scattering of the beam on a three-dimensional object may yield symmetric noise that surrounds the laser line. The center of intensity calculation is immune to this type of noise.

Shadows normally occur because the laser is illuminating object 12 at an angle. Therefore any elevation on object 12 will shadow part of object 12. When the shadow happens to be on a useful part of object 12 that needs to be measured, it presents a problem that most of the triangulation techniques have difficulties to deal with. The gray scale processing using the center of intensity calculation for the height yields a best estimate of the height that is consistent with the illumination and object geometry as best seen in FIG. 18. In this regard, the center of intensity calculations yield an estimate G at the height that is between the height of points A and B and therefore consistent with the geometry.

Processing the raw images from the laser is done in two steps: First an intermediate image which is the compressed height image is derived from the raw image. This compressed image serves then as input for the volume, area, average height and the feature displacement calculations. This division of work is a very efficient way for dealing with the huge amount of pixels that need to be processed and permits parallel processing on the two RISC Microprocessors 34, 36 and the single 32 bit 68030 Microprocessor 44.

Considering the operation of the system 8 in still greater detail, when the projectors 20 and 22 are strobed, the cameras 23–30 acquire a set of images as beams 53 and 54 are reflected from position to position along the surface of the printed circuit board 14. In this regard, each camera such as camera 23, acquires a two dimensional image which is equivalent to 512 horizontal pixel locations. Thus, the entire reflected beam is such as beam equivalent to 8×512 pixel locations or a total of 4096 pixels in the horizontal direction. The vertical dimension of the image is adjustable between about 0.005 inches and about 0.010 inches. A more preferred beam width is about 0.007 inches. With a wide beam, a sufficient intensity of light is produced to permit a fast integration time for cameras 23–30.

The video information recorded by the cameras 23–30 is stored and processed. In this regard, a preprocessing algorithm finds the contour of the reflected beam and determines its position in image coordinates scanning every 60 positions in the vertical direction. As a result, the contour position in the image coordinates is stored in a 512 byte line for further processing.

The platform 50 is moved by the motor 40 and the above-mentioned sequence is repeated except, instead of projector 20 being pulsed, projector 22 is pulsed.

When projector 22 is pulsed, the sunrise laser beam or line 54 is projected toward the surface of the printed circuit board 14 at an angle $\theta_{SR}$. The beam 54, like beam 53, extends across substantially the entire transverse dimension of the printed circuit board 14. Under the control of the multivision processor unit 21A–H, cameras 23–30 respectively acquire an image of beam 54 as it is reflected from the surface of the printed circuit board 14.

The width of each of the beams 53 and 54 is too large for high resolution sampling. Thus, a moment or center of intensity algorithm 100 utilizing a weighted averaging method, determines the center of intensity of each reflected beam, such as beams A–D, by a gray scale technique. In this regard, the pixel image analog voltage signal from each camera is converted to a digitally encoded gray scale value indicative of the intensity of the reflected beam to a single pixel address, thus, achieving the effect of a 0.001 inch sampling grid.

The center of intensity calculation is a preprocessing step. To meet through put requirements, preprocessing is done in a parallel pipeline mode with each of the image acquisition units 21 A–H determining a compressed height data sample for each reflected beam. In this regard, the preprocessing algorithm stored in each image acquisition unit, uses the above described triangulation technique to determine base distance, such as the base distance $B_{SS}$ for a segment of the beam reflected from the beam 53 and a base distance $B_{SR}$ for a segment of beam 54. After the base distance is calculated, the algorithm then computes by the triangulation technique a compressed height distance, such as a height $H_{SS}$ relative to beam 53 and object 12, and a height $H_{SR}$ relative to beam 54 and object 12. The compressed height data, such as $H_{SS}$ and $H_{SR}$ as well as the location of the object 12 is then stored for further processing.

Figure 11:
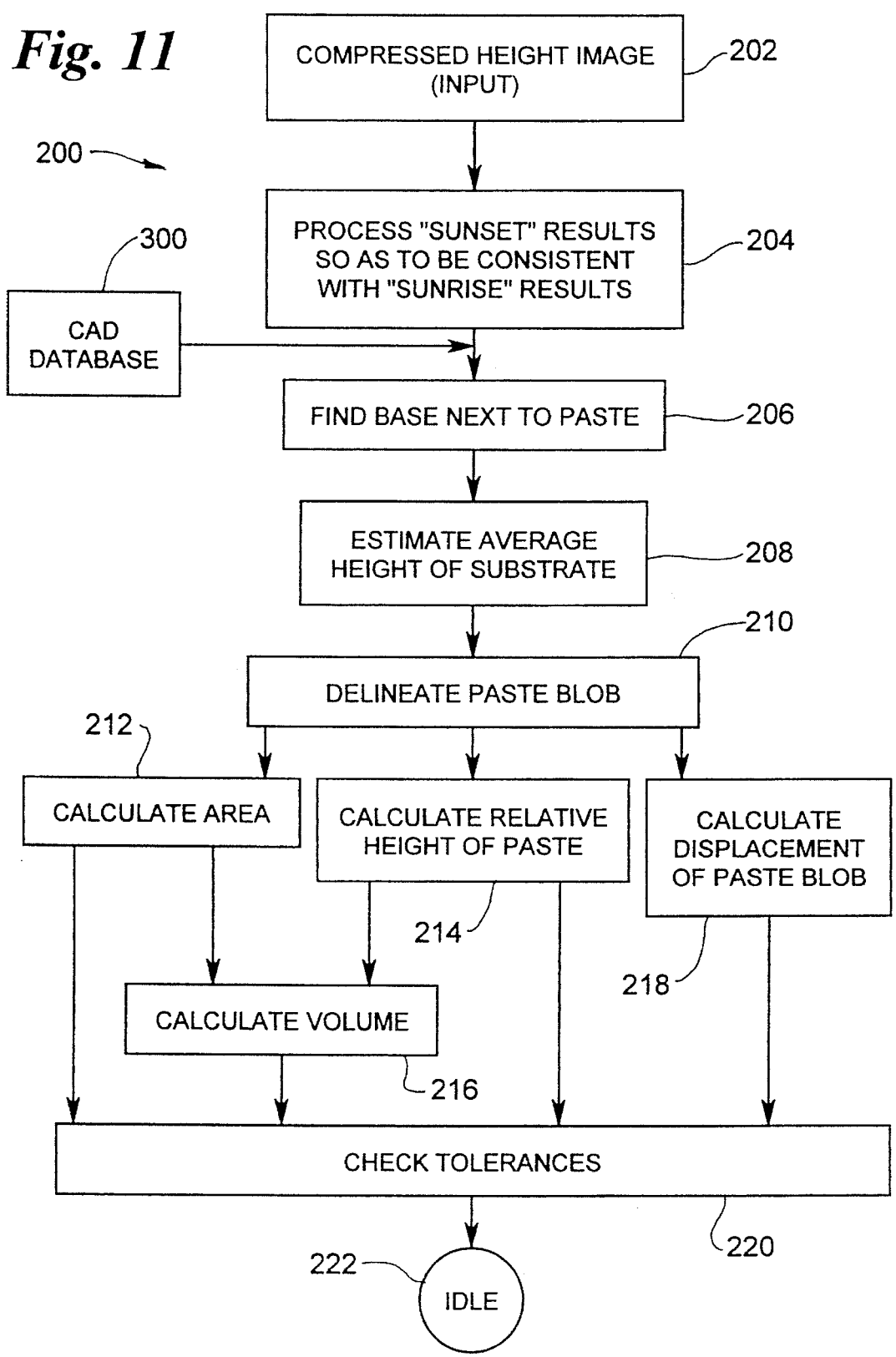
FIG. 11 is a flow chart of the geometric determination software for the image acquisition unit of FIG. 1.

After several three-dimensional features have been scanned, a geometric algorithm 200, (FIG. 11) using the compressed height data as well as the data relative to the location of each beam observed by the multivision processor unit 21A–H, calculates the height, area, displacement and volume of the each three-dimensional object on the surface of the printed circuit board 14, such as the deposit 12. In this regard, the height is determined for each deposit by the algorithm 200 calculating the local displacement with sub pixel accuracy with respect to the base line, such as the base line $B_{SS}$ for each three dimensional object. The area is calculated by the algorithm 200 finding the edges of each three-dimensional feature and accumulating the number of pixels internal to the peripheral edges of the feature. The displacement of the object 12 is calculated by comparing the mean position of the feature with respect to a prestored database. Finally, the volume is calculated by the geometric algorithm 200 integrating the height of the feature multiplied by the area calculated previously relative to the number of microsteps and field of view quantizations.

C. DETAILED SYSTEM DESCRIPTION

Figures 1, 8A:
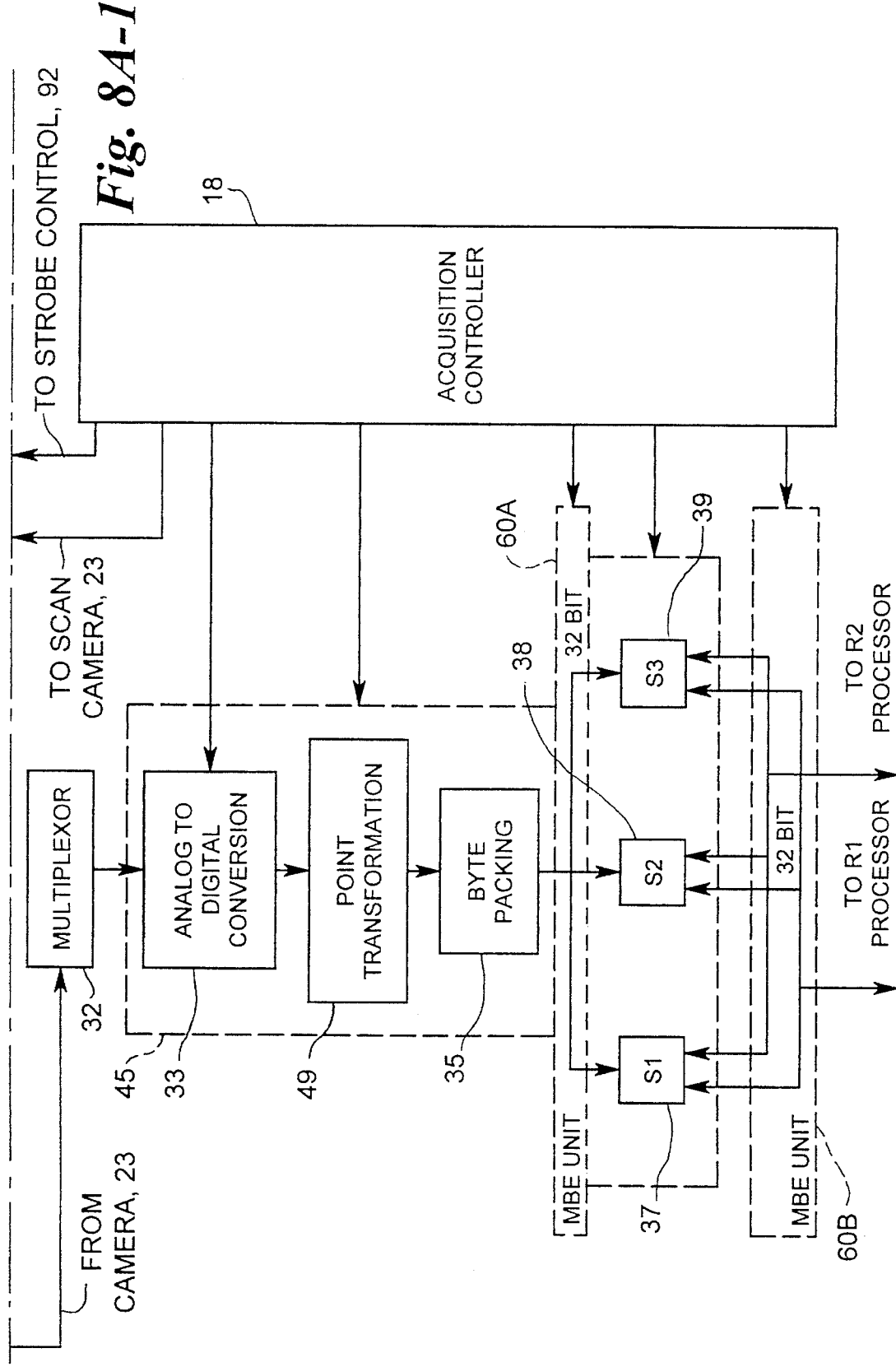
FIGS. 8A–8B illustrate a detailed block diagram of an multivision processor unit of the visualization system of FIG. 1.
Figure 8B:
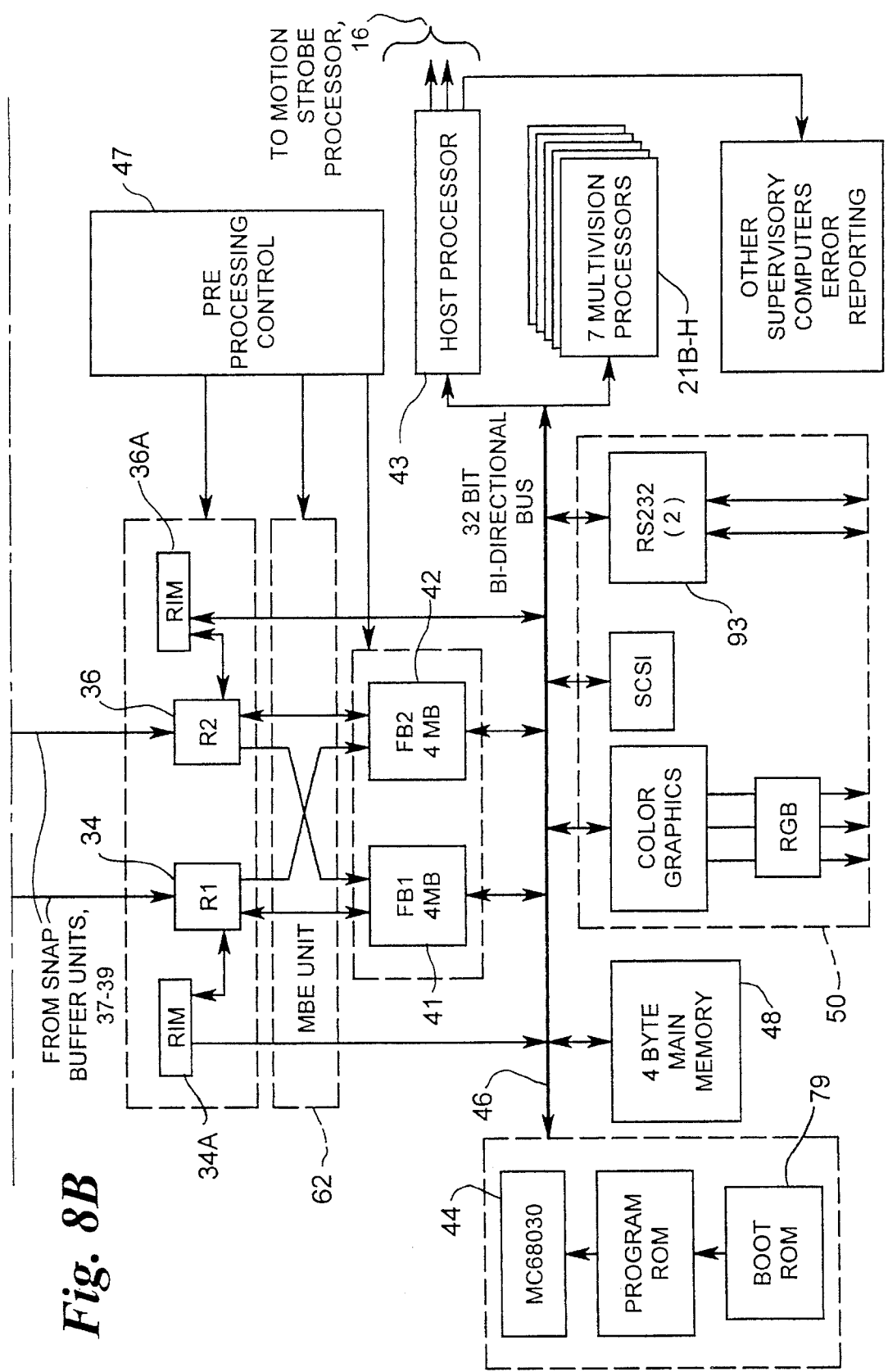

Considering now the image acquisition unit 21A in greater detail with reference to FIGS. 8A and 8B, the image acquisition unit 21A generally includes a transformation unit 45 (FIG. 8A) for converting the analog pixel image voltages generated by camera 23 into digitally encoded gray scale signals and for storing temporarily the converted signals to enable the signals to be processed into compressed height data. In this regard, the transformation unit 45 generally includes a 30 MHz flash analog to digital converter 33 for the purpose of converting the multiplexer pixel image analog voltages for processing by the RISC processors 34 and 36 respectively,. The analog to digital converter 33 is connected electrically between the output of the camera multiplexer 32 and the input to a set of snap buffer memory units 37–39 via a byte packing register 35. Control for gating and directing video data from the multiplexer 32 into the snap buffer memory units 37–39 is provided by the acquisition controller 18.

The transformation unit 45 also includes a point transformation unit 49 which transforms the digital output signals from the analog to digital converter 33 to a scaled digital value in real time. In this regard, the 8-bit digital input signal from the analog digital converter 33 is an input signal to a look up table where it is transformed by the function equivalent shifting right by two bits. The transformed values are in the range of 0 to 127. The output of the look up table has 8-bit bytes is stored in one of the snap buffer units 37–39. The RISC buffers 37–39 are organized as 32 bit wide memories and are written and read 4-bytes at a time. As will be described hereinafter, the look up table is loaded by a CISC microprocessor 44 as a part of the system boot-up procedure.

In order to control the acquisition of data from camera 23, the image acquisition unit 21A also includes an acquisition controller 18 (FIG. 8A). The acquisition controller 18 controls the scanning of pixel data from camera 23 and facilitates the conversion of the analog pixel image voltage signals into the digitally encoded gray scale signals. The acquisition controller 18 also directs the storage of the converted information into appropriate ones of the snap buffer memory units 37–39 as will be explained hereinafter in greater detail.

For the purpose of converting the gray scale signals into compressed height data, the image acquisition unit 21A further includes a pair of MC88100 RISC microprocessors 34 and 36 (FIG. 8B) and a pair of 4 MByte frame buffer memory units 41 and 42. The RISC microprocessors 34 and 36 are electrically connected between the snap buffer memory units 37–39 and the frame buffer memory units 41 and 42 via a set of crossbar data multiplexers or MBE units 60A and 60B respectively. The RISC microprocessor 34 and 36 and their associated frame buffer memory units 41, 42 also cooperate with the MC68030 CISC microprocessor 44 via another MBE unit 62. Both the CISC microprocessor 44 and the MBE unit 62 form part of the unit 21A, for post-image processing.

Either one of the RISC microprocessor 34, 36 can access any one of the snap buffer memory units 37–39 via the MBE unit 60A. Similar the microprocessors 34, 36 can access either of the two banks of frame buffers 41, 42 via the MBE unit 60B. Preprocessing consists of calculating the center of intensity of the laser beam reflected images from the gray scale image in a snap buffer at each pixel location along the horizontal and storing the results in one of the frame buffer memory unit 41, 42. The center of intensity of the laser line, when used as an address offset, determines the height of the 3 dimensional feature of the aiming point of the laser projectors 20, 22. The center of intensity algorithms are stored in a pair of RISC instruction memory (RIM) units 34A and 36A.

The 32-bit bi-directional bus indicated generally at 46 interconnects electrically the frame buffer memory units 41 and 42 with the CISC microprocessor 44 as well as the 4 MByte DRAM system memory unit 48.

In order to control the processing of the compressed height data stored in the frame buffer memory units 41 and 42, the image acquisition unit 21A further includes a pre-processing controller 47. As will be explained hereinafter in greater detail, the preprocessing controller 47 cooperates with the CISC microprocessor 44 and the image acquisition controller 18 to assure real-time operation of the visualization system 8 in determining the geometric dimensions of a large number of three-dimensional objects on the surface of the printed circuit board 14 in a very short period of time. The programming of the acquisition controller 18 is provided in Appendix A which is attached hereto and incorporated herein this specification by reference.

The visualization system 8 is a highly pipelined, parallel, image acquisition and image processing system for solving real time vision application and process control problems. In this regard, the dual RISC microprocessors 34 and 36, their associate frame buffer memory units 41 and 42, as well as the SRAM memory units 37–39 are all configured in a ping pong type architecture structure in order to allow continuous video data inputting while the dual RISC microprocessors 34 and 36 are processing acquired video or image data. Thus, image acquisition, pre-processing and post-processing can occur in parallel at both the RISC microprocessor and the CISC microprocessor levels.

Figure 14:
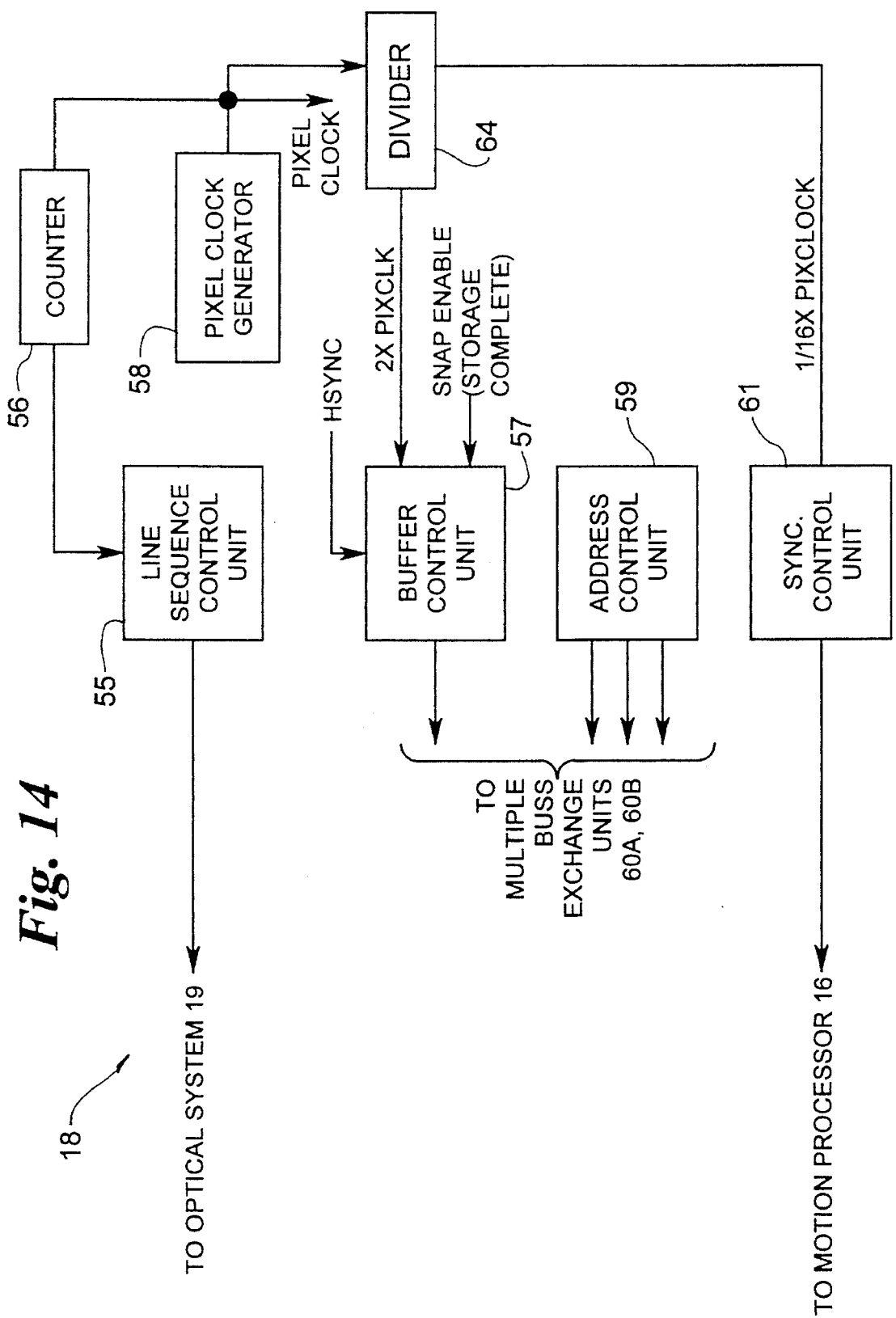
FIG. 14 is a block diagram of part of the image acquisition controller of FIG. 8A.
Figure 15:
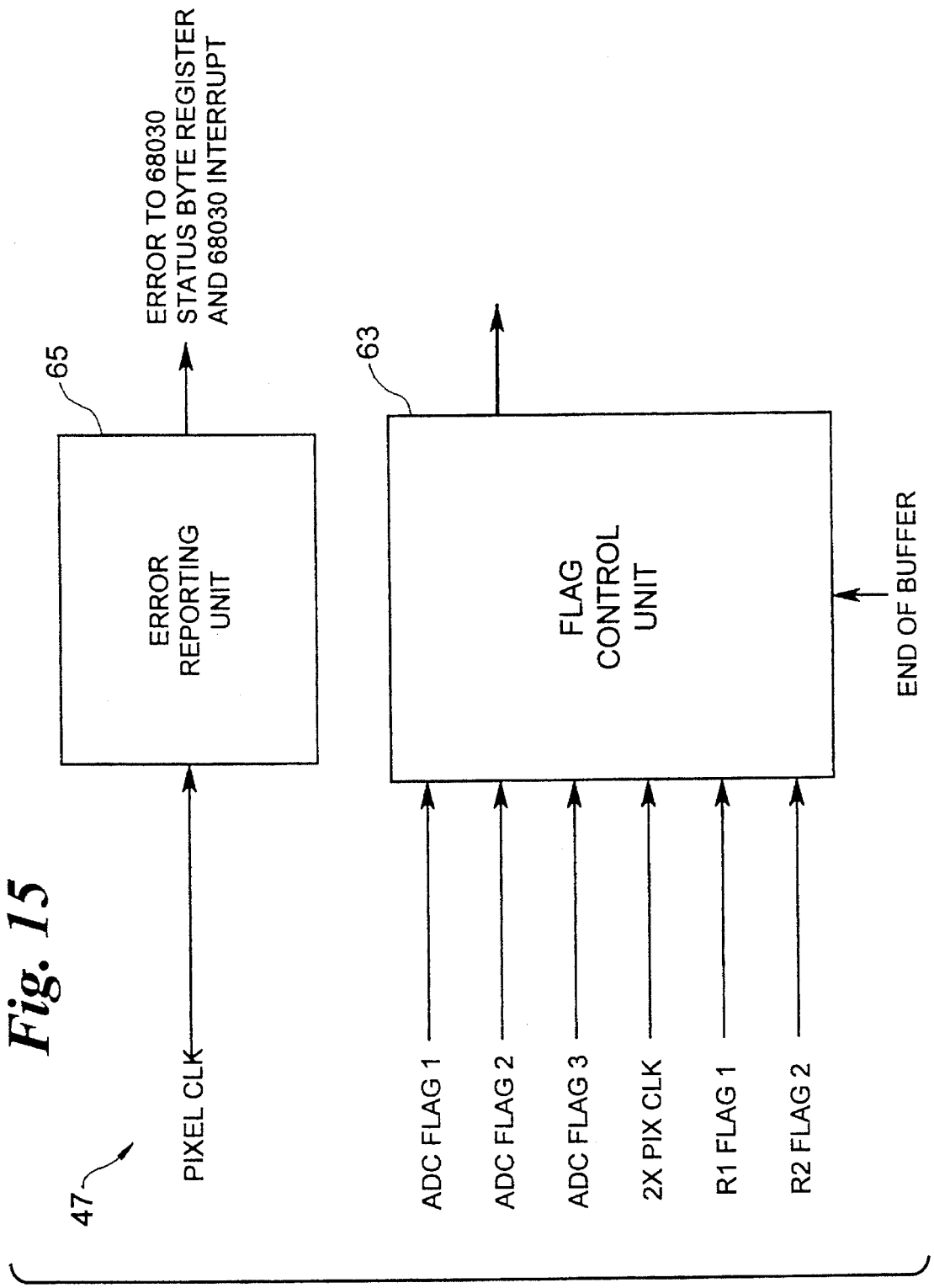
FIG. 15 is a block diagram of another part of the image acquisition controller of FIG. 8.

Considering now the acquisition controller 18 in greater detail with reference to FIGS. 14 and 15, the acquisition controller 18 generally includes a line sequencing control unit 55 which controls the sequencing of reading camera data via the multiplexer unit 32. The sequence control unit 55 is a conventional AM27S291A PROM. The controller 18 also includes a pixel clock generator 58 for providing reference timing signals, a line counter 56 and a pixel clock divider 64.

The acquisition controller 18 further includes a buffer control unit 57 and an address control unit 59 for control 17 the addressing of data from the byte packing register 35 into the appropriate snap buffer memory unit. The buffer control unit 57 and the address control unit 59 are PAL 22V10 type units. The buffer control unit 57 and address control unit 59 are connected to a set of buffer multiplexer holding register or multiple bus exchange (MBE) units 60A, and 60B. Each MBE unit 60A, 60B is a four port, registered multiplexer which latches the buffer address supplied from the address control unit 57 and routes data from the byte packing register 35 and snap buffer memory units 37–39 for the different read/write operations. The MBE units 60A, 60B are 9-bit×4 port multiple bus exchange chips, manufactured by Advanced Micro Devices under part no. AM29C983.

The buffer control unit 37 selects which MBE port the address and data are to be routed and places the proper address select lines and data select lines on the inputs to the appropriate MBE unit. When the selection is made, the data source is selected and the data destination is selected. When loading a buffer memory, the source is the analog to digital converter 33 and the destination is one of the buffer memory units 37–39. Similarly, the RISC processors 34 and 36 are assigned read/write access to one of the three snap buffer memory units 37–39 via the MBE unit 60B as determined by the control select line signals generated by the buffer control unit 57.

For the purpose of synchronizing the camera 23 with the strobing of the projectors 20 and 22 and controlling the advancing or stepping of the servo motor 40, the acquisition controller 18 further includes a synchronization control unit 61. The control unit 61 is a 27C010 EPROM.

The acquisition controller 18 further includes a flag control unit 63 to control a set of flag signals ADC FLAG1, ADC FLAG2, ADC FLAG3, R1 FLAG1 and R2 FLAG2 signals. The flag signals and the flag control unit 63 will be described hereinafter in greater detail. The flag control unit 63 is a PAL 22V10 unit.

As best seen in FIG. 1, the controller 18 also includes an error reporting unit 65. In this regard, during the data input process, a data overflow condition can occur if a given one of the RISC processors 34, 36 has not completed processing the data stored in the active snap buffer memory unit. Thus, if at the time the controller 18 needs a RISC microprocessor for the next snap input, and the selected RISC microprocessor is not available, an error condition will result. The error reporting unit 65 causes an error signal to be generated which is transferred to the CISC microprocessor 44 for appropriate action as will be explained hereinafter in greater detail. In any event, it should be understood, that such an error condition does not prevent data from being loaded into the snap buffer memory units 37–39. The error reporting unit is a PAL 16R8 type unit.

Considering now the preprocessing controller 47 in greater detail with reference to FIG. 8B, the preprocessing controller is a sequence logic control module implemented with eight PAL'S. In this regard, the controller 47 generates frame buffer memory access arbitration, memory cycle control signals, processor wait state and multiplexer or MBE control.

The frame buffer sequence is controlled by a set of three PALS (22V10's) for request, grants and control. The DRAM RAS/MUX/CAS sequence and access is controlled by two PAL16L8's for address control, one PAL20L8 for write enable, one PAL16L8 for DRAM enable, and one PAL16R8 for RAS/MUX/CAS cycle and synchronous terminate.

Figure 9B:
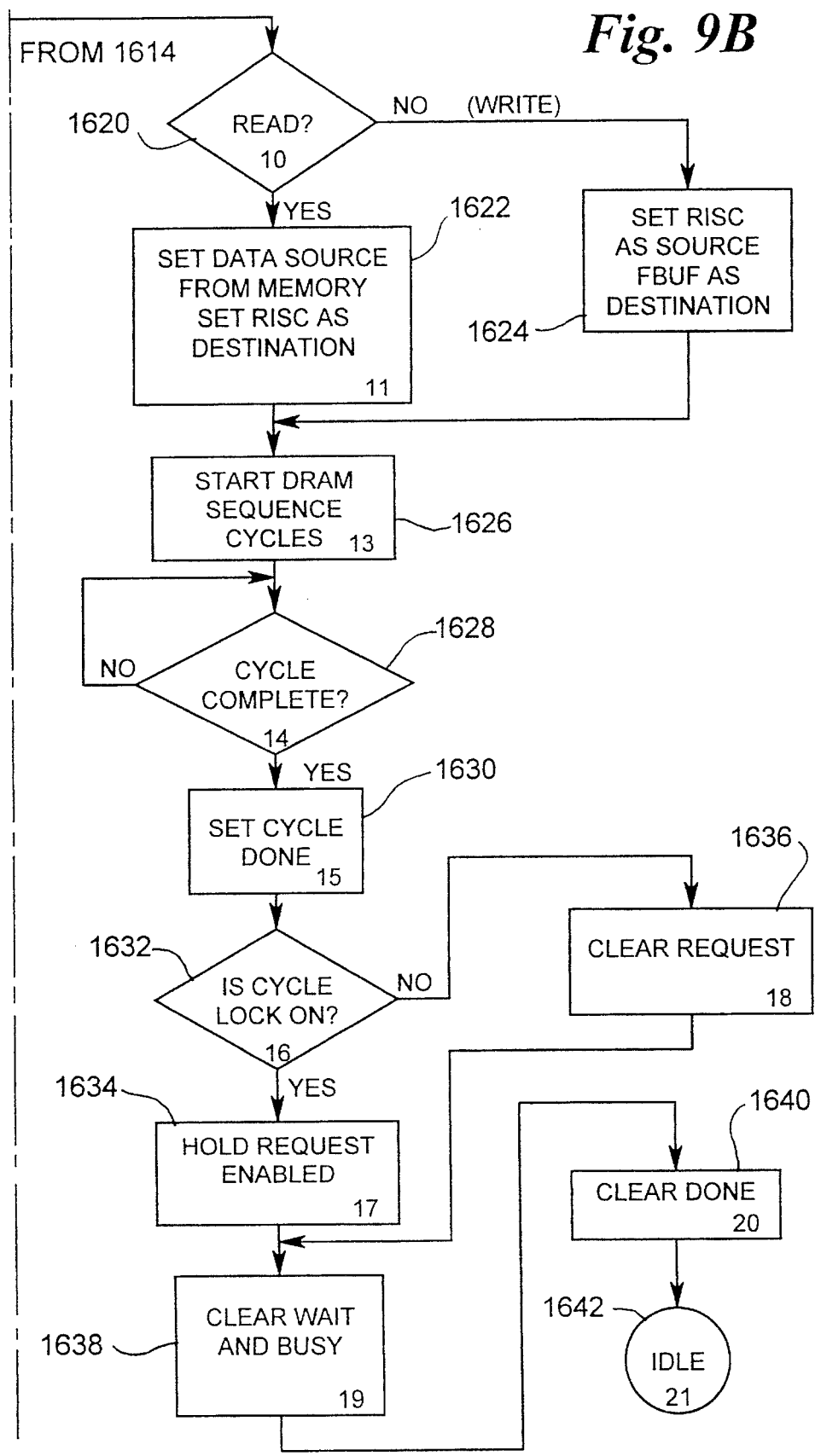
FIG. 9 is a flow chart of software for the preprocessing controller of FIG. 15.

FIG. 9 is a detailed description of the sequencing of the controller 47 relative to the RISC microprocessors 34, 36, the CISC microprocessor 44, the MBE unit 62, and the frame buffer memory units 41, 42. Appendix B attached hereto is the complete programming of the PALs which comprise the controller 47. Appendix B is incorporated herein this specification by reference.

Considering now the controller 47 in still greater detail, the frame buffer memory units 41, 42 can be accessed by either the RISC1 microprocessor 34, RISC2 microprocessor 42, or the CISC microprocessor 44. The access sequence is started when an address is decoded that specifies either frame buffer memory 41, or frame buffer memory 42. Both frame buffers 41, 42 operate in the same manner. When a frame buffer address is decoded, a "FB Request" is generated to the arbitration logic.

The "Arbitrator" determines if it already has an active request/grant in process, or if it can start a new cycle. The arbiter performs arbitration between RISC1 microprocessor 34, RISC2 microprocessor 36, and the CISC microprocessor 44. All requests are received and all grants are given on a request in priority. Therefore, no one of the microprocessors 34, 36, 44 can be held off for more than two memory cycles before an access is given. The arbiter responds to the "FB Request" with an "FB Grant" signal.

As the sequencer generates the request to the arbiter, it also latches the address and read/write signal into the multiplexer crossbars or MBE unit 62. This holds the "pipelined" address for the RISC processors. When the frame buffer is "Busy" due to a previous access, the sequencer sends a "Wait Response" to the active RISC processor, since access to the frame buffer memories 41, 42 is longer than one RISC processor cycle.

When the frame buffer memory units are not busy, the controller 47 sends a "FB Enable" signal to the DRAM sequencer to start the DRAM memory cycle. The DRAM sequencer receives the enable signal and checks for an active DRAM refresh cycle. If a refresh is in progress, the enable is held off until the refresh has been completed. The sequencer then enables the row address and generates a RAS signal to the memory. It then changes the MBE unit 62 to column address and generates a CAS signal. A write enable is issued if a write cycle is active. If the read cycle is active, the output of the memory is enabled onto the output bus. The DRAM sequencer provides the proper timing for signal setup, precharge times, pulse lengths and memory cycle time. At the end of the memory cycle time, a synchronous terminate signal is generated from the DRAM sequencer, sent to the frame buffer sequencer and a cycle done flag is set.

When the end of the current cycle is detected, the FB sequencer checks for an active "Data Bus Lock" signal. An active DB Lock will keep the present FB request signal enabled, and not allow another device to access memory. This is for Read-Modify-Write types of accesses and prevents memory from being changed before the total lock sequence is complete. If the lock signal is active, the RB sequencer holds onto the request, but clears the RISC wait signal and the frame buffer busy signal. If the lock signal is not active, the sequencer clears out the RB request signal, along with the wait and busy signals. The sequencer then clears the "Cycle Done" flag, and returns to an idle state, waiting for a new FB request from either of the RISC microprocessor 34, 36 or the CISC microprocessor 44.

Both frame buffer sequencers are identical in their response to FB requests. Since each frame buffer has a unique system address, each frame buffer can be active at the same time from the different requesting devices, RISC1 microprocessor 34, RISC2 microprocessor 36 or CISC microprocessor 44.

Considering now the motion/strobe processor 16 in greater detail, the processor 16 generally includes a linear encoder 69 for generating a series of pulses which are indicative of the relative movement of the platform 50 along its path of travel. The processor 16 also includes a motion control unit 91 and a strobe control unit 92. The motion control unit 91 causes the motor 40 to move the platform 50 at a constant rate of speed long the substrate 14. In this regard, the motion control unit 91 is responsive to the linear encoder 69 and generates a series of output signals which pulse motor 40 to move platform 50 along its path of travel. In this regard, for each pulse received, the motion control unit 91 causes the motor 40 to be stepped by one micro-step. The motion control unit 91 is a Compumotor AXL micro stepping stepper motor controller.

The strobe control unit 92 controls the firing of the laser projectors 20 and 22. In this regard, the strobe control unit 92 initiates a strobing sequence under the control of the host processor 43. The strobe control unit 92 is responsive to the linear encoder 69 to cause the laser projectors 20 and 22 to be strobed about every 0.003 inches along the path of travel of platform 50. At this strobing rate, a very large number of line images are produced in a very short period of time. The strobe control unit 42 provides a count input to a counter chip (not shown) in the host processor 43. When the count equals zero the host processor 43 generates a trigger signal to a transistorized switch (not shown) which energizes the appropriate laser projectors for about 200 μseconds.

Considering now the host processor 43 in greater detail with reference to FIG. 8B, the host processor 43 detects the trigger signal generated by a photo electric sensor (not shown) via an interrupt input (not shown) to start an inspection procedure.

When the host processor 43 detects the trigger signal it sends a message via a conventional shared memory communication protocol over the share memory buss 46 to a UNIX processor (not shown) which transfers the control messages to each of the multivision processor units 21A–H as well as the motion control processor 16 to begin the inspection tasks.

The first task is performed by the motion processor 16 to start the servo motor 40 to cause the camera array 23–30 to begin a scan across the substrate. As the cameras 23–30 move, pulses are generated from the linear encoder. The host processor 43 via the strobe control 92 counts the pulses, then fires the laser strobe lights at predetermined intervals (approximately 0.003 inches apart). At each firing of the strobe light, each of the eight multivision processors 21A–H read the illuminated image from its own cameras 23–30 respectively. The camera data are processed, in parallel by the processors 21A–H. The intermediate results of all the images are stored in the frame buffers 41, 42.

The host processor 43 keeps a count of the number of laser strobe firings and thus, can determine when the substrate has been fully sampled. The host 43 thus, stops the scan and signals indicative then the scan phase of the inspection is complete. The host 43 then requests the inspection results from each of the eight vision subsystems and then assembles those results into a composite analysis of all the pad data; XY location and volume.

The next step performed by the host 43 is to check the data against the database loaded at startup and determine PASS/FAIL information. The PASS or FAIL result is then sent. A trigger signal material handling system (not shown) to unlock the substrate and to index it from the holder and allow a new substrate in. Scanning is bi-directional to improve throughput of the system. If FAIL is the result, then the host 43 will either stop the entire material handling system and provide an alarm to the operator or, optionally, cause the material handling system to automatically divert the substrate to a reject handler.

In all cases, all results data are logged on a disk (not shown). A background program running on the host 43 creates reports in variable formats which are output, on command, to printers, CRT screens, networks, etc. System operators use the reports to determine quality of the process and to make corrections to the process.

The inspection cycle repeats continuously without operator intervention for any one 3D object type.

D. DETAILED SYSTEM OPERATION

In operation, the visualization station 11 in cooperation with image processing system 13 produce a series of image signals which are indicative of the transitions and surfaces of the three-dimensional objects on the surface of the printed circuit board 14. In this regard, the signals produced by the transformation unit 45 are gray scale coded signals with values which are proportional to the intensity of individual the beam on deposits on the surface of the printed circuit board 14.

The image acquisition controller 18 processes the image signals and stores a resulting set of compressed height image signals which are indicative of the positional locations of each of the deposits on the surface of the printed circuit board 14 as well as the height of the individual deposits, such as the deposit 12.

The imaging acquisition unit 13 causes the compressed height image signals to be compared with a computer aided design ("CAD") database 300 (FIG. 11) which is indicative of the positional locations of the solder pads on the printed circuit board 14. In this regard, the geometric algorithm 200 (FIG. 11) forming part of the image acquisition unit 13, finds the base of the individual paste deposits relative to each pad on the printed circuit board 14 by comparing the gray scale signals detected in the area around each pad. Statistical techniques are used to test for uniformity of the height of each deposit associated with each pad. In this regard, the algorithm 200 determines the number of gray scale pixel image signals within the periphery boundaries of a given solder paste deposit to determine the area of the deposit. The average height of the deposit is then determined by averaging the height as determined from the displacement within the calculated area of the deposit. The displacement of the deposit is then determined by finding the centroid of deposit and then subtracting it from the centroid of the solder pad as stored in the CAD data base 300. Finally, the volume of the deposit is calculated by summing the gray scale signals for each pixel location inside the defined image area and correcting the results taking into account the field of view and stage micro-step quantization.

Once the volume of each deposit has been calculated, the individual deposits are compared with pre-stored tolerance values set externally in the CAD database 300. If any deposit is found to be outside of the allowed tolerance, an error signal is generated to cause the printed circuit board 14 to be rejected from further processing steps.

Considering the operation of the multivision processor 21A in still further detail, whenever a new inspection of a printed circuit board is to begin, the CISC microprocessor 44 sends a sync reset signal to the acquisition controller 18 to start a new data acquisition sequence. Responsive to the sync reset signal, the acquisition controller 18 causes projector 20 to be strobed or fired allowing camera 23 to store a visual image. The controller 18 then generates a control signal SNAP COMPLETE to start a data acquisition sequence. In this regard, the controller 18 causes the flag control unit 63 to set signal an ADC FLAG 1 which permits the pixel analog voltages from camera 23 to be accessed sequentially via the multiplexer unit 32. Each of the analog voltage signals is converted into an 8-bit digitized signal which is indicative of a given gray scale intensity level. The analog value of the brightness (gray level) is converted to an eight bit number (0 to 225) at the rate of 24,000,000 pixels per second. The eight bit value becomes an input to a lookup table where it is transformed by the function equivalent shifting right by two bits. The transformed values are in the range of 0 to 127. The output of the lookup table (as 8 bit bytes) is stored into one of three snap buffer memory units 37–39 which can be operated upon by one of the two RISC processors 34, 36. The RISC frame buffer memory unit 41, 42 are organized as 64 bit wide memories and are written and read four bytes (pixels) at a time. This arrangement permits up to 256 different intensity levels to be converted into 8-bit digital codes.

The image acquisition controller 18 and preprocessing controller 47 provides the synchronized storage of the transformed pixels into the RISC frame buffers memory units 41 and 42 respectively. The acquisition controller 18 is configured as a "line grabber" rather than the traditional frame grabber. By operating in line grab mode, the controller is capable of being easily programmed to store a preset number of line from a standard camera. The acquisition controller 18 recognizes the horizontal synchronization pulse from which it starts its count down to each of the active video pixels in the scan line.

From each scan line, 512 pixels will be stored into one of the RISC frame buffers memory units 41, 42. In this regard, the number stored in each memory location represents the height of the image. In this regard, the pixels have already been transformed by the look up table to a form comprising six significant bits with the two most significant bits being zeros. Because the RISC processors 34 and 36 will be computing the average value of all the pixels in a column across the laser line image, it is necessary to fill the entire byte to the left of a pixel value with zeros. By pre-packaging the data, the RISC's 34, 36 can perform arithmetic operations on two bytes in one memory fetch and one machine instruction without the need to handle overflows. Prior to initiating a memory write, the acquisition controller 18 accumulates the data in the following format:

OOOOOOOO OOpppppp OOOOOOOO OOpppppp, where p is a data bit derived from the gray level value.

The acquisition controller 18 manages the utilization of the three RISC snap buffers 37–39 by filling them in round-robin fashion and assigning one of the two RISC's processors 34, 36 when a buffer memory unit is filled and ready to be processed. The entire process is synchronous. The RISC's processors 34, 36 always complete the snap buffer operation before that snap buffer memory unit is required for the next laser line. In other words, by using three snap buffers, the RISC's processors 34, 36 have two line acquisition times to process one line.

Each 8-bit code is then stored in the byte packing register 35 until four bytes or 32-bits of video data have been accumulated. Once 32 bits of data have been stored in register 35. The line sequence control unit 55 causes a line counter (not shown) to be incremented. This process of converting, storing and incrementing is repeated until the acquisition controller 18 generates a signal DATA ENABLE which is indicative that the data stored in the byte packing register 35 is valid data. In this regard, data is valid from pixel clock 132 to 772 on each line and from row 20 to row 492 for each frame.

Once the DATA ENABLE signal is generated, every 32 bits of data accumulated in register 35 is latched into the snap buffer multiplexer holding register or multiple bus exchange (MBE) unit 60A. The snap buffer multiplexer holding register 60A directs the stored data and address information received from the controller 18 to one of the snap buffer memory units, such as the memory unit 37. This process is repeated continuously until the end of a video field is reached; i.e., all of the camera image data of interest has been stored.

At the end of the video field, the controller 18 causes the flag control unit 63 to set a signal ADC FLAG2, reset the signal ADC FLAG1, and set a signal R1 FLAG1 which enables the RISC microprocessor 34 to start processing the data in the snap buffer memory unit 37.

When the signal ADC FLAG2 rises to a positive or HIGH level, cameras 23-30 are reset and laser projector 22 is strobed or fired permitting cameras 23-30 to store a new image. In this regard, the pixel analog voltages from cameras 23-30 are once again accessed sequentially via the multiplexer unit 32 and converted into digitized signals. This group of signals, indicative of the second line or beam image reflected from the printed circuit board 14, is stored in snap buffer memory 38 in the same manner as the first image was stored. In this regard, video data is converted to digital information and then stored in the byte packing register 35 and transferred to the snap buffer memory 38 via the snap buffer multiplexer holding register 60A under the control of controller 18. Data is continuously stored until the end of the video field is reached.

When the end of the video field is reached, the controller 18 causes the flag control unit 63 to set an ADC FLAG3 signal, reset the ADC FLAG2 signal and set a R2 FLAG2 signal which enables the RISC processor 36 to start processing the video data in snap buffer memory 38.

When the second reflected beam image has been stored, the controller 18 causes the strobe to fire at a new scanning location enabling another area of the board 14 to be inspected. Thus, when the signal ADC FLAG2 rises to a positive or HIGH level, camera 23 are reset and laser projector 20 is strobed or fired permitting camera 23 to store another image. This image is stored in substantially the same manner as previously described except the data is stored in snap buffer memory 39.

Data is stored in snap buffer memory 39 until the end of another video field is reached. When the end of another video field is reached, the flag control unit 63 causes the ADC FLAG1 signal to be set, the ADC FLAG3 signal to be reset and the R1 FLAG1 signal to be set which causes the RISC processor 34 to begin processing the data in snap buffer memory 39.

The foregoing sequence for loading the snap buffers 37-39 sequentially in a repeated sequence, setting and resetting control signals continues until all data for a particular inspection is completed. At the end of such an inspection, the pre-processed data will be stored in the frame buffer memory units 41 and 42 via MBE unit 60B and ready for further processing by the CISC microprocessor 44 as will be explained hereinafter in greater detail.

E. OPTICAL SYSTEM

Considering now the optical system 19 in greater detail with reference to FIGS. 1, 3, 5A–C and 17, the optical system 19 enables eight commercially available cameras 23-30 to be mounted by the mounting plate 94 so that one segment of an imaged area, which measures 0.5 inch by 3.45 inches, is focused on the CCD imager of each camera. Each individual camera/lens system is configured to subtend a field of view of 0.5 inches by 0.5 inches. Eight such fields of view are concatenated on 0.35 inch centers using the mirror and beam splitter arrangement illustrated in FIG. 3. The fields of view overlap by 0.15 inches. In this regard, the overlap serves two purposes: (1) the system need not deal with partial objects and (2) the seaming and alignment problem is facilitated.

Figure 3:
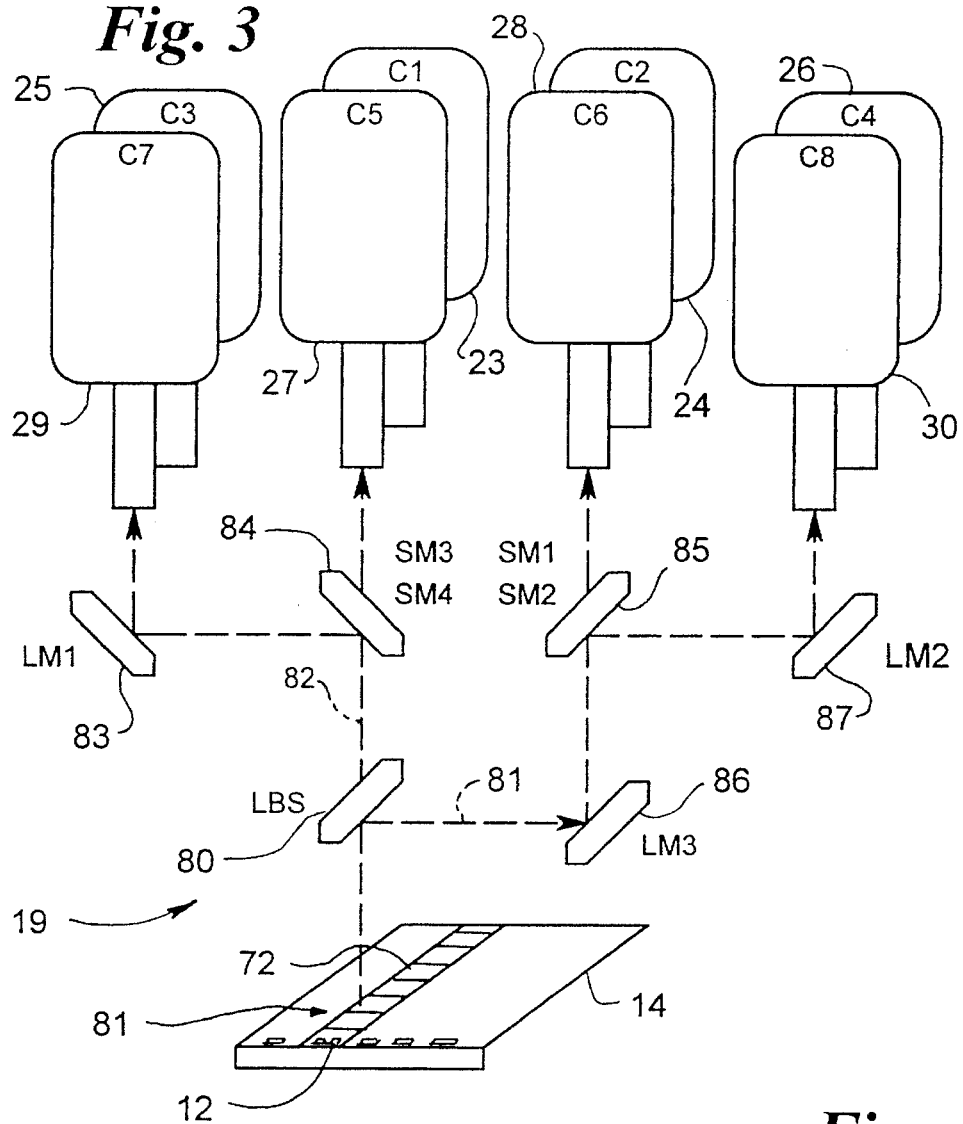
FIG. 3 is a diagrammatic view of an optical system of the visualization system of FIG. 1.

The cameras used in the system (commercially available from Panasonic) have bodies which are 2 inches by 2 inches in cross section. Their physical size prevents them from being mounted, side-by-side, eight on 0.35 inch centers, hence the need for a mirror and beam splitter arrangement as shown in FIG. 3.

In order to collect all eight of the picture segments, the light path is split and deflected using a 50—50 beam splitter and a set of surface mirrors. In this regard, as best seen in FIG. 3, a long beam splitter (LBS) 80 separates the ray paths into two ray paths; a reflected path 81 and a transmitted path 82. The transmitted rays 82 strike the lenses of two cameras 23 and 27, while the reflected light ray 81 is bent one more time by a long mirror (LM) 86 and strikes the lenses of two different cameras 24 and 28. A set of small mirrors 84 and 85 are placed in the ray path where they can't be observed by the inside cameras 23, 24, 27 and 28 respectively. A set of mirrors 84 and 85 bend the light to the four outside cameras 25, 29 and 26, 30 respectively.

The lens system of each camera is uniquely designed to provide the exact same field of view of all other lenses in spite of the differences in focal length. Camera gain and aperture openings are used to assure equal light intensity at each camera. Telocentric lenses are used to assure that the view remains in focus and at a constant field of view size as minor changes in object distance arise.

Figure 4:
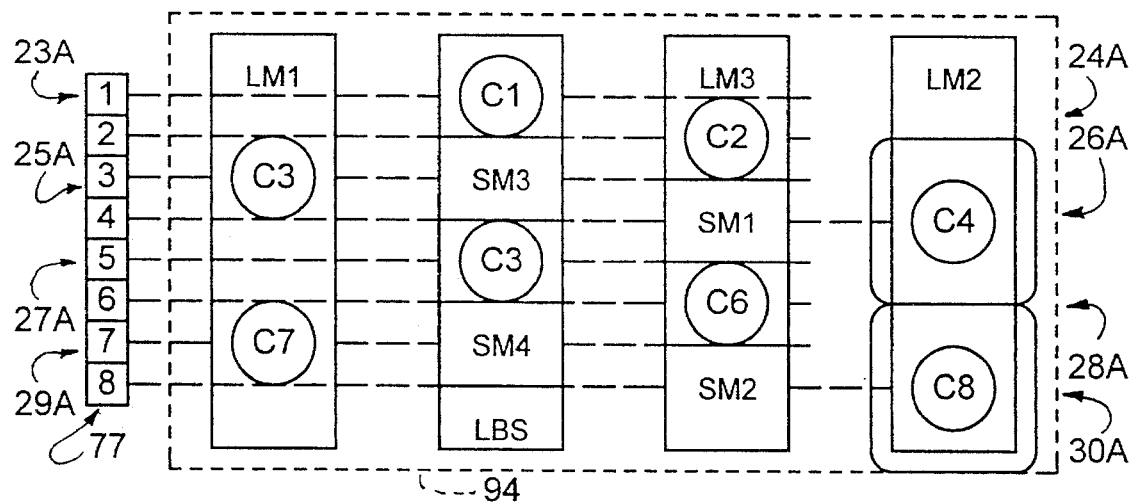
FIG. 4 is a diagram of a mounting arrangement illustrating the field of view of each camera of the optical system of FIG. 3.
Figure 5A:
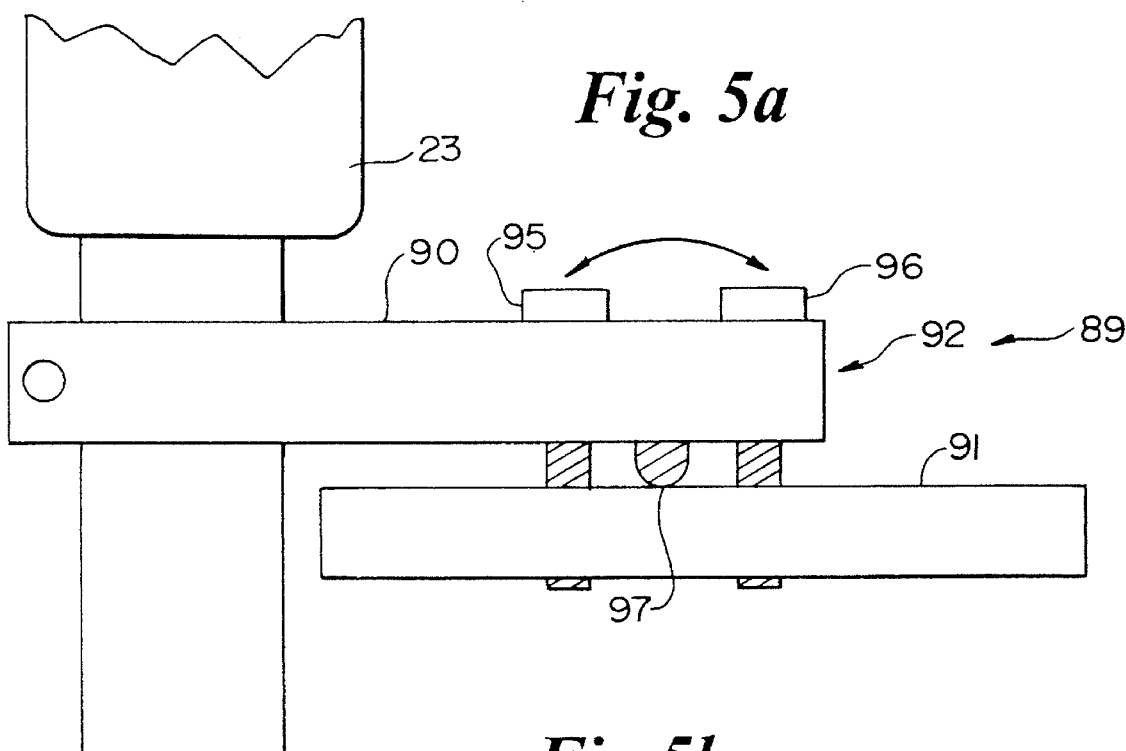
FIGS. 5A–C are diagrammatic views of a lens alignment arrangement of an individual one of the cameras of FIG. 3.
Figure 5B:
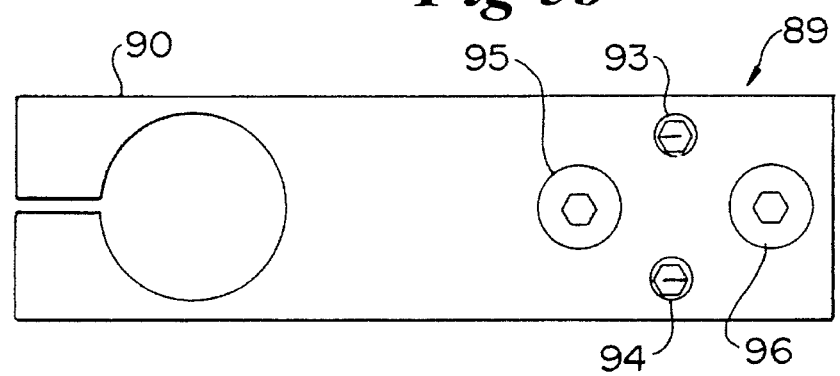
Figure 5C:
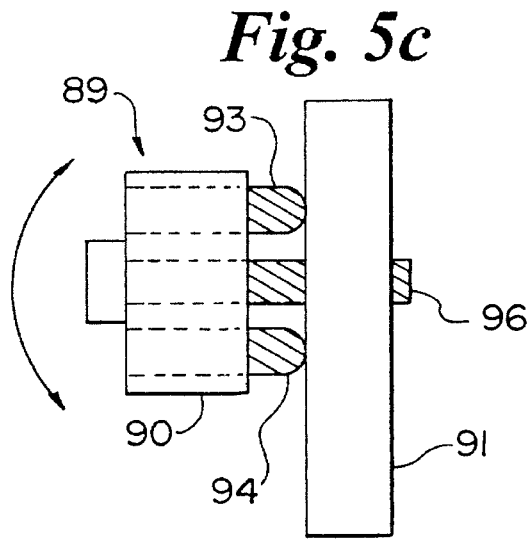

Referring now to FIGS. 3, 4 and 5A–C, although exact machining can assure an accurate spatial relationship among the eight cameras, final fine adjustments are needed to align the eight images within less than 0.001 inch in X, Y and rotation. To make the adjustments, one camera near the center of the array is aligned using precision mechanical measuring tools. That camera becomes the reference for all other cameras. The other seven cameras align to a precise viewing grid tool (cross-hairs) which is first centered on the reference camera 25. Cameras are not aligned by sliding them in X and Y directions but rather, by pivoting them on a gimbal mount 89 (FIGS. 5A–C). Pivoting is acceptable because of the length of the focal path relative to the error in inter-camera spacing results in angular differences from the orthogonal so small as to be insignificant. The camera pivot mount 89 utilizes readily available course thread machine screws to obtain micrometer-like adjustment increments. The novelty of the system lies in the method of bringing the lens aiming direction to the final, locked position. Whereas traditional aiming devices use a back and forth loosening and tightening with a final lock-down scheme, the method described herein uses tightening only and no final lock-down.

The pivot mount 89 generally includes a camera/lens mounting clamp 90 which rests on an upper surface 91 of a fulcrum indicated generally at 92. The fulcrum 92 is mounted to the platform 50 by means not shown. A pair of screws 93 and 94 pass through the clamp 90 and are held in compression against the surface 91 by another pair of screws 95 and 96 in tension on either side of a fulcrum point 97. Shortening or lengthening the fulcrum screws 93 and 94 will change the aim of the lens in the ±Y direction while shortening or lengthening the screws 95 and 96 will change the aim of the lens in the ±X direction. Once near target center, the screws 93–96 are turned in the tightening direction only. As forces are applied to the screws, the metal in both the screws and the mounting clamp distorts slightly changing the aim of the lens. When the lens is on target, tightening stops and the alignment is complete; there is no need for a final locking step.

F. LASER BEAM PROJECTORS

The three dimensional measuring system of system 8 relies on the principal of triangulation wherein the unknown side of a right triangle can be determined if one of the sides is known and one of the acute angles is known. In this regard, cameras 23 to 30 are oriented at right angles to the horizontal plane of the objects being measured and a structured light source projects a wide line or beam of laser light at a known angle relative to the same plane.

Considering now the projector unit 20 and 22 in greater detail with reference to FIG. 1, two banks of laser line projectors 20, 22 are used in the system. One bank leads the cameras and the other bank follows the cameras. The laser 20 and 22 include groups of laser diodes which are strobed or pulsed alternately (referred to as "sunrise" and "sunset") so that features of the surface which may be hidden from the light from one side have an opportunity to be illuminated from the opposite side (peaks and craters are such features).

The laser diodes, operating in the pulsed mode are able to achieve a higher degree of intensity level permitting an increase in the signal to noise ratio. Furthermore, the output intensity of the laser diodes are focused and summed in order to achieve an even higher constant intensity laser line across the whose useful line width of the beam.

Figure 7:
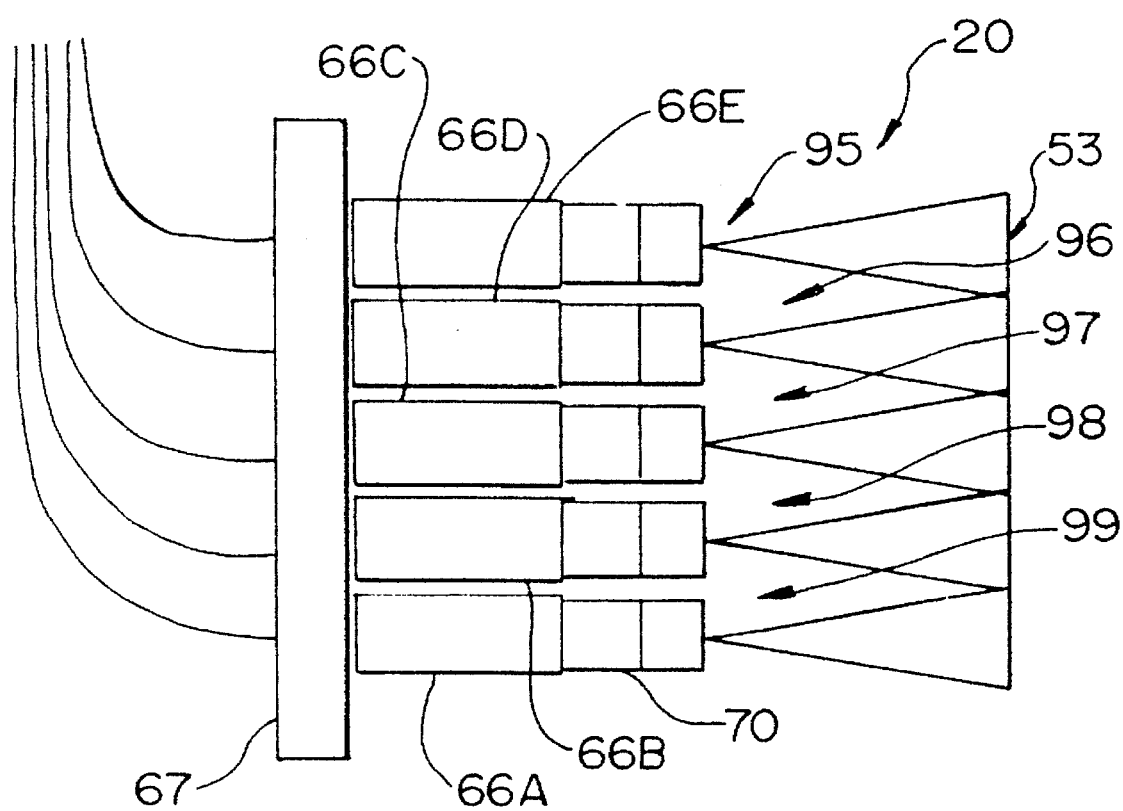
FIG. 7 is a top plan diagrammatic view of a laser line generator of the visualization system of FIG. 1.

To achieve a line or sheet of laser light using commercial solid state lasers a group of laser diodes such as diodes 66A–E (FIG. 7) are mounted side by side to a mounting plate 67 as shown in FIG. 18. The plate 67 is mounted to the platform 50 by means not shown and includes an alignment mechanism (not shown). The alignment mechanism for the laser diodes 66A–E is implemented the same as described above for the camera/lens system. Four screws (not shown) are used in compression and tension.

Figure 6A:
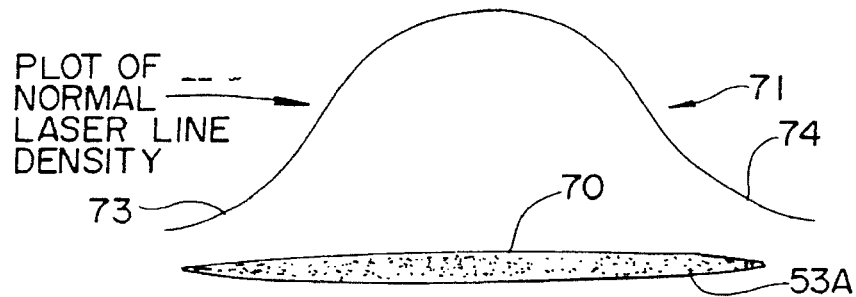
FIGS. 6A–C are diagrammatic views of a laser beam produced by a laser beam projector assembly of the visualization system of FIG. 1.
Figure 6B:
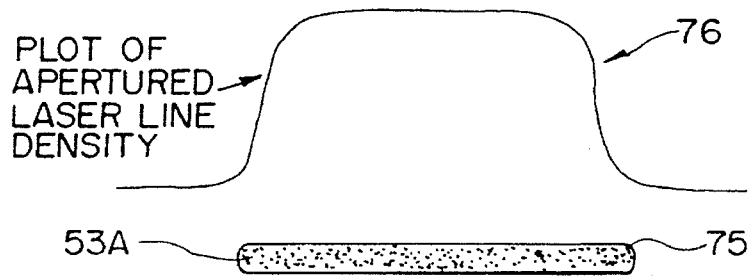
Figure 6C:
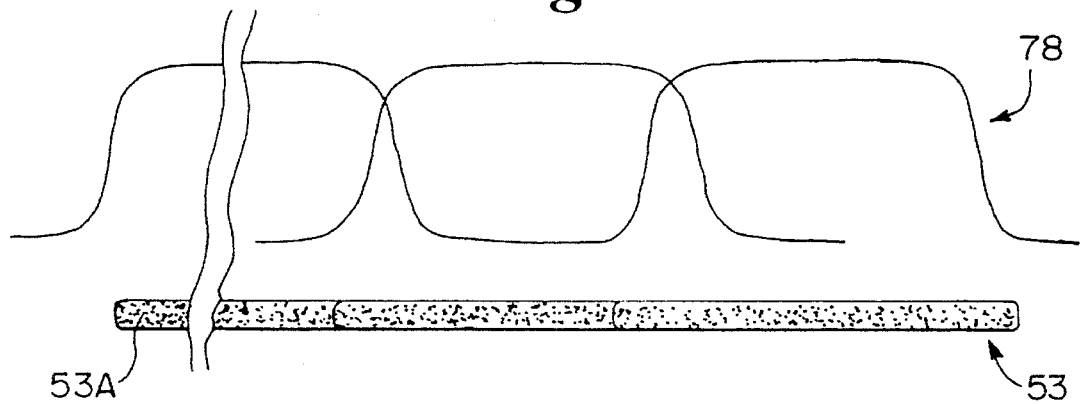

Referring now to FIGS. 6A, 6B and 6C, in order to convert a laser diode beam to a line of light requires a spreading lens, such as a spreading lens 70 is mounted by means not shown to each diode. The lens 70 widens the spot of light. Widening results in a beam 53A whose density distribution is shown at 71. Although the beam 53A is wide and thin, it lacks uniform distribution. In order to improve the distribution density of beam 53A, The outer, weak edges 73, 74 of the beam 53A as shown in FIG. 6A are cut off using a mechanical aperture 75. The aperture 75 changes the distribution to that shown generally at 76. A set of five such sources 95–99 (FIG. 7) of approximately 0.6 inches wide are concatenated to form the laser line or beam, such as the beam 53 which creates an illuminated area 77 which is about 3 inch long by 0.002" to 0.005" wide. The illuminated area 77 has a nearly uniform density of light on the inspected surface. The density of the beam 53 is shown graphically at 78.

Referring now to FIG. 2A, the laser line projected by projector 20 has a known angle of incidence relative to the horizontal plane of the scanning table 17 and is viewed from an orthogonal camera. In this regard, the position of the beam 53 in the field of view of cameras 23–30 will be shifted relative to the height of the viewed surface. Because the elevation changes are small in the case described here, the number of scan lines of the CCD camera which "see" the total range of position changes is small relative the total number of horizontal scan lines of a standard camera. The field of view for each camera is sufficiently wide to allow no overlapping of segments for determining the dimensions of any given deposit. Thus, each camera has a dedicated multivision processor unit.

As the printed circuit board is about 3.25 wide the field of view of the cameras 2–30 is established to view the entire board in eight parallel swaths 23A–30A (FIG. 4) respectively. As indicated in FIG. 4, each of the eight camera observes an individual one of the swaths along the scanning table 17 as follows:

C1 ... Camera 23 .. swath no. 1
C2 ... Camera 24 .. swath no. 2
C3 ... Camera 25 .. swath no. 3
C4 ... Camera 26 .. swath no. 4
C5 ... Camera 27 .. swath no. 5
C6 ... Camera 28 .. swath no. 6
C7 ... Camera 29 .. swath no. 7
C8 ... Camera 30 .. swath no. 8

Thus it is possible to impinge the laser line image by segments. Each segment is focused upon the first 60 lines of the CCD camera imager, which read out those 60 lines only. The advantage of the scheme is a reduction of the image acquisition time by a factor of 8. To implement the 60 line acquisition, each of the image acquisition controllers such as controller 18, is held in the reset state until the laser lights are strobed. The image stored on the CCD of the camera is then transmitted to the transformation circuitry 45. After 60 active video scan lines, the acquisition is complete and the acquisition controllers reset their associated cameras such as controller 18 reset camera 23.

Using 512 pixel wide (horizontal) cameras and a 0.5 inch field of view, results in a pixel density of 1000 pixels per inch or 0.001 inch per pixel along the laser line. In order to sample XY space, the laser line must be moved to a new location and an image of that location acquired and processed. The number of 512 lines acquired by the camera can be changed at will in order to accommodate the highest peak expected in the measured object. For example, with a 1 mil per pixel field of view, and 60 degrees from the vertical projected laser line beam, the width of the image field should be no less than 26 pixels in total when the highest peak is expected to 15 mils, and no less than 17 pixels when the highest peak is expected to 10 mils.

The system is implemented such that the repositioning of the laser lines 53 and 54 is a continuous, non-stop operation. The laser strobe is fired at fixed locations along the path flight thus establishing the pixel density in the vertical (relative to the CCD camera) direction. To achieve a "square" pixel array, the strobe would fire once for every 0.001 inch of camera/laser strobe travel. The sampling period is a variable in the system described and is set to optimize throughout versus resolution. That the inherent resolution for any one laser line image is 0.001 inch in both X and Y directions as established by the CCD imager.

In order to sample accurately using a moving camera/ laser, the system 8 utilizes a zero backlash leadscrew drive and servo motor system. The resolution of the servo system is 12,700 counts per inch. The laser strobe fire mechanism is connected directly to a linear encoder 69 which tracks the camera/strobe module. As will be described hereinafter, software pre-calculates the positions (count values) at which a strobe fire is to occur and the strobe fires each time that the position is reached. Between each strobe firing the image is acquired and the camera reset.

The distance between two consecutive lines determines the maximum possible spatial bandwidth measurement along the direction of movement of the stage that can be achieved. The micro steps of the stage holding the 3D object can be varied in order to achieve an optimum sampling rate in the direction of stage movement consistent with the highest spatial frequency of the feature surface and the processing speed available to the sensor. If the highest peak-valley distance of interest is denoted by D, then the sampling in the direction of stage 50 movement should be less than D/2, according to Shannon theorem, in order to avoid aliasing. When looking at the big features of a slow varying surface the sampling distance can be increased, and vice-versa when the feature surface is jittery, an accurate measurement is achieved by having a small sampling rate in the direction of movement. Note that the sampling rate along the line direction is determined by the optics (Field of View) and the resolution of the camera.

Every single line in the 512 long image is processed in gray-scale and not binarized. This makes a big difference on obtaining accurate and repeatable results and permits to measure heights smaller in magnitude than the line width. It also permits to achieve robustness to noise and other artifacts due to shadowing. The gray scale processing consist of calculating the center of gravity of the line position weighed by the image gray scale. Although, the center of gravity weighing scheme was chosen because of its simplicity to calculate and its robustness to various kinds of noises, it should be noted that the processing would work with any function of the gray scale that is convolved with the position (one dimensional convolution).

It is possible to achieve even higher resolution than the width of the laser line. This will be referred to as "Super-Sampling". This is not achievable with other triangulation methods that do not use gray scale processing for the height calculation. Super-Sampling is achievable because it is possible to deconvolve the processed measurements to yield the height for every micro step of the substrate movement. In effect, mathematically, the image processing operation for each line corresponds to a convolution of the gray scale with the position. It is then possible to deconvolve several adjacent lines to yield the position of the height at each pixel position although the width of the laser line is bigger than one pixel.

When the laser line falls on corner where one part of the line is elevated with respect to the remaining part, the gray scale processing still yields an unbiased result of the height measurement, while traditional measurements not using gray scale yield a biased result for the height.

G. PROCESSOR FIRMWARE

Considering now the operation of the CISC microprocessor 44 in greater detail, the CISC microprocessor 44 determines from the RISC processors 34, 36 compressed height data, the area, displacement, and volume measurements of the minute paste deposits disposed on the surface of the printed circuit board 14. In this regard, the CISC microprocessor 44 includes a processing program 200.

Considering now the host processor 43 in greater detail, the host processor 43 is made ready through an automatic boot-up procedure following system power-on. The boot-up software is maintained in a boot rom 79 and on a hard disk drive unit (not shown) forming part of a group of peripheral units indicated generally at 50. All inspection software is auto-loaded during boot-up and on an operator input causes the system to load from disk, the appropriate data base applicable to the substrate configuration to be inspected. Once the system is loaded in remains in a ready condition to sense a trigger signal indicative that a new inspection process is to be commenced.

The host processor 43 is designed to cause flat substrates to be inspected by the station 11. The substrates, such as substrate 14, have small, thin, regularly spaced pads of solder paste have been screen printed. Inspection of any similar surface is readily accomplished. The pads of solder paste may be from 0.007 inch to 0.015 inch thick. The dimension of the base of the pad may vary, but side dimensions of 0.04 inch to 0.10 inch are representative. The base is usually a regular rectangle however, the top surface may be pitted or peaked and may not be parallel with the substrate.

The inspection consists of measuring the base dimensions of every pad (2D) and measuring the elevation from the substrate (3D) of a large number of sample points on each pad surface. The combination of elevation measurements and the base area dimensions provides a measurement of volume of paste (or other material). As a result of locating the edges of each pad, the position of each pad is reported along with the volume data.

The host processor 43 detects the trigger signal from the photo electric sensor. When the trigger signal is received, the host 43 sends a message via a shared memory communications protocol over the shared memory bus. The message is received by the host 43. The host 43 sends messages to all of the other computers in the system to begin their inspection tasks. The first task is to start the servo motor to cause the camera array to begin a scan across the substrate. As the cameras move, pulses are generated from the linear encoder 69. The host 43 counts the pulses, then fires the laser strobe lights at predetermined intervals (approximately 0.003 inches apart). At each firing of the strobe light, each of the eight vision subsystems read the illuminated image from its own camera. The camera data are processed, in parallel by the vision systems. The intermediate results of all the images are stored in the frame buffers.

The host 43 keeps a count of the number of laser strobe firings and thus, can determine when the substrate has been fully sampled. The host 43 stops the scan and signals that the scan phase of the inspection is complete. The host computer requests the inspection results from each of the eight vision subsystems and then assembles those results into a composite analysis of all the pad data; XY location and volume. The next step performed by the host 43 is to check the data against the data base loaded at startup and determine PASS/FAIL information. A PASS result will cause the host 43 to trigger the material handling system to unlock the substrate and to index it from the holder and allow a new substrate in. Scanning is bi-directional to improve throughput of the system. If FAIL is the result, then the host 43 will either stop the entire material handling system and provide an alarm to the operator or, optionally, cause the material handling system to automatically divert the substrate to a reject handler.

In all cases, all results data are logged on a disk. A background program running on the host 43 will create reports in variable formats which are output, on command, to printers, CRT screens, networks, etc. System operators use the reports to determine quality of the process and to make corrections to the process.

The inspection cycle repeats continuously without operator intervention for any one 3D object type.

Considering now the preprocessing firmware of the preprocessing controller 47 in greater detail with reference to FIG. 9, whenever, one of the RISC processors 34, 36 has completed its processing of the data in a given SNAP buffer memory, such as SNAP buffer memory 37 or the CISC processor requires data, a frame buffer sequence is initiated by the firmware of the preprocessing controller 47. In this regard, the firmware starts at instruction box 1602 and proceeds to instruction box 1604.

At instruction box 1604 the RISC address or CISC address is decoded. In this regard, the decoding determines whether RISC processor 34, RISC processor 36 or CISC processor 44 requires data from the frame buffer memories 41 and 42.

The program then proceeds from instruction box 1604 to instruction box 1606 to latch the address and data into the cross bars 62. In this regard, when the address is for frame buffer, the last address and data into the multiplexor cross bars 62. The program then proceeds to a decision instruction box 1608. At decision box 1608 the firmware determines whether the frame buffer memory 41, 42 are busy from other devices. If the frame buffers are busy for other devices, the program proceeds to decision instruction box 1616.

At instruction box 1616 the program waits for a response from the RISC processor to be made available. In this regard, if the RISC processor address is active the program waits. The program then proceeds to decision box 1618 to determine whether the busy signal has fallen. If the signal has not fallen, the program loops on instruction 1618 until the RISC address is no longer active.

When the RISC address is no longer active, the program proceeds to an instruction box 1610.

At instruction box 1610 the frame buffer request for the appropriate RISC or CPU address is set and the program then proceeds to a decision box 1612. At decision box 1612 the program determines whether the frame buffer request has been granted. If the frame buffer request has not been granted, the program loops at decision box 1612.

In the frame buffer grant signal has been received, the program advances to an instruction box 1614.

At instruction 1614 the frame buffer busy signal is set and the set source/destination control on the cross bars 62 is established. The program then advances to a decision box 1620 to check for a read or write cycle to the frame buffer memory 41, 42. If there is no write cycle, the program advances to an instruction box 1624 to set the RISC as source and the frame buffer memory 41, 42 as destination. The program then advances to an instruction box 1626.

If the read signal at the decision box 1620 is active the program advances to an instruction box 1622 to set the data source from memory and sets the RISC processor as the destination. The program advances from box 1622 to box 1626.

At box 1626 a start DRAM memory unit 48 cycle is commenced. In this regard, a RISC enable or CISC 44 enable to the memory unit 48 sequencer to start a memory read/write cycle. DRAM RAS/MUX/CAS cycle is performed on the appropriate frame buffer memory. Write enable signals load data into memory for write cycles, and data load signals into cross bars on the read cycle. The program then proceeds from decision box 1626 to instruction box 1630 and sets the cycle done flag. In this regard, the firmware checks for the DRAM cycle being completed; i.e. data being loaded into memory or data being available from memory. The program then proceeds to a decision box 1632 to check for a data bus lock (another cycle without a releasing request). If the cycle lock is on, the program proceeds to instruction box 1634 and causes a hold request enabled to become active when the data bus lock is active. Another device from accessing the frame buffer memory until the original request is completed in an orderly fashion.

If at decision box 1632 the cycle lock is not on, the program proceeds to an instruction box 1636 to clear the request. After clearing the request at instruction box 1636 the program advances to an instruction box 1638. At instruction box 1638 the program clears the RISC wait response signal so the active RISC microprocessor can terminate its cycle. Also, the frame buffer busy signal is cleared at this time.

From instruction box 1636 the program advances to instruction box 1640 to clear the "cycle done flag." Once the cycle done flag is reset, the program advances to the idle loop at box 1642 to wait to initiate a new frame buffer sequence.

Figure 10A:
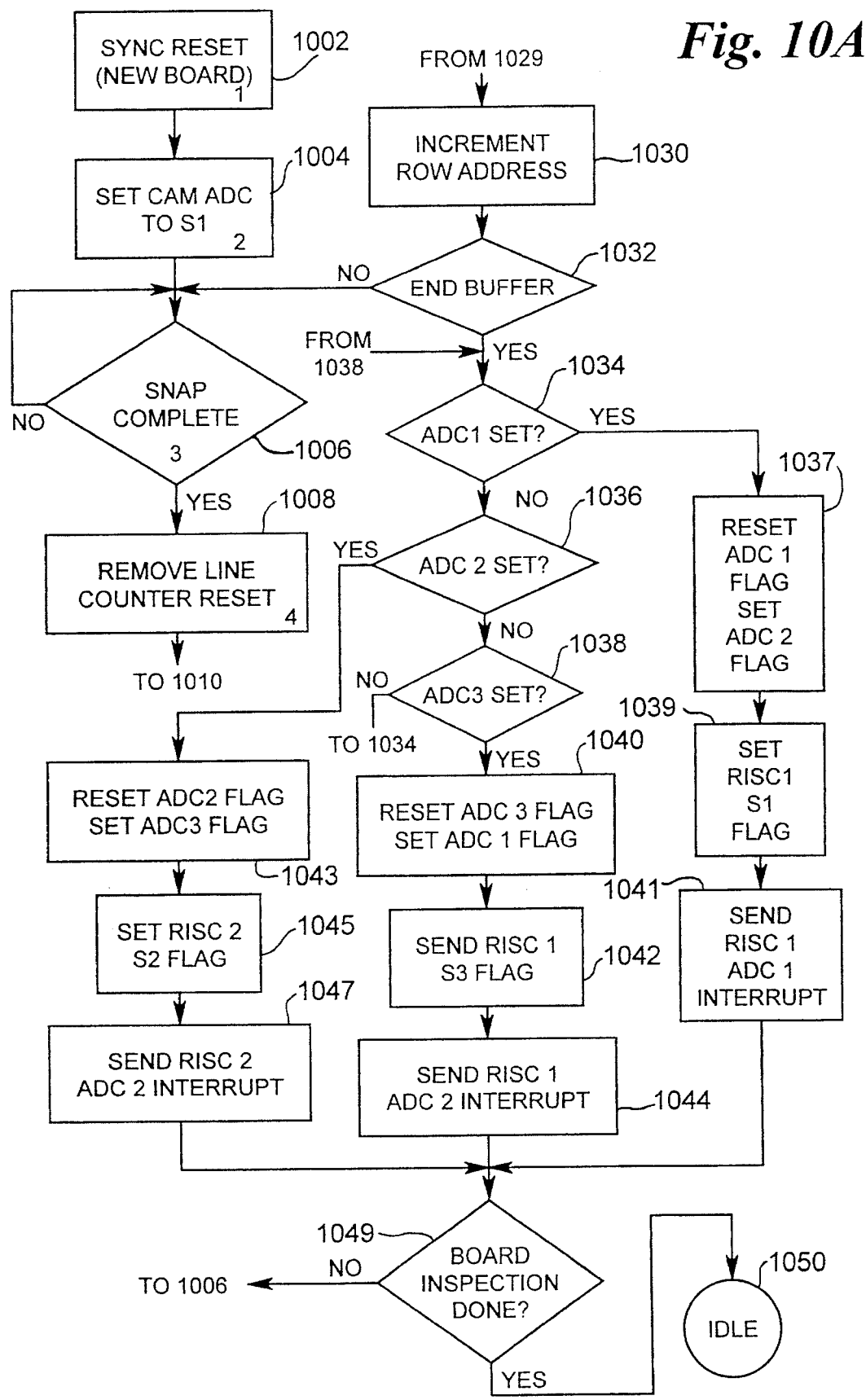
FIGS. 10A–B are flow charts of the image acquisition software for controlling the steps executed by the acquisition controller of FIG. 8A.
Figure 10B:
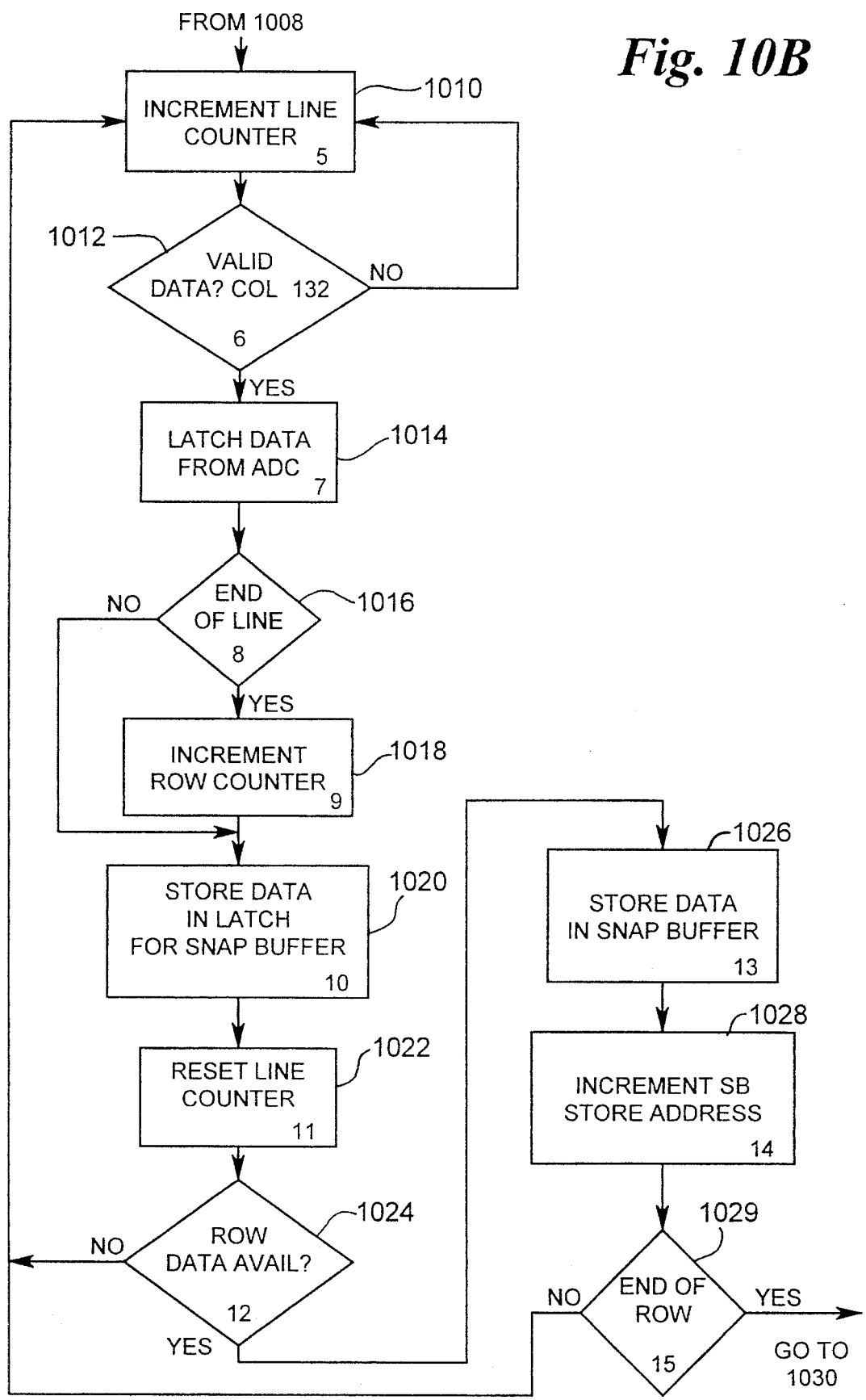

Considering now the image acquisition firmware of the acquisition controller 18 in greater detail with reference to FIGS. 10A and 10B, when the host processor 43 detects a trigger signal, it causes the firmware of the image acquisition controller to proceed to an instruction box 1002 which causes a sync reset signal to be generated.

The firmware then proceeds from instruction box 1002 to instruction box 1004 which sets the flags and pointers to cause the initial data from the analog to digital converter 33 to be stored in snap buffer memory 37. The firmware then proceeds to a decision box 1006 to determine whether the snap has been completed. In this regard, the system software issues a SNAP command once the first projector 20 has been fired. The firmware loops at decision box 1006 until the SNAP command has been received.

Once the SNAP command has been received, the program proceeds to instruction box 1008 which allows the line column or pixel counter to begin counting at the rate of the pixel clock. In this regard, the line counter is reset. The firmware then proceeds to an instruction box 1010 (FIG. 10B) to increment the pixel counter with each pixel clock. The program then proceeds to a decision box 1012 to determine whether the pixel counter has reached column number 132. In this regard, there are 132 pixel clocks of time from the start of the horizontal sync signal until the first active data pixel signal is transmitted from the camera 23. If the column count has not reached 132, the program branches back to the instruction box 1010 to again increment the line counter. This loop is repeated until the counter reaches column 132.

When the counter reaches column 132, the program advances to instruction box 1014 which latches data from the analog to digital converter 33. More particularly, one byte of data from the analog to digital converter 33 is placed into the byte packing register 35. It should be understood that four bytes of data are accumulated before a 32 bit write to the snap buffer 37 is executed. The program then advances to a decision box 1016 to determine whether the end of a line has been reached. In this regard, there are 512 pixels or columns to be digitized to complete a given line. If the line has not been completed, the program proceeds to an instruction box 1020. Instruction box 1020 causes the data in the byte packing register 35 to be stored into the snap buffer memory 37. The program then advances to instruction box 1020 and resets the line counter. The program proceeds from box 1022 to decision box 1024 to determine whether 32 bits of data have been accumulated either from the analog digital converter 33 or from a combination of analog digital converter data and zero fills. If the data has not been accumulated, the program returns to instruction box 1010 and proceeds as previously described.

At decision box 1016 if the end of line has been reached, the program advances to instruction box 1018 which increments the row counter when a line is completed. In this regard, rows are the vertical count and a line is a row.

After the row counter has been incremented, the program advances to instruction box 1020 and proceeds as previously described.

At decision box 1024 if the data has been accumulated, the program advances to instruction box 1026. In instruction box 1026, a write cycle is completed to the snap buffer. In this regard, the data in the byte packing register 35 is addressed via the address control unit 59 into the snap buffer memory 37. The snap buffer address is derived from the current row count and the current pixel (column count).

The program then advances from box 1026 to box 1028 to increment the snap buffer store long word address. The program then proceeds to decision box 1029 to determine whether the complete row has been digitized. If the complete row has not been digitized, the program returns to box number 1010 and proceeds as previously described.

If the complete row has been digitized, the program proceeds to an instruction box 1030 (FIG. 10A). At instruction box 1030 the row address of the snap buffer is incremented. The program then proceeds to a decision box 1032 to determine whether all the camera rows (lines) for one laser line has been digitized. In this regard, the number of rows to be digitized is programmable. In the case of the laser line described herein the specification, 60 rows are required. If the end of buffer has not been digitized, the program branches back to decision box 1006 and proceeds as previously described.

If the end of buffer has been detected (i.e. all camera rows for one laser line have been digitized); the program proceeds to a decision box 1034 to determine whether the ADC1 FLAG has been set. If the ADC1 FLAG has been set, the program proceeds to an instruction box 1037.

At box 1037 the ADC1 FLAG is reset and the ADC2 FLAG is set. This causes the multiplexers to direct the data from the analog digital converter to the next SNAP buffer memory number 37. The program then proceeds to an instruction box 1039 to set the RISC1 FLAG to indicate that the snap buffer memory number 37 is filled and ready for processing. The program then proceeds to send an interrupt signal to the RISC processor 34 to cause it to exit from an idle loop and to initiate processing. In this regard, the RISC processor 34 will first read the flag settings to determine which snap buffer memory data is to be processed. The program then branches to a decision box 1049 to determine whether the board inspection has been completed. In this regard, the system includes an internal timer for the timing of a snap signal within a predetermined period of time. If no more snap signals are received, the program branches to an idle loop 1050 to wait for a new trigger signal from the processor to commence the above described sequence once again. If a new snap signal is received within the prescribed period of time, the program returns to decision box 1006 to determine whether the snap has been completed. In this regard, the program continues as previously described from decision box 1006.

If at decision box 1034 the ADC1 FLAG is not set, the program advances to decision box 1036 to determine whether the ADC2 FLAG has been set. In this regard, if the ADC2 FLAG has been set the program proceeds to an instruction box 1043.

An instruction box 1043, the ADC2 FLAG is reset and the ADC3 FLAG is set. The program then advances from box 1043 to instruction box 1045 to set the RISC 2 flag to indicate to the RISC processor 34 that snap buffer number 2 (S2) memory unit number 38 is filled and ready for processing. The program then proceeds to instruction box 1047 to send the RISC processor 36 an interrupt signal to cause it to exit from an idle loop if it is not processing data and to initiate processing. In this regard, the RISC processor 36 will first read the flag settings to determine which snap buffer memory is to be processed. The program then advances to decision box 1049 and proceeds as previously described.

At decision box 1036 if the ADC2 FLAG is not set the program advances to a decision box 1038 to determine whether the ADC3 FLAG has been set. If the ADC3 FLAG has not been set, the program returns to decision box 1034 and proceeds as previously described.

If the ADC3 FLAG is set at box 1038, the program advances to an instruction box 1040.

At instruction box 1040, the ADC3 FLAG is reset and the ADC1 FLAG is set. The program then advances to box number 1042 to set the RSC processor S3 flag to indicate to the RISC processor 34 that the snap buffer memory number S3 or memory unit 38 is filled or ready for processing. The program then proceeds to instruction box 1044 to send the RISC processor 34 an ADC3 interrupt. From instruction box 1044 the program goes to decision box 1049 and proceeds as previously described.

Considering now the software of the RISC processors 34 and 36 in greater detail, the RISC processor 34 is connected to a RIM memory unit 34A which is downloaded with resident algorithms from the CISC microprocessor 44. In a similar arrangement, the RISC processor 36 is connected to a RIM memory unit 36A which is also downloaded with a resident algorithm from the CISC microprocessor 44. The resident algorithms for RISC processors 34 and 36 are essentially identical only RISC processor algorithm 100 will be described in greater detail with reference to RISC processor 34.

Figure 12:
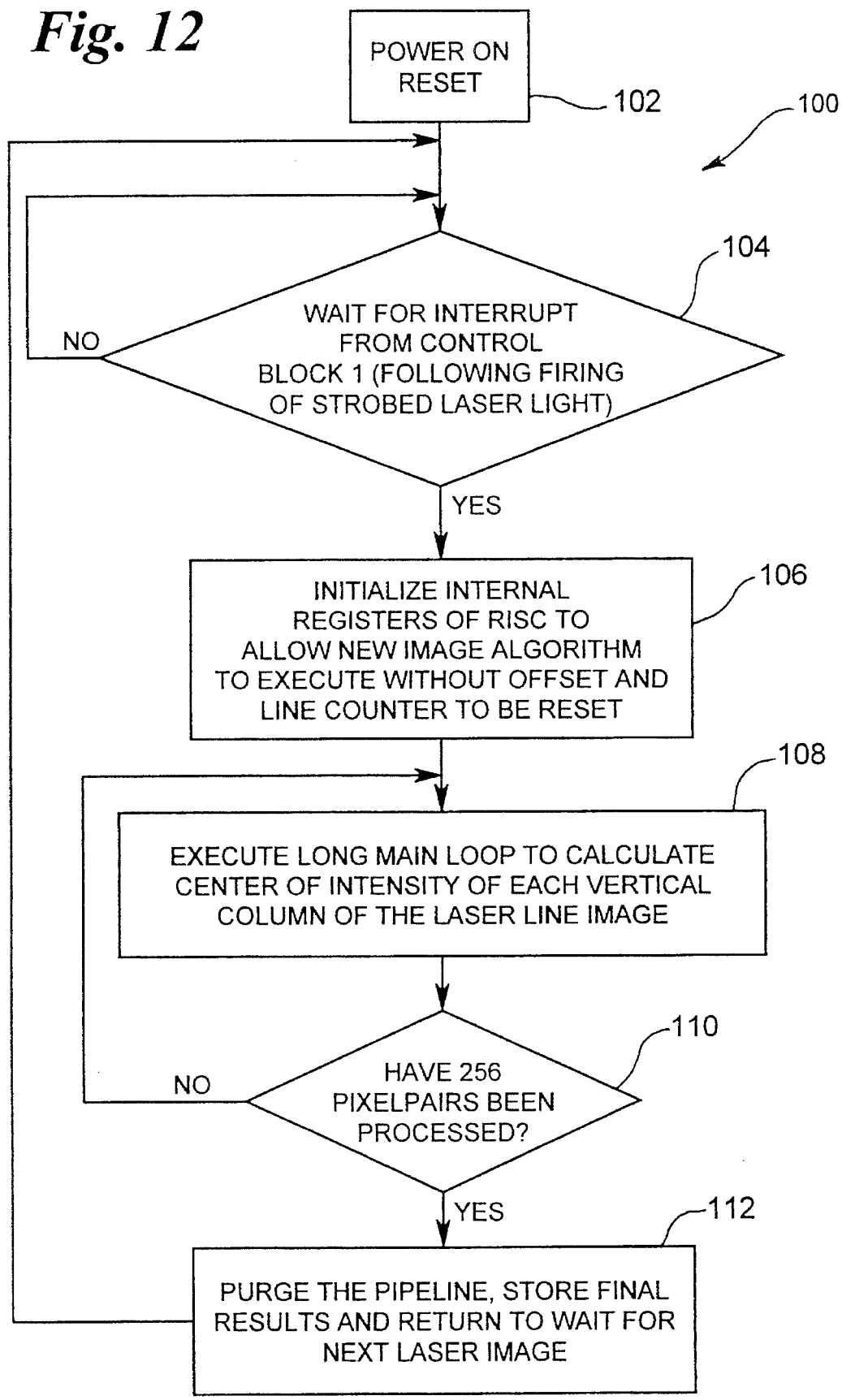
FIG. 12 is a flow chart of the moment software, illustrating the steps executed by the multivision processor unit of FIGS. 8A–B.

Considering now the algorithm 100 in greater detail with reference to FIGS. 12, the algorithm 100 is initialized by a power on reset at instruction box 102. From instruction box 102 the program advances to a decision box 104 to wait for an interrupt from the image acquisition controller 18. In this regard, the interrupt will be generated following the firing or strobing of one of the laser projectors 20, 22.

When the interrupt is received the program advances from decision box 104 to instruction box 106. At instruction box 106 the internal registers of the selected RISC processor are initialized to allow the new image algorithm to execute without offset and to allow the line counter to be reset.

The program proceeds from box 106 to box 108. At box 108 a long main loop subroutine 150 (FIG. 13) is called to calculate the center of intensity of each vertical column of the laser line image. The long main loop subroutine 150 returns to a decision box 110 to determine whether 256 pixel pairs have been processed; i.e. the entire beam. If 256 pixel pairs have not been processed, the program returns to box 108 and calls the main loop subroutine 150 once again.

If 256 pixel pairs have been processed at decision box 110, the program advances to instruction box 112 to purge the data lines and to store the final results. After storing the results, the program returns to box 104 and proceeds as previously described.

Figure 13:
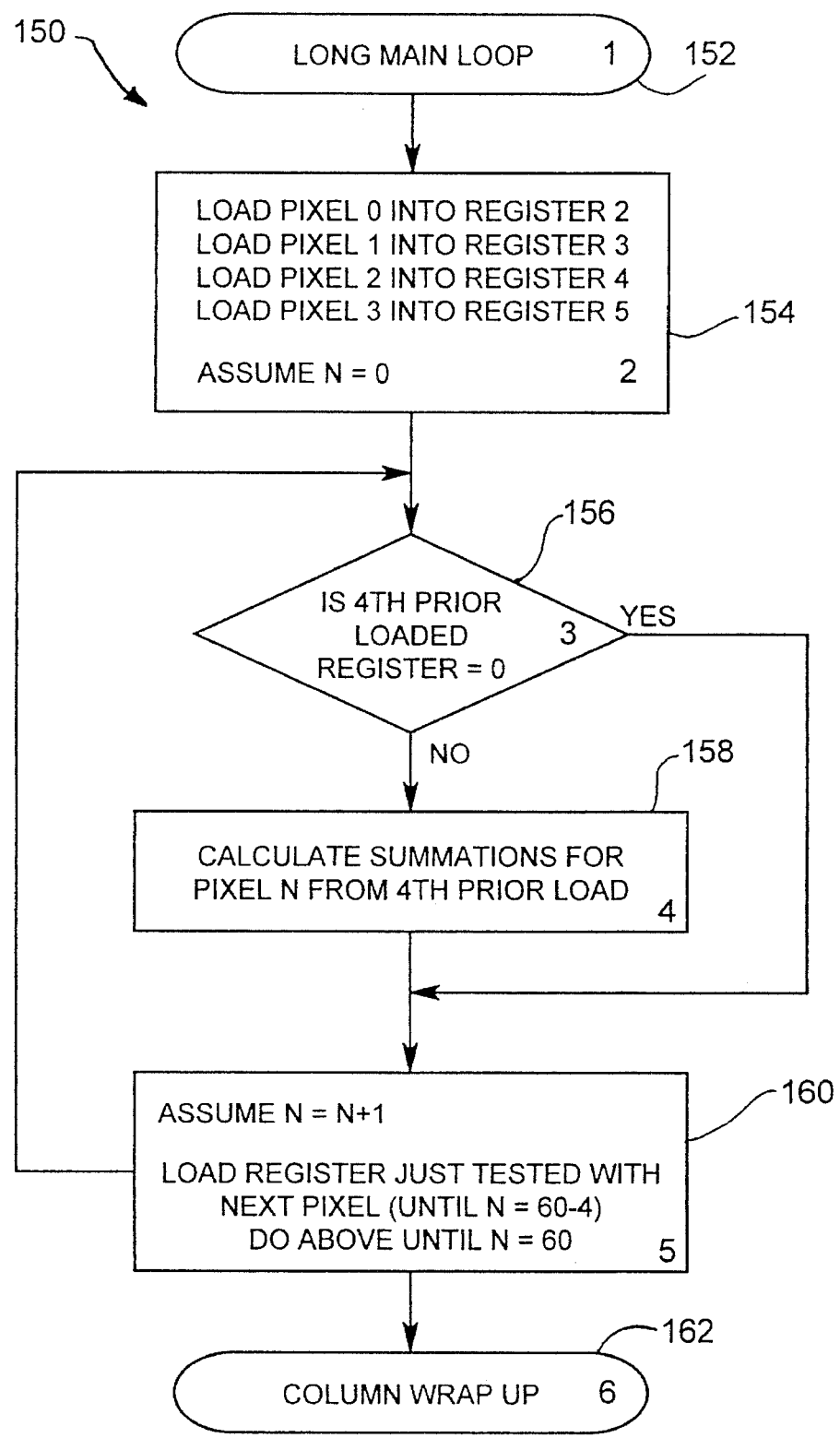
FIG. 13 is a flow chart of the long main loop of the moment software of FIG. 12.

Considering now the long main loop subroutine 150 with reference to FIG. 13, when the long main loop subroutine 150 is called the subroutine start at a call box 152. The program then advances to instruction box 154 which loads pixel information into the internal registers 2–5 of the selected RISC processor. In this regard, the pixel value(s) from row 0 of current column are loaded into register 2, from row 1 into register 3, from row 2 into register 4 and from row 3 into register 5.

The use of the phrase "pixel values" is used as more than one pixel value may be in any given register at one time (if the register is of sufficient size) such that pixels from the same row could be processed simultaneously if "measures" are taken to ensure overflow conditions do not occur.

For example, if the pixel value of row 0 in column 510 is 1OX3F$_{16}$ and the pixel value of row 0 in column 511 is OX10$_{16}$, register 2 could contain a value such as "003F0010."

After loading the pixel values into the internal registers the program proceeds to a decision box 156. If the pixel value is zero, it will not add any value to the summations; thus, flow can bypass summation. In this regard, the program advances to instruction box 160.

If the pixel value is not zero, the program proceeds to instruction box 158 and calculates the summation for pixel n from the 4th prior loaded data in the internal registers. In this regard, the sum of pixel values of every row in a column is a sum register. Sum the (pixel value)×(row n) in another sum register for every pixel value of every row in a column.

The program then proceeds to instruction box 160. Just prior to proceeding to instruction 160, register 2 had just been tested as the 4th prior loaded register. If the pixel value was zero instruction box 158 was not performed. If the pixel value was zero instruction 158 was performed. In either event, register 2 (the register just tested) has been processed and is now available to be loaded with the next pixel value in the pixel row that proceeds the last loaded pixel.

If n does not equal 60 at instruction 160, the program returns to decision instruction 156 and proceeds as previously described. In this regard, the next time the program executes the instruction in box 160, the register will be register 3, then register 4, then register 5, then register 2. This sequence of loading registers 2, 3, 4, 5, 2, 3, 4, 5, etc. is repeated until n=60.

Thus, from one column of pixels, register 2 will process the following rows of pixels: 0, 4, 8, 16, . . . 52, 56. Register 3 will process rows 1, 5, 9, 13, 17, . . . 53, 57; register 4 will process rows 2, 6, 10, 14, 18 . . . 54, 58; and register 5 will process rows 3, 7, 11, 15, 19 . . . 55, 59. If additional pixel values are needed to process a full column, the sequence continues where registers 2, 3, 4, and 5 are loaded with rows 60, 61, 62 and 63 respectively.

After processing all of the pixel values in a full column the program proceeds to a call instruction box 162. At instruction 162 a moment subroutine 175 is called to calculate the center of intensity of the column of processed pixel values. The moment subroutine 175 after completing the center of gravity, causes the results of the division instructions to be stored and exits to call box 152 and proceeds as previously described. This process allows internal parallel processing of the center of gravity for one column of pixel values while the next column is processed.

If the moment subroutine 175 determines all columns have been processed, the subroutine outputs the stored results sequentially into a pre-designated memory location in one of the frame buffer memory units 41, 42. Appendix "C" attached hereto is a listing of the MOMENT subroutine 175. Appendix C is incorporated herein this specification by reference Considering now the geometric algorithm 200 in greater detail with reference to FIG. 11, the CISC microprocessor 44 via a program ROM 88 having the geometric algorithm 200 stored therein, calculates the geometric dimensions of each object observed by camera 23. In this regard, when processed data has been stored in the frame buffer memory units 41 and 42 by the RISC microprocessors 34 and 36, the CISC microprocessor 44 is informed via the memory bus 46.

When the CISC microprocessor 44 is informed processed data is available it commences the geometric algorithm 200 at instruction box 202. At instruction box 202 the algorithm acquires the processed compressed height data stored in one of the designated frame buffer memory units 41, 42. The program then proceeds to instruction box 204.

Because the image data results from the sunset laser beam 53 differs from the sunrise laser beam 54 due their offset base lines, the compressed height data runs in opposite directions. Thus, the row image data in the frame buffer memory units 41, 42 must be translated so the base lines coincide to cause height displacement determinations to be consistent between the sunset and sunrise results. At instruction box 204 the image data results are translated to be consistent. The program then advances to instruction box 206 to determine the base location of the first solder paste deposit, such as the deposit 12. In this regard, the general locations of the solder paste pads are stored in the CAD database 300. The CAD database 300 is used to find the base location of each deposit. At instruction box 206 a large search area surrounding the base location of the pad for deposit 12 is commenced to determine the geometric features of the deposit 12. Thus, the absence of a feature is determined when the compressed height data is relatively low and uniform in the area considered for the base of the object 12. Statistical techniques are used to test for uniformity of height. The program then advances to instruction 208.

Instruction 208 cause the average height of the object 12 to be calculated relative to the determined base of the object. After calculating the average height the program proceeds to instruction box 210.

When in instruction box 210 the program delineates the paste blob or deposit in frame buffer coordinates. In this regard, a location in the image buffer is determined to be in the features if its height (represented in the compressed image data) exceeds significantly the average height of the object 12 determined at instruction 208. The delineation of the deposit is enhanced by the program determining the peripheral edges of the features to a subpixel accuracy. This is accomplished by well known interpolation or by approximation techniques.

Once the paste deposit 12 has been delineated relative to its associated pad, the program branches simultaneously to instruction boxes 212,214 and 218 to calculate the geometric dimensions of the deposit 12.

At instruction box 212 the area of the deposit 12 is calculated by determining the total number of pixels inside the peripheral boundaries established at instruction 210. Once the area is calculated the program advances simultaneously to instruction boxes 216 and 220.

When the program proceeds to instruction 216, the volume of the deposit 12 is calculated by summing the gray scale in each point location inside the feature determined at instruction 210, and correcting the results taking into account the field of view and stage micro-step quantizations. In this regard, it should be understood that instruction box 216 is unable to proceed until the relative height of the deposit 12 has been determined.

At instruction box 214 the relative height of the deposit 12 is determined by averaging the gray scale pixel values inside the feature determined at instruction 210. Once the relative height has been determined the program advances simultaneously to instruction boxes 216 and 220.

Once the area and relative height of the deposit has been determined from instruction box commands 212 and 214 respectively, the volume of the deposit 12 is calculated at instruction box 216 by the process described previously.

Instruction box 218 causes the displacement of the deposit 12 to be calculated. In this regard, the displacement is determined by finding the centroid of the deposit 12 as determined by instruction 210 and then subtracting the centroid from the centroid of the pad on which the deposit 12 is disposed. It should be understood the centroid of the pad was made available from the CAD database 300.

Once the geometric values of the deposit 12 have been calculated via instructions 212, 214, 216 and 218, the results are compared against prestored tolerance value from database 300. Instruction box 220 determines whether the deposit is within tolerance.

After the tolerance have been checked the program advances to an idle mode at 222 waiting for another group of compressed height data to be made available for processing.

Considering now the line sequence control unit 55 in greater detail, the line sequence control unit 55 is a line-grab control PROM. The input to the PROM is the output of a counter (not shown). The counter is set to zero at the beginning of an acquisition sequence (after the strobe has fired) and at the end of every camera line. In other words, the counter counts the number of pixel lines in a camera scan line. The burn pattern of the PROM is such that at predetermined pixel clock counts (which represent the vertical columns in a video matrix) control signals are triggered to cause the storage of ADC output bytes. From the time of the Horizontal Sync (HS) pulse (counter=0) until the first active video time, the output of the PROM indicates "do-nothing." The next 64 counts are also "do-nothing" as the system uses only the center 512 pixels of a 640 wide pixel camera. For the next 512 counts, the PROM constants will indicate that all pixels are to be stored in memory. Following that, the remaining count (until the next HS) will be "do-nothing" outputs. Note that pixel clock is 24 megahertz and that the counter must be a TTL device capable of clocking at that rate. The PROM is a Model AM 270291A.

Considering now the buffer control unit 57 in greater detail, the buffer control unit 57, controls the storage of pixels into a designated SNAP buffer. A SNAP ENABLE input (that is, the strobe has fired indicates the start of a new camera frame. A HSYNC input indicates the start of a new line. As pixel data (8-bits) is received from the analog to digital converter 33, the control unit 57 steers the data to the proper location in the 4-byte or pixel holding buffer. Pixels are stored in the 0 and 2 locations of the buffer leaving the 1 and 3 locations at their reset contents of zero. (0 p 0 p) where 0 is an 8-bit byte equal to zero and p is an 8-bit byte which is the ADC output shifted right by 2 bits. When two bytes have been accumulated in the 4 byte register, the WRITE signal to the SNAP buffer units 37–39 is initiated, the 32-bit write is completed and the SNAP buffer address counter is incremented by 1. After 60 lines have been stored, the END-OF-BUFFER signal is generated and detected by the flag control unit 63.

Considering now the address control unit 59 in greater detail, the address control unit 59, determines which SNAP buffer is to be the destination for the ADC data. It generates outputs which control the port assignment of the MBE between the ADC and SNAP buffers.

Considering now the synchronization control unit 61 in greater detail, the synchronization control unit 61 is a combination counter and EPROM which loops continuously at a rated of 1/16 pixel clock. The output of the EPROM is a series of states which are buffered and transmitted to the camera to control the raster timing. This method facilitates a double readout rate of the camera as well as the 60 line camera frame size. The 1/16 pixel timing resolution is adequate to define the horizontal and vertical sync pulses required by the camera. Timing margins are within specifications. The PROM may be reprogrammed to provide a variety of different sync schemes.

Considering now the error reporting unit 65 in greater detail, the error reporting unit 65 reports sequence errors to the MC68030 processor 44 via a status register which is used to communicate between the RISC processors 34, 36 and the main 68030 CPU. In addition to storing the error code in the status register, an interrupt to processor 44 is generated. An OVERFLOW ERROR indicates that at the time that a SNAP buffer was assigned to the analog to digital converter 33, the RISC which was processing the former image frame in that SNAP buffer was not yet finished (RISC complete flag not set). RISC INPUT BUFFER ERROR indicates that a RISC was trying to access a SNAP buffer which was different from the one assigned to it.

Considering no the flag control unit 63 in greater detail, the flag control unit 63 has a set of six input signals ADC FLAGS1–3, R1 FLAG1 and R1 FLAG2, and END-OF-BUFFER. The OUTPUTS are 6 SET signals which set flip-flops which determine the settings of the MBE at the input and output of the SNAP buffers. That is, the combination of SNAP buffer and RISC is controlled by this block. The END-OF-BUFFER signal allows the control to set the initial conditions for the start of a new set of assignments. If the assignments do not match then that condition is passed to the ERROR unit.

Appendix "D" which is attached hereto is an overall review and summary of an actual visualization system which has been constructed. Appendix D is incorporated herein this specification by reference.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

CONTROL BLOCK 1   Camera/Input Buffer

| | | | | |
|---|---|---|---|---|
| 1   | U70  | LINEGRAB   | (Substitute PAL22V10)        | PROM-AM27S291A |
| 1,2 | U56  | IBWE       | Input Buffer Write Enable    | PAL20L8 |
| 1,2 | U57  | IBWE       | Input Buffer Write Enable    | PAL20L8 |
| 1,2 | U69  | IBWE       | Input Buffer Write Enable    | PAL20L8 |
| 2   | U82  | IBCTL      | Input Buffer Control         | PAL22V10 |
| 2   | U89  | IBDC       | Input Buffer Data Control    | PAL22V10 |
| 2   | U99  | IBDC       | Input Buffer Data Control    | PAL22V10 |
| 2   | U102 | IBDC       | Input Buffer Data Control    | PAL22V10 |
| 3   | U85  | IBAEN      | Input Buffer Address Enable  | PAL22V10 |
| 3   | U87  | IBAC       | Input Buffer Address Control | PAL22V10 |
| 3   | U90  | IBAC       | Input Buffer Address Control | PAL22V10 |
| 3   | U91  | IBAC       | Input Buffer Address Control | PAL22V10 |
| 4   | U54  | SYNC PROM  | Sync Control                 | EPROM27C010 |
| 5   | U73  | RERR       | RISC Error Status            | PAL16R8 |
| 6   | U72  | SETFLAG    | SET RISC 1/2 Buffer Flags    | PAL22V10 |

| | |
|---|---|
| 1 | Line Sequence Control |
| 2 | Buffer Control |
| 3 | Address Control |
| 4 | Sync Control |
| 5 | Error Report |
| 6 | Flag Control Unit |

APPENDIX A

TITLE      ; ADC INPUT BUFFER & LATCH CONTROLS
           ; LOGIC SHEET 10
           ;REV 2 - MADE LSNAP COMBINATION INSTEAD OF REGISTERED
           ;REV 3 - CHG INCROW TO INCRENA INPUT, AND CHGD INCRBADR OUTPUT.

PATTERN    IBCTL

REVISION 3

AUTHOR     DENGLER

COMPANY    IRI VISION

DATE       4 NOV 91

CHIP       IBCTL3          PAL22V10
;          Pattern Name    PAL Type

;pins:  1              2              3              4
       CLOCK48        INCRENA        RESETC_        SYNCRST_

;      5              6              7              8
       SNAPENA_       EOB            ROWSTART       WRITENA

;      9              10             11             12
       DATAENA        ZFILLON2       ZFILLIN3       GND

;      13             14             15             16
       LINEPG         STAGE1         STAGE2         CLRO2_

;      17             18             19             20
       CLR13_         LINECLR_       ROWCLR_        INCRBADR

;      21             22             23             24
       ADCDBEN        LSNAP          HDRIVE_        VCC

;      25     ;FICTIONAL PIN FOR GLOBAL PRESET
       NC

EQUATIONS

/CLRO2_ =
/LINEPG * ZFILLON2

/CLR13_ =
/LINEPG * ZFILLIN3

ADCDBEN =
DATAENA

INCRBADR =
INCRENA * ROWSTART * LSNAP

/LINECLR_ =
/HDRIVE_ * LSNAP * /STAGE1 +
/LSNAP

```
PATTERN     IBCTL

/ROWCLR_ =
/HDRIVE_ * LSNAP * /STAGE1 * /STAGE2 +
/STAGE1 * EOB

LSNAP =
/SNAPENA_ * /STAGE1 * HDRIVE_ +
LSNAP * /EOB

STAGE1 :=
/HDRIVE_

STAGE2 :=
STAGE1 * LSNAP +
STAGE2 * LSNAP
```

```
TITLE       ; INPUT BUFFER & CONTROL
            ; LOGIC SHEET 21 DATA

; CHANGED STATE TABLE TO CORRECT SIGNAL POLARITY
; ADDED ENWR_ OUTPUT

PATTERN     IBDC

REVISION  3

AUTHOR    DENGLER

COMPANY   IRI VISION

DATE      23 OCT 91

CHIP      IBDC3         PAL22V10
;         Pattern Name  PAL Type

;pins:  1              2              3              4
       DCLK40         R1INB_         R2INB_         R1WR_

;      5              6              7              8
       R2WR_          R1FLG          R2FLG          R1WT_

;      9              10             11             12
       R2WT_          CLK20          RESETI_        GND

;      13             14             15             16
       OE_            R1ALI          DS0            DS1

;      17             18             19             20
       IBOED_         R1DOE_         XTRA01_        R2DOE_

;      21             22             23             24
       R2ALI          ENWR_          ADCFLG         VCC

;      25   ;GLOBAL PIN DUMMY ONLY
       NC

EQUATIONS

/XTRA01_ :=
/CLK20 * /ADCFLG * DS1 * /ENWR_ +
/CLK20 * /XTRA01_ * R1DOE_ * R2DOE_ +
/CLK20 * /R1DOE_ +
/CLK20 * /R2DOE_ +
CLK20 * /R1INB_ * /R1FLG * /ADCFLG * /XTRA01_ * R1DOE_ * R2DOE_ +
CLK20 * /R1INB_ * R1FLG * /R2INB_ * /ADCFLG * /XTRA01_ * R1DOE_ * R2DOE_ +
CLK20 * R1INB_ * R1FLG * /XTRA01_ * /R1DOE_ +
CLK20 * R1INB_ * R1FLG * /DS0 * ENWR_ +
CLK20 * R1INB_ * R2INB_ * R2FLG * /ADCFLG * /XTRA01_ * R1DOE_ * R2DOE_ +
CLK20 * R1INB_ * /R2FLG * /ADCFLG * /XTRA01_ * R1DOE_ * R2DOE_ +
CLK20 * /R1FLG * /XTRA01_ * /R1DOE_ +
CLK20 * R2INB_ * R2FLG * /XTRA01_ * /R2DOE_ +
CLK20 * R2INB_ * R2FLG * DS0 * /IBOED_ * ENWR_ +
CLK20 * /R2FLG * /XTRA01_ * /R2DOE_ +
RESETI_ * XTRA01_ * IBOED_ * R1DOE_ * R2DOE_
```

```
PATTERN    IBDC

/DS0 :=
/CLK20 * /DS0 * ENWR_ +
CLK20 * /R1INB_ * R1FLG * /R1WR_ * R2INB_ * /XTRA01_ * R1DOE_ * R2DOE_ +
CLK20 * /R1INB_ * R1FLG * /R1WR_ * /XTRA01_ * /R1DOE_ +
CLK20 * /R1INB_ * R1FLG * /R1WR_ * /DS0 * ENWR_ +
CLK20 * /R1INB_ * R1FLG * /R2INB_ * ADCFLG * /XTRA01_ * R1DOE_ * R2DOE_ +
CLK20 * R1INB_ * R1FLG * /R1WR_ * ADCFLG * /XTRA01_ * R1DOE_ * R2DOE_ +
CLK20 * R1INB_ * R1FLG * R1WR_ * /R2INB_ * ADCFLG * /XTRA01_ * R1DOE_ * R2DOE_ +
CLK20 * /R1FLG * ADCFLG * /XTRA01_ * R1DOE_ * R2DOE_ +
CLK20 * /R1FLG * /DS0 * ENWR_ +
CLK20 * R1FLG * R1WR_ * R2INB_ * ADCFLG * /XTRA01_ * R1DOE_ * R2DOE_ +
CLK20 * /ADCFLG * DS1 * /ENWR_ +
ADCFLG * DS1 * /ENWR_ +
/DS0 * /DS1 * /ENWR_

/DS1 :=
/CLK20 * /IB0ED_ * ENWR_ +
CLK20 * /R1INB_ * R1FLG * /R1WR_ * R2INB_ * /ADCFLG * /XTRA01_ * R1DOE_ * R2DOE_ +
CLK20 * /R1INB_ * R1FLG * /R1WR_ * /XTRA01_ * /R1DOE_ +
CLK20 * /R1INB_ * R1FLG * /R1WR_ * /DS0 * ENWR_ +
CLK20 * R1INB_ * /R2INB_ * R2FLG * /R2WR_ * /ADCFLG * /XTRA01_ * R1DOE_ * R2DOE_ +
CLK20 * /R1FLG * /DS0 * ENWR_ +
CLK20 * /R2INB_ * R2FLG * /R2WR_ * /XTRA01_ * /R2DOE_ +
CLK20 * /R2INB_ * R2FLG * /R2WR_ * DS0 * /IB0ED_ * ENWR_ +
CLK20 * /R2FLG * DS0 * /IB0ED_ * ENWR_ +
/DS1 * /ENWR_

/IB0ED_ :=
/CLK20 * /IB0ED_ * ENWR_ +
CLK20 * /R1INB_ * /R1FLG * ADCFLG * /XTRA01_ * R1DOE_ * R2DOE_ +
CLK20 * /R1INB_ * R1FLG * /R1WR_ * R2INB_ * /XTRA01_ * R1DOE_ * R2DOE_ +
CLK20 * /R1INB_ * R1FLG * /R1WR_ * /XTRA01_ * /R1DOE_ +
CLK20 * /R1INB_ * R1FLG * /R1WR_ * /DS0 * ENWR_ +
CLK20 * /R1INB_ * R1FLG * R1WR_ * R2INB_ * ADCFLG * /XTRA01_ * R1DOE_ * R2DOE_ +
CLK20 * /R1INB_ * R1FLG * /R2INB_ * ADCFLG * /XTRA01_ * R1DOE_ * R2DOE_ +
CLK20 * R1INB_ * /R2INB_ * R2FLG * /R2WR_ * /XTRA01_ * R1DOE_ * R2DOE_ +
CLK20 * R1INB_ * R2INB_ * R2FLG * /R2WR_ * ADCFLG * /XTRA01_ * R1DOE_ * R2DOE_ +
CLK20 * R1INB_ * /R2FLG * ADCFLG * /XTRA01_ * R1DOE_ * R2DOE_ +
CLK20 * R1INB_ * R2FLG * R2WR_ * ADCFLG * /XTRA01_ * R1DOE_ * R2DOE_ +
CLK20 * /R1FLG * /DS0 * ENWR_ +
CLK20 * /R2INB_ * R2FLG * /R2WR_ * /XTRA01_ * /R2DOE_ +
CLK20 * /R2INB_ * R2FLG * /R2WR_ * DS0 * /IB0ED_ * ENWR_ +
CLK20 * /R2FLG * DS0 * /IB0ED_ * ENWR_ +
CLK20 * /ADCFLG * DS1 * /ENWR_ +
ADCFLG * DS1 * /ENWR_ +
/DS1 * /ENWR_

/R1DOE_ :=
/CLK20 * /XTRA01_ * /R1DOE_ +
CLK20 * /R1INB_ * R1FLG * R1WR_ * R2INB_ * /ADCFLG * /XTRA01_ * R1DOE_ * R2DOE_ +
CLK20 * /R1INB_ * R1FLG * R1WR_ * /XTRA01_ * /R1DOE_ +
CLK20 * /R1INB_ * R1FLG * R1WR_ * /DS0 * ENWR_ +
CLK20 * /R1FLG * /XTRA01_ * /R1DOE_ +
XTRA01_ * /R1DOE_
```

PATTERN    IBDC

```
/R2DOE_ :=
/CLK20 * /XTRA01_ * /R2DOE_ +
CLK20 * R1INB_ * /R2INB_ * R2FLG * R2WR_ * /ADCFLG * /XTRA01_ * R1DOE_ * R2DOE_ +
CLK20 * /R2INB_ * R2FLG * R2WR_ * /XTRA01_ * /R2DOE_ +
CLK20 * /R2INB_ * R2FLG * R2WR_ * DS0 * /IB0ED_ * ENWR_ +
CLK20 * /R2FLG * /XTRA01_ * /R2DOE_ +
XTRA01_ * /R2DOE_

/ENWR_ :=
CLK20 * /R1INB_ * /R1FLG * ADCFLG * /XTRA01_ * R1DOE_ * R2DOE_ +
CLK20 * /R1INB_ * R1FLG * /R1WR_ * R2INB_ * /XTRA01_ * R1DOE_ * R2DOE_ +
CLK20 * /R1INB_ * R1FLG * /R1WR_ * /XTRA01_ * /R1DOE_ +
CLK20 * /R1INB_ * R1FLG * /R1WR_ * /DS0 * ENWR_ +
CLK20 * /R1INB_ * R1FLG * R1WR_ * R2INB_ * ADCFLG * /XTRA01_ * R1DOE_ * R2DOE_ +
CLK20 * /R1INB_ * R1FLG * /R2INB_ * ADCFLG * /XTRA01_ * R1DOE_ * R2DOE_ +
CLK20 * R1INB_ * /R2INB_ * R2FLG * /R2WR_ * /XTRA01_ * R1DOE_ * R2DOE_ +
CLK20 * R1INB_ * R2INB_ * R2FLG * /R2WR_ * ADCFLG * /XTRA01_ * R1DOE_ * R2DOE_ +
CLK20 * R1INB_ * /R2FLG * ADCFLG * /XTRA01_ * R1DOE_ * R2DOE_ +
CLK20 * R1INB_ * R2FLG * R2WR_ * ADCFLG * /XTRA01_ * R1DOE_ * R2DOE_ +
CLK20 * /R2INB_ * R2FLG * /R2WR_ * /XTRA01_ * /R2DOE_ +
CLK20 * /R2INB_ * R2FLG * /R2WR_ * DS0 * /IB0ED_ * ENWR_ +
CLK20 * /ADCFLG * DS1 * /ENWR_ +
CLK20 * /DS1 * /ENWR_ +
ADCFLG * DS1 * /ENWR_

R1ALI =
/R1INB_

R2ALI =
/R2INB_

;.input
;CLK20
;R1INB_
;R1FLG
;R1WR_
;R2INB_
;R2FLG
;R2WR_
;RESETI_
;ADCFLG
;R1WT_
;R2WT_

;.output
;XTRA01_
;DS0
;DS1
;IB0ED_
;R1DOE_
;R2DOE_
;ENWR_
;R1ALI
;R2ALI
```

```
    PATTERN   IBDC
;#      .states
;#      STAT_0    XTRA01_   DS0   DS1   IB0ED_   R1D0E_   R2D0E_   ENWR_
;#      STAT_1   /XTRA01_   DS0   DS1   IB0ED_   R1D0E_   R2D0E_   ENWR_
;#      STAT_2    XTRA01_  /DS0   DS1  /IB0ED_   R1D0E_   R2D0E_  /ENWR_
;#      STAT_20   XTRA01_   DS0   DS1   IB0ED_  /R1D0E_   R2D0E_   ENWR_
;#      STAT_21  /XTRA01_   DS0   DS1   IB0ED_  /R1D0E_   R2D0E_   ENWR_
;#      STAT_30   XTRA01_  /DS0  /DS1  /IB0ED_   R1D0E_   R2D0E_  /ENWR_
;#      STAT_31   XTRA01_  /DS0  /DS1  /IB0ED_   R1D0E_   R2D0E_   ENWR_
;#      STAT_40   XTRA01_   DS0   DS1   IB0ED_   R1D0E_  /R2D0E_   ENWR_
;#      STAT_41  /XTRA01_   DS0   DS1   IB0ED_   R1D0E_  /R2D0E_   ENWR_
;#      STAT_50   XTRA01_   DS0  /DS1  /IB0ED_   R1D0E_   R2D0E_  /ENWR_
;#      STAT_51   XTRA01_   DS0  /DS1  /IB0ED_   R1D0E_   R2D0E_   ENWR_

;#      .function
;#      STAT_0    STAT_1    RESETI_
;#      STAT_1    STAT_2    CLK20    ADCFLG
;#      STAT_2    STAT_1   /CLK20   /ADCFLG
;#      STAT_1    STAT_20   CLK20   /R1INB_   R1FLG    R1WR_     R2INB_   /ADCFLG
;#      STAT_1    STAT_30   CLK20   /R1INB_   R1FLG   /R1WR_     R2INB_   /ADCFLG
;#      STAT_1    STAT_40   CLK20    R1INB_  /R2INB_   R2FLG     R2WR_    /ADCFLG
;#      STAT_1    STAT_50   CLK20    R1INB_  /R2INB_   R2FLG    /R2WR_    /ADCFLG
;#      STAT_20   STAT_21  /CLK20
;#      STAT_21   STAT_20   CLK20   /R1INB_   R1FLG    R1WR_
;#      STAT_21   STAT_30   CLK20   /R1INB_   R1FLG   /R1WR_
;#      STAT_21   STAT_1    CLK20    R1INB_   R1FLG
;#      STAT_30   STAT_31  /CLK20
;#      STAT_31   STAT_30   CLK20   /R1INB_   R1FLG   /R1WR_
;#      STAT_31   STAT_20   CLK20   /R1INB_   R1FLG    R1WR_
;#      STAT_31   STAT_1    CLK20    R1INB_   R1FLG
;#      STAT_40   STAT_41  /CLK20
;#      STAT_41   STAT_40   CLK20   /R2INB_   R2FLG    R2WR_
;#      STAT_41   STAT_50   CLK20   /R2INB_   R2FLG   /R2WR_
;#      STAT_41   STAT_1    CLK20    R2INB_   R2FLG
;#      STAT_50   STAT_51  /CLK20
;#      STAT_51   STAT_50   CLK20   /R2INB_   R2FLG   /R2WR_
;#      STAT_51   STAT_40   CLK20   /R2INB_   R2FLG    R2WR_
;#      STAT_51   STAT_1    CLK20    R2INB_   R2FLG
```

```
TITLE       ; ADC INPUT BUFFER ENABLES
            ; LOGIC SHEET 10

PATTERN     IBAEN

REVISION NEW

AUTHOR      DENGLER

COMPANY     IRI VISION

DATE        16 OCT 91

CHIP        IBAEN           PAL22V10
;           Pattern Name    PAL Type

;pins:  1               2               3               4
       CLOCK48         DATAENA         WRITENA         ROWSTART ;      5               6               7               8
       EOB             LDADCPORT       SYNCRST_        RESETC_

;      9               10              11              12
       NC              NC              NC              GND

;      13              14              15              16
       NC              CALI1           CDLI1           CALI2

;      17              18              19              20
       CDLI2           CALI3           CDLI3           XTRA01_

;      21              22              23              24
       ADCFLG1         ADCFLG2         ADCFLG3         VCC

;      25      ;FICTIONAL PIN FOR GLOBAL PRESET
       NC

EQUATIONS

/XTRA01_ :=
/DATAENA * /EOB * /XTRA01_ * ADCFLG2 +
/DATAENA * /EOB * /XTRA01_ * ADCFLG3 +
DATAENA * /EOB * XTRA01_ * ADCFLG1 +
DATAENA * /EOB * ADCFLG2 +
DATAENA * /EOB * ADCFLG3 +
DATAENA * EOB * /XTRA01_ +
/EOB * /XTRA01_ * /ADCFLG2 * /ADCFLG3

/ADCFLG1 :=
/DATAENA * EOB * /XTRA01_ * /ADCFLG2 * /ADCFLG3 +
DATAENA * EOB * /XTRA01_ * ADCFLG3 +
/EOB * /XTRA01_ * ADCFLG3 +
/RESETC_ * /ADCFLG1 * /ADCFLG2 * /ADCFLG3 +
ADCFLG2 +
XTRA01_ * ADCFLG3
```

PATTERN    IBAEN

/ADCFLG2 :=
/DATAENA * EOB * /XTRAO1_ * ADCFLG2 +
DATAENA * EOB * /XTRAO1_ * /ADCFLG2 * /ADCFLG3 +
/EOB * /XTRAO1_ * /ADCFLG2 * /ADCFLG3 +
XTRAO1_ * /ADCFLG2 * /ADCFLG3 +
ADCFLG3

/ADCFLG3 :=
/DATAENA * EOB * /XTRAO1_ * ADCFLG3 +
DATAENA * EOB * /XTRAO1_ * ADCFLG2 +
/EOB * /XTRAO1_ * ADCFLG2 +
/ADCFLG2 * /ADCFLG3 +
XTRAO1_ * ADCFLG2

CALI1 =
ADCFLG1 * WRITENA * DATAENA * ROWSTART

CDLI1 =
ADCFLG1 * WRITENA * DATAENA * ROWSTART

CALI2 =
ADCFLG2 * WRITENA * DATAENA * ROWSTART

CDLI2 =
ADCFLG2 * WRITENA * DATAENA * ROWSTART

CALI3 =
ADCFLG3 * WRITENA * DATAENA * ROWSTART

CDLI3 =
ADCFLG3 * WRITENA * DATAENA * ROWSTART

;.input
;CLOCK48
;DATAENA
;WRITENA
;ROWSTART
;EOB
;LDADCPORT
;SYNCRST_
;RESETC_

;.output
;XTRAO1_
;ADCFLG1
;ADCFLG2
;ADCFLG3

;#     .states
;#     STAT_0    XTRAO1_  /ADCFLG1 /ADCFLG2 /ADCFLG3
;#     STAT_1    XTRAO1_   ADCFLG1 /ADCFLG2 /ADCFLG3
;#     STAT_2   /XTRAO1_   ADCFLG1 /ADCFLG2 /ADCFLG3
;#     STAT_3    XTRAO1_  /ADCFLG1  ADCFLG2 /ADCFLG3
;#     STAT_4   /XTRAO1_  /ADCFLG1  ADCFLG2 /ADCFLG3
;#     STAT_5    XTRAO1_  /ADCFLG1 /ADCFLG2  ADCFLG3
;#     STAT_6   /XTRAO1_  /ADCFLG1 /ADCFLG2  ADCFLG3

```
           PATTERN      IBAEN

;#        .function
     ;#        STAT_0     STAT_1      RESETC_
     ;#        STAT_1     STAT_2      DATAENA  /EOB
     ;#        STAT_2     STAT_3     /DATAENA   EOB
     ;#        STAT_3     STAT_4      DATAENA  /EOB
     ;#        STAT_4     STAT_5     /DATAENA   EOB
     ;#        STAT_5     STAT_6      DATAENA  /EOB
     ;#        STAT_6     STAT_1     /DATAENA   EOB
```

```
TITLE       ; LINE GRAB REPLACEMENT PAL 22V10 FOR
            ; AM27S291A PROLOG TO REPLACEMENT ON LOGIC SHEET 10
PATTERN     LINGRAB

REVISION    2

; CHANGES : REV2 - MAKE DATAEND 2 LESS , CHGD NAMES OF WRITENA TO LATCH, AND
;                  LDADCPORT TO WRITENA. ADDED /PXCLK TO 'LATCH'. KMS

AUTHOR      DENGLER

COMPANY     IRI VISION

DATE        4 NOV 91

CHIP        LINGRAB2      PAL22V10
;           Pattern Name  PAL Type

;pins:  1              2           3           4
        PXLCLK         A6          A5          A4

;       5              6           7           8
        A3             A2          A1          A0

;       9              10          11          12
        DATAENI        WRITENI     T1IN        GND

;       13             14          15          16
        A7             T3          T4          WRITENA

;       17             18          19          20
        DATAEND        LATCH       DATAENA     T2

;       21             22          23          24
        LINEPG         A9          A8          VCC

;       25       ;FICTIONAL PIN FOR GLOBAL PRESET
        NC

EQUATIONS

DATAENA :=
/A9 * /A8 * A7 * A6 * /A5 * /A4 * /A3 * A2 * A1 * /A0 +
DATAENA * /DATAEND

DATAEND :=
A9 * /A8 * A7 * A6 * /A5 * /A4 * /A3 * A2 * A1 * /A0

LATCH :=
DATAENA * A0 * /PXLCLK

WRITENA :=
DATAENA * /A0

T2 :=
/A0

T4 :=
A0
```

TITLE        ; INPUT BUFFER WRITE ENABLE
             ; LOGIC SHEETS 15,16,17

; CHANGES - ADDED ENWR_ INPUT TO ALL /WE_ EQUATIONS
;           REV 2 - REMOVE LBEx'S FROM B1OE AND B2OE EQUATIONS.

PATTERN      IBWE

REVISION     2

AUTHOR       DENGLER

COMPANY      IRI VISION

DATE         22 OCT 91

CHIP         IBWE1          PAL20L8
;            Pattern Name   PAL Type

;pins:  1              2              3              4
       ENWR_           LBE0           LBE1           LBE2

;       5              6              7              8
       LBE3            ADCFLG         R1FLG          R2FLG

;       9              10             11             12
       A15             A24            LRW_           GND

;       13             14             15             16
       CLK20           LDADCPORT      B1CS_          WE0_

;       17             18             19             20
       WE1_            WE2_           WE3_           B1OE_

;       21             22             23             24
       B2OE_           B2CS_          PXLCLK         VCC

EQUATIONS

/WE0_ = LBE0 * /CLK20 * /LRW_ * A24 * R1FLG * /ENWR_
          + LBE0 * /CLK20 * /LRW_ * A24 * R2FLG * /ENWR_
          + LBE0 * /PXLCLK * /LRW_ * A24 * ADCFLG * LDADCPORT * /ENWR_

/WE1_ = LBE1 * /CLK20 * /LRW_ * A24 * R1FLG * /ENWR_
          + LBE1 * /CLK20 * /LRW_ * A24 * R2FLG * /ENWR_
          + LBE1 * /PXLCLK * /LRW_ * A24 * ADCFLG * LDADCPORT * /ENWR_

/WE2_ = LBE2 * /CLK20 * /LRW_ * A24 * R1FLG * /ENWR_
          + LBE2 * /CLK20 * /LRW_ * A24 * R2FLG * /ENWR_
          + LBE2 * /PXLCLK * /LRW_ * A24 * ADCFLG * LDADCPORT * /ENWR_

/WE3_ = LBE3 * /CLK20 * /LRW_ * A24 * R1FLG * /ENWR_
          + LBE3 * /CLK20 * /LRW_ * A24 * R2FLG * /ENWR_
          + LBE3 * /PXLCLK * /LRW_ * A24 * ADCFLG * LDADCPORT * /ENWR_

```
PATTERN     IBWE
 /B1CS_ = ADCFLG * /A15 * A24 + R1FLG * /A15 * A24 + R2FLG * /A15 * A24

/B2CS_ = ADCFLG * A15 * A24 + R1FLG * A15 * A24 + R2FLG * A15 * A24

/B1OE_ =  LRW_ * /A15 * A24
        +  LRW_ * /A15 * A24
        +  LRW_ * /A15 * A24
        +  LRW_ * /A15 * A24

/B2OE_ =  LRW_ * A15 * A24
        +  LRW_ * A15 * A24
        +  LRW_ * A15 * A24
        +  LRW_ * A15 * A24
```

```
TITLE    ; INPUT BUFFER A. ESS CONTROL
         ; LOGIC SHEET 21  ADDRESS

PATTERN   IBAC

REVISION 1A

AUTHOR   DENGLER

COMPANY  IRI VISION

DATE     10 OCT 91

CHIP     IBAC1A          PAL22V10
;        Pattern Name    PAL Type

;pins:  1               2              3              4
        DCLK40          R1BUF          R2BUF          R1FLG ;       5               6              7              8
        R2FLG           R1WAIT_        R2WAIT_        CLK20

;       9               10             11             12
        RESETI_         NC             NC             GND

;       13              14             15             16
        ADCFLG          XTRA01_        AS0            AS1

;       17              18             19             20
        IBOE_           R1ER_          R2ER_          FLOP

;       21              22             23             24
        R2WT_           R1WT_          XTRA02_        VCC

;       25     ;FICTIONAL PIN FOR GLOBAL PRESET
        NC

EQUATIONS

/XTRA01_ :=
/CLK20 * XTRA01_ * /XTRA02_ +
/CLK20 * /XTRA01_ * XTRA02_ +
CLK20 * /R1BUF * /XTRA01_ * XTRA02_ * AS0 +
CLK20 * R1BUF * /R2FLG * /XTRA01_ * XTRA02_ * AS0 +
CLK20 * R1BUF * R2FLG * ADCFLG * /XTRA01_ * XTRA02_ * AS0 +
CLK20 * /R1FLG * /XTRA01_ * XTRA02_ * /AS0 +
CLK20 * R1FLG * /R2BUF * /XTRA01_ * XTRA02_ * /AS0 +
CLK20 * R1FLG * R2BUF * ADCFLG * /XTRA01_ * XTRA02_ * /AS0 +
CLK20 * /XTRA01_ * /XTRA02_

/XTRA02_ :=
CLK20 * R1BUF * /R1FLG * R2BUF * R2FLG * /ADCFLG * IBOE_ * /FLOP +
CLK20 * R1BUF * R1FLG * R2BUF * /R2FLG * /ADCFLG * IBOE_ * /FLOP +
CLK20 * R1BUF * R1FLG * R2BUF * /ADCFLG * XTRA01_ * XTRA02_ * /AS0 * /AS1 * FLOP +
CLK20 * R1BUF * R2BUF * R2FLG * /ADCFLG * XTRA01_ * XTRA02_ * AS0 * R1ER_ * R2ER_ * /IBOE_ * Fl
CLK20 * R1BUF * R2BUF * /ADCFLG * /XTRA01_ * XTRA02_ +
CLK20 * /XTRA02_
```

PATTERN    IBAC

/AS0 :=
CLK20 * /R1FLG * ADCFLG * IB0E_ * /FLOP +
CLK20 * R1FLG * /R2BUF * ADCFLG * IB0E_ * /FLOP +
CLK20 * R1FLG * R2BUF * /R2FLG * IB0E_ * /FLOP +
CLK20 * R1FLG * R2BUF * R2FLG * ADCFLG * IB0E_ * /FLOP +
CLK20 * /ADCFLG * AS1 * R1ER_ * R2ER_ * /IB0E_ +
CLK20 * /XTRA01_ * /XTRA02_ * /AS0 +
ADCFLG * AS1 * R1ER_ * R2ER_ * /IB0E_ +
XTRA01_ * /AS0 * /AS1 +
/XTRA01_ * XTRA02_ * /AS0

/AS1 :=
CLK20 * R1BUF * /R1FLG * R2FLG * /ADCFLG * IB0E_ * /FLOP +
CLK20 * R1FLG * R2BUF * /R2FLG * /ADCFLG * IB0E_ * /FLOP +
CLK20 * /XTRA01_ * /XTRA02_ +
XTRA01_ * /AS1 +
/XTRA01_ * XTRA02_

/R1ER_ :=
CLK20 * /R1BUF * /R1FLG * R2BUF * /ADCFLG * IB0E_ * /FLOP +
CLK20 * /R1ER_

/R2ER_ :=
CLK20 * R1BUF * /R2BUF * /R2FLG * /ADCFLG * IB0E_ * /FLOP +
CLK20 * /R2ER_

/IB0E_ :=
CLK20 * /R1BUF * /R1FLG * R2BUF * IB0E_ * /FLOP +
CLK20 * /R1BUF * /R2BUF * ADCFLG * IB0E_ * /FLOP +
CLK20 * R1BUF * /R1FLG * /R2BUF * IB0E_ * /FLOP +
CLK20 * R1BUF * /R1FLG * R2BUF * R2FLG * /ADCFLG * IB0E_ * /FLOP +
CLK20 * R1BUF * /R1FLG * R2BUF * ADCFLG * IB0E_ * /FLOP +
CLK20 * R1BUF * R1FLG * /R2BUF * /R2FLG * IB0E_ * /FLOP +
CLK20 * R1BUF * R1FLG * /R2BUF * R2FLG * ADCFLG * IB0E_ * /FLOP +
CLK20 * R1FLG * R2BUF * /R2FLG * IB0E_ * /FLOP +
CLK20 * R1FLG * R2BUF * R2FLG * ADCFLG * IB0E_ * /FLOP +
CLK20 * /ADCFLG * AS1 * R1ER_ * R2ER_ * /IB0E_ +
CLK20 * /R1ER_ +
CLK20 * /R2ER_ +
CLK20 * /XTRA01_ * /XTRA02_ +
ADCFLG * AS1 * R1ER_ * R2ER_ * /IB0E_ +
XTRA01_ * /AS1 +
/XTRA01_ * XTRA02_

PATTERN    IBAC

/FLOP :=
/CLK20 * /ADCFLG * AS1 * R1ER_ * R2ER_ * /IBOE_ +
/CLK20 * IBOE_ * /FLOP +
/CLK20 * /R1ER_ +
/CLK20 * /R2ER_ +
/CLK20 * /XTRAO1_ * /XTRAO2_ +
CLK20 * /R1BUF * R1FLG * R2BUF * /ADCFLG * IBOE_ * /FLOP +
CLK20 * /R1BUF * R1FLG * R2BUF * /ADCFLG * XTRAO2_ * /ASO * /AS1 * FLOP +
CLK20 * /R1BUF * /R2BUF * /ADCFLG * IBOE_ * /FLOP +
CLK20 * R1BUF * /R1FLG * R2BUF * /R2FLG * /ADCFLG * IBOE_ * /FLOP +
CLK20 * R1BUF * R1FLG * R2BUF * R2FLG * /ADCFLG * IBOE_ * /FLOP +
CLK20 * R1BUF * /R2BUF * R2FLG * /ADCFLG * IBOE_ * /FLOP +
CLK20 * R1BUF * /R2BUF * R2FLG * /ADCFLG * XTRAO2_ * ASO * R1ER_ * R2ER_ * /IBOE_ * FLOP +
CLK20 * /IBOE_ * /FLOP +
RESETI_ * IBOE_ * FLOP

;.input
;CLK20
;R1BUF
;R1FLG
;R2BUF
;R2FLG
;RESETI_
;ADCFLG
;R1WAIT_
;R2WAIT_

;.output
;XTRAO1_
;XTRAO2_
;ASO
;AS1
;R1ER_
;R2ER_
;IBOE_
;R1WT_
;R2WT_
;FLOP

;#       .states
;#STAT_0   XTRAO1_  XTRAO2_  ASO  AS1  R1ER_  R2ER_  IBOE_  R1WT_  R2WT_  FLOP
;#STAT_1   XTRAO1_  XTRAO2_  ASO  AS1  R1ER_  R2ER_  IBOE_  R1WT_  R2WT_  /FLOP
;#STAT_2   XTRAO1_  XTRAO2_ /ASO  AS1  R1ER_  R2ER_ /IBOE_  R1WT_  R2WT_  FLOP
;#STAT_10  XTRAO1_  XTRAO2_  ASO  AS1 /R1ER_  R2ER_ /IBOE_  R1WT_  R2WT_  FLOP
;#STAT_20  XTRAO1_  XTRAO2_  ASO  AS1  R1ER_ /R2ER_ /IBOE_  R1WT_  R2WT_  FLOP
;#STAT_40  XTRAO1_  XTRAO2_ /ASO /AS1  R1ER_  R2ER_ /IBOE_  R1WT_  R2WT_  /FLOP
;#STAT_41  XTRAO1_  XTRAO2_ /ASO /AS1  R1ER_  R2ER_ /IBOE_  R1WT_  R2WT_  FLOP
;#STAT_50  XTRAO1_ /XTRAO2_ /ASO /AS1  R1ER_  R2ER_ /IBOE_  R1WT_  R2WT_  FLOP
;#STAT_51 /XTRAO1_  XTRAO2_ /ASO /AS1  R1ER_  R2ER_ /IBOE_  R1WT_  R2WT_  FLOP
;#STAT_52 /XTRAO1_ /XTRAO2_ /ASO /AS1  R1ER_  R2ER_ /IBOE_  R1WT_  R2WT_  FLOP
;#STAT_60  XTRAO1_  XTRAO2_  ASO /AS1  R1ER_  R2ER_ /IBOE_  R1WT_  R2WT_  /FLOP
;#STAT_61  XTRAO1_  XTRAO2_  ASO /AS1  R1ER_  R2ER_ /IBOE_  R1WT_  R2WT_  FLOP
;#STAT_70  XTRAO1_ /XTRAO2_  ASO /AS1  R1ER_  R2ER_ /IBOE_  R1WT_  R2WT_  FLOP
;#STAT_71 /XTRAO1_  XTRAO2_  ASO /AS1  R1ER_  R2ER_ /IBOE_  R1WT_  R2WT_  FLOP
;#STAT_72 /XTRAO1_ /XTRAO2_  ASO /AS1  R1ER_  R2ER_ /IBOE_  R1WT_  R2WT_  FLOP

PATTERN    IBAC

```
;#.function
;#STAT_0    STAT_1     RESETI_
;#STAT_1    STAT_2     CLK20    ADCFLG
;#STAT_2    STAT_1     /CLK20   /ADCFLG
;#STAT_1    STAT_10    CLK20    /R1BUF    /R1FLG    R2BUF    /ADCFLG
;#STAT_10   STAT_1     /CLK20
;#STAT_1    STAT_20    CLK20    R1BUF     /R2BUF    /R2FLG   /ADCFLG
;#STAT_20   STAT_1     /CLK20
;#STAT_1    STAT_40    CLK20    /R1BUF    R1FLG     R2BUF    /R2FLG    /ADCFLG
;#STAT_40   STAT_41    /CLK20
;#STAT_41   STAT_40    CLK20    /R1BUF    R1FLG     R2BUF    /ADCFLG
;#STAT_41   STAT_50    CLK20    R1BUF     R1FLG     R2BUF    /ADCFLG
;#STAT_1    STAT_50    CLK20    R1BUF     R1FLG     R2BUF    /R2FLG    /ADCFLG
;#STAT_50   STAT_51    /CLK20
;#STAT_51   STAT_50    CLK20    R1BUF     R1FLG     R2BUF    /ADCFLG
;#STAT_51   STAT_40    CLK20    /R1BUF    R1FLG     R2BUF    /ADCFLG
;#STAT_51   STAT_52    CLK20    R1BUF     /R1FLG    R2BUF    /ADCFLG
;#STAT_52   STAT_1     /CLK20
;#STAT_1    STAT_60    CLK20    R1BUF     /R1FLG    /R2BUF   R2FLG     /ADCFLG
;#STAT_60   STAT_61    /CLK20
;#STAT_61   STAT_60    CLK20    R1BUF     /R2BUF    R2FLG    /ADCFLG
;#STAT_61   STAT_70    CLK20    R1BUF     R2BUF     R2FLG    /ADCFLG
;#STAT_1    STAT_70    CLK20    R1BUF     /R1FLG    R2BUF    R2FLG     /ADCFLG
;#STAT_70   STAT_71    /CLK20
;#STAT_71   STAT_70    CLK20    R1BUF     R2BUF     R2FLG    /ADCFLG
;#STAT_71   STAT_60    CLK20    R1BUF     /R2BUF    R2FLG    /ADCFLG
;#STAT_71   STAT_72    CLK20    R1BUF     R2BUF     /R2FLG   /ADCFLG
;#STAT_72   STAT_1     /CLK20
```

```
#FILENAME: SYNCPROM.PAT   ADDRESS/DATA PATTERN FOR SYNC
                          GENERATOR EPROM, LOC U54 ON SHEET 10.
21 OCTOBER 1991   ADDRESS

REV NEW . INITIAL PATTERN FOR TEST WITH ONLY ONE PAGE. FINAL PATTERN
          WILL USE FULL EPROM WITH FOUR PAGES PROGRAMMED.

ADDRESS INPUTS          ------------------ DATA OUTPUTS
    (BASED ON 48 CLOCKS PER HORIZ LINE       E C - - R - V H
     AND 0.661458 MICROSEC PER CLOCK)        O L - - O - S S
                                             B R - - W -
    ROW NO.     EPROM ADDRESS $HEX   !!      7 6 5 4 3 2 1 0    $VALUE
    ----------------------------------------------------------------------

ROW  0                      000          0 0 1 1 0 1 0 0    34
                                001          0 1 1 1 0 1 0 0    74
                                002          0 1 1 1 0 1 0 0    74
                                003          0 1 1 1 0 1 0 0    74
                                004          0 1 1 1 0 1 0 0    74
                                005          0 1 1 1 0 1 0 0    74
                                006          0 1 1 1 0 1 0 0    74
                                007          0 1 1 1 0 1 0 0    74
                        008 THRU 02F         0 1 1 1 0 1 0 1    75

ROW  1              030 THRU 037         0 1 1 1 0 1 0 0    74
                        038 THRU 05F         0 1 1 1 0 1 0 1    75

ROW  2              060 THRU 067         0 1 1 1 0 1 0 0    74
                        068 THRU 08F         0 1 1 1 0 1 0 1    75

ROW  3              090 THRU 097         0 1 1 1 0 1 0 0    74
                        098 THRU 0BF         0 1 1 1 0 1 0 1    75

ROW  4              0C0 THRU 0C7         0 1 1 1 0 1 0 0    74
                        0C8 THRU 0EF         0 1 1 1 0 1 0 1    75

ROW  5              0F0 THRU 0F7         0 1 1 1 0 1 0 0    74
                        0F8 THRU 11F         0 1 1 1 0 1 0 1    75

ROW  6              120 THRU 127         0 1 1 1 0 1 0 0    74
                        128 THRU 14F         0 1 1 1 0 1 0 1    75

ROW  7              150 THRU 157         0 1 1 1 0 1 0 0    74
                        158 THRU 17F         0 1 1 1 0 1 0 1    75

ROW  8              180 THRU 187         0 1 1 1 0 1 0 0    74
                        188 THRU 1AF         0 1 1 1 0 1 0 1    75

ROW  9              1B0 THRU 1B7         0 1 1 1 0 1 1 0    76
                        1B8 THRU 1DF         0 1 1 1 0 1 1 1    77

ROW 10              1E0 THRU 1E7         0 1 1 1 0 1 1 0    76
                        1E8 THRU 20F         0 1 1 1 0 1 1 1    77

ROW 11              210 THRU 217         0 1 1 1 0 1 1 0    76
                        218 THRU 23F         0 1 1 1 0 1 1 1    77
```

| PATTERN | SYNCPROM | | | |
|---|---|---|---|---|
| ROW 12 | 240 THRU 247 | 0 1 1 1 | 0 1 1 0 | 76 |
| | 248 THRU 26F | 0 1 1 1 | 0 1 1 1 | 77 |
| ROW 13 | 270 THRU 277 | 0 1 1 1 | 0 1 1 0 | 76 |
| | 278 THRU 29F | 0 1 1 1 | 0 1 1 1 | 77 |
| ROW 14 | 2A0 THRU 2A7 | 0 1 1 1 | 0 1 1 0 | 76 |
| | 2A8 THRU 2CF | 0 1 1 1 | 0 1 1 1 | 77 |
| ROW 15 | 2D0 THRU 2D7 | 0 1 1 1 | 0 1 1 0 | 76 |
| | 2D8 THRU 2FF | 0 1 1 1 | 0 1 1 1 | 77 |
| ROW 16 | 300 THRU 307 | 0 1 1 1 | 0 1 1 0 | 76 |
| | 308 THRU 32F | 0 1 1 1 | 0 1 1 1 | 77 |
| ROW 17 | 330 THRU 337 | 0 1 1 1 | 0 1 1 0 | 76 |
| | 338 THRU 35F | 0 1 1 1 | 0 1 1 1 | 77 |
| ROW 18 | 360 THRU 367 | 0 1 1 1 | 0 1 1 0 | 76 |
| | 368 THRU 38F | 0 1 1 1 | 0 1 1 1 | 77 |
| ROW 19 | 390 THRU 397 | 0 1 1 1 | 0 1 1 0 | 76 |
| | 398 THRU 3BF | 0 1 1 1 | 0 1 1 1 | 77 |
| ROW 20 | 3C0 THRU 3C7 | 0 1 1 1 | 1 1 1 0 | 7E |
| | 3C8 THRU 3EF | 0 1 1 1 | 1 1 1 1 | 7F |
| ROW 21 | 3F0 THRU 3F7 | 0 1 1 1 | 1 1 1 0 | 7E |
| | 3F8 THRU 41F | 0 1 1 1 | 1 1 1 1 | 7F |
| ROW 22 | 420 THRU 427 | 0 1 1 1 | 1 1 1 0 | 7E |
| | 428 THRU 44F | 0 1 1 1 | 1 1 1 1 | 7F |
| ROW 23 | 450 THRU 457 | 0 1 1 1 | 1 1 1 0 | 7E |
| | 458 THRU 47F | 0 1 1 1 | 1 1 1 1 | 7F |
| ROW 24 | 480 THRU 487 | 0 1 1 1 | 1 1 1 0 | 7E |
| | 488 THRU 4AF | 0 1 1 1 | 1 1 1 1 | 7F |
| ROW 25 | 4B0 THRU 4B7 | 0 1 1 1 | 1 1 1 0 | 7E |
| | 4B8 THRU 4DF | 0 1 1 1 | 1 1 1 1 | 7F |
| ROW 26 | 4E0 THRU 4E7 | 0 1 1 1 | 1 1 1 0 | 7E |
| | 4E8 THRU 50F | 0 1 1 1 | 1 1 1 1 | 7F |
| ROW 27 | 510 THRU 517 | 0 1 1 1 | 1 1 1 0 | 7E |
| | 518 THRU 53F | 0 1 1 1 | 1 1 1 1 | 7F |
| ROW 28 | 540 THRU 547 | 0 1 1 1 | 1 1 1 0 | 7E |
| | 548 THRU 56F | 0 1 1 1 | 1 1 1 1 | 7F |
| ROW 29 | 570 THRU 577 | 0 1 1 1 | 1 1 1 0 | 7E |
| | 578 THRU 59F | 0 1 1 1 | 1 1 1 1 | 7F |
| ROW 30 | 5A0 THRU 5A7 | 0 1 1 1 | 1 1 1 0 | 7E |
| | 5A8 THRU 5CF | 0 1 1 1 | 1 1 1 1 | 7F |

PATTERN    SYNCPROM

| ROW 31 | 5D0 THRU 5D7 | 0 1 1 1  1 1 1 0 | 7E |
|---|---|---|---|
|        | 5D8 THRU 5FF | 0 1 1 1  1 1 1 1 | 7F |
| ROW 32 | 600 THRU 607 | 0 1 1 1  1 1 1 0 | 7E |
|        | 608 THRU 62F | 0 1 1 1  1 1 1 1 | 7F |
| ROW 33 | 630 THRU 637 | 0 1 1 1  1 1 1 0 | 7E |
|        | 638 THRU 65F | 0 1 1 1  1 1 1 1 | 7F |
| ROW 34 | 660 THRU 667 | 0 1 1 1  1 1 1 0 | 7E |
|        | 668 THRU 68F | 0 1 1 1  1 1 1 1 | 7F |
| ROW 35 | 690 THRU 697 | 0 1 1 1  1 1 1 0 | 7E |
|        | 698 THRU 6BF | 0 1 1 1  1 1 1 1 | 7F |
| ROW 36 | 6C0 THRU 6C7 | 0 1 1 1  1 1 1 0 | 7E |
|        | 6C8 THRU 6EF | 0 1 1 1  1 1 1 1 | 7F |
| ROW 37 | 6F0 THRU 6F7 | 0 1 1 1  1 1 1 0 | 7E |
|        | 6F8 THRU 71F | 0 1 1 1  1 1 1 1 | 7F |
| ROW 38 | 720 THRU 727 | 0 1 1 1  1 1 1 0 | 7E |
|        | 728 THRU 74F | 0 1 1 1  1 1 1 1 | 7F |
| ROW 39 | 750 THRU 757 | 0 1 1 1  1 1 1 0 | 7E |
|        | 758 THRU 77F | 0 1 1 1  1 1 1 1 | 7F |
| ROW 40 | 780 THRU 787 | 0 1 1 1  1 1 1 0 | 7E |
|        | 788 THRU 7AF | 0 1 1 1  1 1 1 1 | 7F |
| ROW 41 | 7B0 THRU 7B7 | 0 1 1 1  1 1 1 0 | 7E |
|        | 7B8 THRU 7DF | 0 1 1 1  1 1 1 1 | 7F |
| ROW 42 | 7E0 THRU 7E7 | 0 1 1 1  1 1 1 0 | 7E |
|        | 7E8 THRU 80F | 0 1 1 1  1 1 1 1 | 7F |
| ROW 43 | 810 THRU 817 | 0 1 1 1  1 1 1 0 | 7E |
|        | 818 THRU 83F | 0 1 1 1  1 1 1 1 | 7F |
| ROW 44 | 840 THRU 847 | 0 1 1 1  1 1 1 0 | 7E |
|        | 848 THRU 86F | 0 1 1 1  1 1 1 1 | 7F |
| ROW 45 | 870 THRU 877 | 0 1 1 1  1 1 1 0 | 7E |
|        | 878 THRU 89F | 0 1 1 1  1 1 1 1 | 7F |
| ROW 46 | 8A0 THRU 8A7 | 0 1 1 1  1 1 1 0 | 7E |
|        | 8A8 THRU 8CF | 0 1 1 1  1 1 1 1 | 7F |
| ROW 47 | 8D0 THRU 8D7 | 0 1 1 1  1 1 1 0 | 7E |
|        | 8D8 THRU 8FF | 0 1 1 1  1 1 1 1 | 7F |
| ROW 48 | 900 THRU 907 | 0 1 1 1  1 1 1 0 | 7E |
|        | 908 THRU 92F | 0 1 1 1  1 1 1 1 | 7F |

PATTERN    SYNCPROM

| | | | |
|---|---|---|---|
| ROW 31 | 5D0 THRU 5D7 | 0 1 1 1  1 1 1 0 | 7E |
|        | 5D8 THRU 5FF | 0 1 1 1  1 1 1 1 | 7F |
| ROW 32 | 600 THRU 607 | 0 1 1 1  1 1 1 0 | 7E |
|        | 608 THRU 62F | 0 1 1 1  1 1 1 1 | 7F |
| ROW 33 | 630 THRU 637 | 0 1 1 1  1 1 1 0 | 7E |
|        | 638 THRU 65F | 0 1 1 1  1 1 1 1 | 7F |
| ROW 34 | 660 THRU 667 | 0 1 1 1  1 1 1 0 | 7E |
|        | 668 THRU 68F | 0 1 1 1  1 1 1 1 | 7F |
| ROW 35 | 690 THRU 697 | 0 1 1 1  1 1 1 0 | 7E |
|        | 698 THRU 6BF | 0 1 1 1  1 1 1 1 | 7F |
| ROW 36 | 6C0 THRU 6C7 | 0 1 1 1  1 1 1 0 | 7E |
|        | 6C8 THRU 6EF | 0 1 1 1  1 1 1 1 | 7F |
| ROW 37 | 6F0 THRU 6F7 | 0 1 1 1  1 1 1 0 | 7E |
|        | 6F8 THRU 71F | 0 1 1 1  1 1 1 1 | 7F |
| ROW 38 | 720 THRU 727 | 0 1 1 1  1 1 1 0 | 7E |
|        | 728 THRU 74F | 0 1 1 1  1 1 1 1 | 7F |
| ROW 39 | 750 THRU 757 | 0 1 1 1  1 1 1 0 | 7E |
|        | 758 THRU 77F | 0 1 1 1  1 1 1 1 | 7F |
| ROW 40 | 780 THRU 787 | 0 1 1 1  1 1 1 0 | 7E |
|        | 788 THRU 7AF | 0 1 1 1  1 1 1 1 | 7F |
| ROW 41 | 7B0 THRU 7B7 | 0 1 1 1  1 1 1 0 | 7E |
|        | 7B8 THRU 7DF | 0 1 1 1  1 1 1 1 | 7F |
| ROW 42 | 7E0 THRU 7E7 | 0 1 1 1  1 1 1 0 | 7E |
|        | 7E8 THRU 80F | 0 1 1 1  1 1 1 1 | 7F |
| ROW 43 | 810 THRU 817 | 0 1 1 1  1 1 1 0 | 7E |
|        | 818 THRU 83F | 0 1 1 1  1 1 1 1 | 7F |
| ROW 44 | 840 THRU 847 | 0 1 1 1  1 1 1 0 | 7E |
|        | 848 THRU 86F | 0 1 1 1  1 1 1 1 | 7F |
| ROW 45 | 870 THRU 877 | 0 1 1 1  1 1 1 0 | 7E |
|        | 878 THRU 89F | 0 1 1 1  1 1 1 1 | 7F |
| ROW 46 | 8A0 THRU 8A7 | 0 1 1 1  1 1 1 0 | 7E |
|        | 8A8 THRU 8CF | 0 1 1 1  1 1 1 1 | 7F |
| ROW 47 | 8D0 THRU 8D7 | 0 1 1 1  1 1 1 0 | 7E |
|        | 8D8 THRU 8FF | 0 1 1 1  1 1 1 1 | 7F |
| ROW 48 | 900 THRU 907 | 0 1 1 1  1 1 1 0 | 7E |
|        | 908 THRU 92F | 0 1 1 1  1 1 1 1 | 7F |

PATTERN    SYSNCPROM

| ROW 49 | 930 THRU 937 | 0 1 1 1 1 1 1 0 | 7E |
|---|---|---|---|
|        | 938 THRU 95F | 0 1 1 1 1 1 1 1 | 7F |
| ROW 50 | 960 THRU 967 | 0 1 1 1 1 1 1 0 | 7E |
|        | 968 THRU 98F | 0 1 1 1 1 1 1 1 | 7F |
| ROW 51 | 990 THRU 997 | 0 1 1 1 1 1 1 0 | 7E |
|        | 998 THRU 9BF | 0 1 1 1 1 1 1 1 | 7F |
| ROW 52 | 9C0 THRU 9C7 | 0 1 1 1 1 1 1 0 | 7E |
|        | 9C8 THRU 9EF | 0 1 1 1 1 1 1 1 | 7F |
| ROW 53 | 9F0 THRU 9F7 | 0 1 1 1 1 1 1 0 | 7E |
|        | 9F8 THRU A1F | 0 1 1 1 1 1 1 1 | 7F |
| ROW 54 | A20 THRU A27 | 0 1 1 1 1 1 1 0 | 7E |
|        | A28 THRU A4F | 0 1 1 1 1 1 1 1 | 7F |
| ROW 55 | A50 THRU A57 | 0 1 1 1 1 1 1 0 | 7E |
|        | A58 THRU A7F | 0 1 1 1 1 1 1 1 | 7F |
| ROW 56 | A80 THRU A87 | 0 1 1 1 1 1 1 0 | 7E |
|        | A88 THRU AAF | 0 1 1 1 1 1 1 1 | 7F |
| ROW 57 | AB0 THRU AB7 | 0 1 1 1 1 1 1 0 | 7E |
|        | AB8 THRU ADF | 0 1 1 1 1 1 1 1 | 7F |
| ROW 58 | AE0 THRU AE7 | 0 1 1 1 1 1 1 0 | 7E |
|        | AE8 THRU B0F | 0 1 1 1 1 1 1 1 | 7F |
| ROW 59 | B10 THRU B17 | 0 1 1 1 1 1 1 0 | 7E |
|        | B18 THRU B3F | 0 1 1 1 1 1 1 1 | 7F |
| ROW 60 | B40 THRU B47 | 0 1 1 1 1 1 1 0 | 7E |
|        | B48 THRU B6F | 0 1 1 1 1 1 1 1 | 7F |
| ROW 61 | B70 THRU B77 | 0 1 1 1 1 1 1 0 | 7E |
|        | B78 THRU B9F | 0 1 1 1 1 1 1 1 | 7F |
| ROW 61 | BA0 THRU BA7 | 0 1 1 1 1 1 1 0 | 7E |
|        | BA8 THRU BCF | 0 1 1 1 1 1 1 1 | 7F |
| ROW 63 D | BD0 THRU BD7 | 0 1 1 1 1 1 1 0 | 7E |
|        | BD8 THRU BFF | 0 1 1 1 1 1 1 1 | 7F |
| ROW 64 | C00 THRU C07 | 0 1 1 1 1 1 1 0 | 7E |
|        | C08 THRU C2F | 0 1 1 1 1 1 1 1 | 7F |
| ROW 65 | C30 THRU C37 | 0 1 1 1 1 1 1 0 | 7E |
|        | C38 THRU C5F | 0 1 1 1 1 1 1 1 | 7F |
| ROW 66 | C60 THRU C67 | 0 1 1 1 1 1 1 0 | 7E |
|        | C68 THRU C8F | 0 1 1 1 1 1 1 1 | 7F |

PATTERN   SYNCPROM

| ROW 67 | C90 THRU C97 | 0 1 1 1  1 1 1 0 | 7E |
|---|---|---|---|
|  | C98 THRU CBF | 0 1 1 1  1 1 1 1 | 7F |
| ROW 68 | CC0 THRU CC7 | 0 1 1 1  1 1 1 0 | 7E |
|  | CC8 THRU CEF | 0 1 1 1  1 1 1 1 | 7F |
| ROW 69 | CF0 THRU CF7 | 0 1 1 1  1 1 1 0 | 7E |
|  | CF8 THRU D1F | 0 1 1 1  1 1 1 1 | 7F |
| ROW 70 | D20 THRU D27 | 0 1 1 1  1 1 1 0 | 7E |
|  | D28 THRU D4F | 0 1 1 1  1 1 1 1 | 7F |
| ROW 71 | D50 THRU D57 | 0 1 1 1  1 1 1 0 | 7E |
|  | D58 THRU D7F | 0 1 1 1  1 1 1 1 | 7F |
| ROW 72 | D80 THRU D87 | 0 1 1 1  1 1 1 0 | 7E |
|  | D88 THRU DAF | 0 1 1 1  1 1 1 1 | 7F |
| ROW 73 | DB0 THRU DB7 | 0 1 1 1  1 1 1 0 | 7E |
|  | DB8 THRU DDF | 0 1 1 1  1 1 1 1 | 7F |
| ROW 74 | DE0 THRU DE7 | 0 1 1 1  1 1 1 0 | 7E |
|  | DE8 THRU E0F | 0 1 1 1  1 1 1 1 | 7F |
| ROW 75 | E10 THRU E17 | 0 1 1 1  1 1 1 0 | 7E |
|  | E18 THRU E3F | 0 1 1 1  1 1 1 1 | 7F |
| ROW 76 | E40 THRU E47 | 0 1 1 1  1 1 1 0 | 7E |
|  | E48 THRU E6F | 0 1 1 1  1 1 1 1 | 7F |
| ROW 77 | E70 THRU E77 | 0 1 1 1  1 1 1 0 | 7E |
|  | E78 THRU E9F | 0 1 1 1  1 1 1 1 | 7F |
| ROW 78 | EA0 THRU EA7 | 0 1 1 1  1 1 1 0 | 7E |
|  | EA8 THRU ECF | 0 1 1 1  1 1 1 1 | 7F |
| ROW 79 | ED0 THRU ED7 | 0 1 1 1  1 1 1 0 | 7E |
|  | ED8 THRU EFF | 0 1 1 1  1 1 1 1 | 7F |
| ROW 80 | F00 | 1 0 1 1  0 1 0 0 | B4 |
|  | F01 | 1 0 1 1  0 1 0 0 | B4 |
|  | F02 | 1 0 1 1  0 1 0 0 | B4 |
|  | F04 | 1 0 1 1  0 1 0 0 | B4 |

ADDRESS $F00 ONWARD START THE NEXT 80-LINE SNAP BUFFER FILL.  NO MORE PROGRAMMING OF THE EEPROM IS REQUIRED FOR THE 80-LINE MODE.

```
TITLE    ; RISC BUFFER Eh..R ERROR
         ; LOGIC SHEETS 10

PATTERN    RERR

REVISION   NEW

AUTHOR     DENGLER

COMPANY    IRI VISION

DATE       9/3/91

CHIP       RERR       PAL16R8

;pins  1          2          3          4          5
       PXLCLK     R1B1_      R1B3_      R2B1_      R2B2_

;      6          7          8          9          10
       R2B3_      OFLOW_     R1B2_      RDSTAT_    GND

;      11         12         13         14         15
       OE_        D22B3ER_   D16_       D17_       D18_

;      16         17         18         19         20
       D19_       D20B1ER_   D21B2ER_   D23OFLO_   VCC

EQUATIONS

; /D16_  ;= NOT DEFINED

/D17_ :=
/R1B3_ * D22B3ER_ +
R1B3_ * /R2B3_ * D22B3ER_ +
/OFLOW_ * D23OFLO_ +
/RDSTAT_ * /D17_ * /D19_ +
/D17_ * D19_

/D18_ :=
/R1B2_ * D21B2ER_ +
R1B2_ * /R2B2_ * D21B2ER_ +
/OFLOW_ * D23OFLO_ +
/RDSTAT_ * /D18_ * /D19_ +
/D18_ * D19_

/D19_ :=
/RDSTAT_ * D17_ * D18_ * D19_ * /D20B1ER_ * /D21B2ER_ * /D22B3ER_ * /D23OFLO_ +
/RDSTAT_ * D17_ * /D19_ +
/RDSTAT_ * /D18_ * D19_ +
/RDSTAT_ * /D17_ * D18_ +
/RDSTAT_ * /D17_ * /D18_ * /D19_
```

```
 PATTERN     RERR

/D20B1ER_ :=
   /R1B1_ * D20B1ER_ +
   R1B1_ * /R2B1_ * D20B1ER_ +
   /RDSTAT_ * D17_ * /D19_ +
   /RDSTAT_ * /D17_ * /D18_ * /D19_ +
   RDSTAT_ * /D18_ * /D19_ +
   D17_ * D18_ * D19_ * /D20B1ER_ +
   /D18_ * D19_ +
   /D17_ * D18_

/D21B2ER_ :=
   /R1B2_ * D21B2ER_ +
   R1B2_ * /R2B2_ * D21B2ER_ +
   /RDSTAT_ * /D18_ * /D19_ +
   RDSTAT_ * /D17_ * /D18_ * /D19_ +
   D18_ * /D21B2ER_ +
   /D18_ * D19_

/D22B3ER_ :=
   /R1B3_ * D22B3ER_ +
   R1B3_ * /R2B3_ * D22B3ER_ +
   /RDSTAT_ * /D17_ * /D19_ +
   RDSTAT_ * /D17_ * /D18_ * /D19_ +
   D19_ * /D22B3ER_ +
   D17_ * /D19_

/D23OFLO_ :=
   /OFLOW_ * D23OFLO_ +
   /RDSTAT_ * /D17_ * /D18_ * /D19_ +
   D17_ * D18_ * D19_ * /D23OFLO_ +
   D17_ * /D19_ +
   /D18_ * D19_ +
   /D17_ * D18_

;.input
   ;R1B1_
   ;R1B2_
   ;R1B3_
   ;R2B1_
   ;R2B2_
   ;R2B3_
   ;OFLOW_
   ;RDSTAT_

;.output
   ;D16
   ;D17_
   ;D18_
   ;D19_
   ;D20B1ER_
   ;D21B2ER_
   ;D22B3ER_
   ;D23OFLO_
```

PATTERN     RERR

```
;#      .states
;#      STAT_1    D17_   D18_   D19_   D20B1ER_ /D21B2ER_ /D22B3ER_ /D23OFLO_
;#      STAT_2    D17_   D18_   D19_  /D20B1ER_ /D21B2ER_ /D22B3ER_ /D23OFLO_
;#      STAT_3    D17_   D18_  /D19_  /D20B1ER_ /D21B2ER_ /D22B3ER_ /D23OFLO_
;#      STAT_11   D17_   D18_   D19_  /D20B1ER_  D21B2ER_ /D22B3ER_ /D23OFLO_
;#      STAT_12   D17_  /D18_   D19_  /D20B1ER_ /D21B2ER_ /D22B3ER_ /D23OFLO_
;#      STAT_13   D17_  /D18_  /D19_  /D20B1ER_ /D21B2ER_ /D22B3ER_ /D23OFLO_
;#      STAT_21   D17_   D18_   D19_  /D20B1ER_ /D21B2ER_  D22B3ER_ /D23OFLO_
;#      STAT_22  /D17_   D18_   D19_  /D20B1ER_ /D21B2ER_ /D22B3ER_ /D23OFLO_
;#      STAT_23  /D17_   D18_  /D19_  /D20B1ER_ /D21B2ER_ /D22B3ER_ /D23OFLO_
;#      STAT_31   D17_   D18_   D19_  /D20B1ER_ /D21B2ER_ /D22B3ER_  D23OFLO_
;#      STAT_32  /D17_  /D18_   D19_  /D20B1ER_ /D21B2ER_ /D22B3ER_ /D23OFLO_
;#      STAT_33  /D17_  /D18_  /D19_  /D20B1ER_ /D21B2ER_ /D22B3ER_ /D23OFLO_

;#      .function
;#      STAT_1    STAT_2   /R1B1_
;#      STAT_1    STAT_2   /R2B1_
;#      STAT_2    STAT_3   /RDSTAT_
;#      STAT_3    STAT_1    RDSTAT_
;#      STAT_11   STAT_12  /R1B2_
;#      STAT_11   STAT_12  /R2B2_
;#      STAT_12   STAT_13  /RDSTAT_
;#      STAT_13   STAT_11   RDSTAT_
;#      STAT_21   STAT_22  /R1B3_
;#      STAT_21   STAT_22  /R2B3_
;#      STAT_22   STAT_23  /RDSTAT_
;#      STAT_23   STAT_21   RDSTAT_
;#      STAT_31   STAT_32  /OFLOW_
;#      STAT_32   STAT_33  /RDSTAT_
;#      STAT_33   STAT_31   RDSTAT_
```

```
TITLE          ;RISC 1 & 2 SET  FLAGS CONTROL, SHEET 10.
               ;REV 2 - ADDED LSNAP TO INPUT FOR SETTING FLAG
               ;HAD TO SWAP PAGE & R2INT PINS

PATTERN    SETFLG

REVISION   2

AUTHOR     DENGLER

COMPANY    IRI VISION

DATE       30 OCT 91

CHIP       SETFLG2      PAL22V10
;          Pattern Name PAL Type

;pins:  1           2           3           4
        CLOCK48     EOB         LSNAP       ADCFLG1

;       5           6           7           8
        ADCFLG2     ADCFLG3     R1FLG1      R1FLG2

;       9           10          11          12
        R1FLG3      R2FLG1      R2FLG2      GND

;       13          14          15          16
        R2FLG3      OFLOW_      R1F1        R1F2

;       17          18          19          20
        R1F3        R2F1        R2F2        R2F3

;       21          22          23          24
        R1INT       PAGE        R2INT       VCC

;       25     ;FICTIONAL PIN FOR GLOBAL PRESET
        NC

EQUATIONS

/R1F1 :=
EOB * ADCFLG1 * /ADCFLG2 * /ADCFLG3 * LSNAP * R1F1 * R2F2 * R2F3 * /PAGE +
EOB * /R1F1

/R1F2 :=
EOB * /ADCFLG1 * ADCFLG2 * /ADCFLG3 * LSNAP * R1F2 * R1F3 * R2F1 * PAGE +
EOB * /R1F2

/R1F3 :=
EOB * /ADCFLG1 * /ADCFLG2 * ADCFLG3 * LSNAP * R1F1 * R2F2 * R2F3 * /PAGE +
EOB * /R1F3

/R2F1 :=
EOB * ADCFLG1 * /ADCFLG2 * /ADCFLG3 * LSNAP * R1F2 * R1F3 * R2F1 * PAGE +
EOB * /R2F1
```

PATTERN    SETFLG

/R2F2 :=
EOB * /ADCFLG1 * ADCFLG2 * /ADCFLG3 * LSNAP * R1F1 * R2F2 * R2F3 * /PAGE +
EOB * /R2F2

/R2F3 :=
EOB * /ADCFLG1 * /ADCFLG2 * ADCFLG3 * LSNAP * R1F2 * R1F3 * R2F1 * PAGE +
EOB * /R2F3

/PAGE :=
/EOB * R1F1 * R2F2 * R2F3 * /PAGE +
EOB * /ADCFLG1 * /ADCFLG2 * ADCFLG3 * LSNAP * R1F2 * R1F3 * R2F1 * PAGE +
EOB * /ADCFLG1 * /ADCFLG2 * ADCFLG3 * /LSNAP * R1F1 * R2F2 * R2F3 * /PAGE +
EOB * /ADCFLG1 * /ADCFLG3 * R1F1 * R2F2 * R2F3 * /PAGE +
EOB * ADCFLG1 * /ADCFLG2 * R1F1 * R2F2 * R2F3 * /PAGE +
EOB * ADCFLG1 * ADCFLG2 * /ADCFLG3 * R1F1 * R2F2 * R2F3 * /PAGE +
EOB * ADCFLG2 * ADCFLG3 * R1F1 * R2F2 * R2F3 * /PAGE +
/R1F1 +
/R2F2 +
/R2F3

R1INT =
/R1F1 + /R1F2 + /R1F3

R2INT =
/R2F1 + /R2F2 + /R2F3

/OFLOW_ =
ADCFLG1 * R1FLG1 * /EOB +
ADCFLG1 * R2FLG1 * /EOB +
ADCFLG2 * R1FLG2 * /EOB +
ADCFLG2 * R2FLG2 * /EOB +
ADCFLG3 * R1FLG3 * /EOB +
ADCFLG3 * R2FLG3 * /EOB

;.input
;EOB
;ADCFLG1
;ADCFLG2
;ADCFLG3
;PAGEFB
;LSNAP

;.output
;R1F1
;R1F2
;R1F3
;R2F1
;R2F2
;R2F3
;PAGE

```
         PATTERN    SETFLG

;#      .states
   ;#      STAT_0    R1F1   R1F2   R1F3    R2F1   R2F2   R2F3  /PAGE
   ;#      STAT_1   /R1F1   R1F2   R1F3    R2F1   R2F2   R2F3  /PAGE
   ;#      STAT_2    R1F1   R1F2   R1F3    R2F1  /R2F2   R2F3  /PAGE
   ;#      STAT_3    R1F1   R1F2  /R1F3    R2F1   R2F2   R2F3   PAGE
   ;#      STAT_4    R1F1   R1F2   R1F3   /R2F1   R2F2   R2F3   PAGE
   ;#      STAT_5    R1F1  /R1F2   R1F3    R2F1   R2F2   R2F3   PAGE
   ;#      STAT_6    R1F1   R1F2   R1F3    R2F1   R2F2  /R2F3  /PAGE
   ;#      STAT_7    R1F1   R1F2   R1F3    R2F1   R2F2   R2F3   PAGE ;#      .function
   ;#      STAT_0   STAT_1    EOB      ADCFLG1 /ADCFLG2 /ADCFLG3 /PAGEFB   LSNAP
   ;#      STAT_1   STAT_0   /EOB
   ;#      STAT_0   STAT_2    EOB     /ADCFLG1  ADCFLG2 /ADCFLG3 /PAGEFB   LSNAP
   ;#      STAT_2   STAT_0   /EOB
   ;#      STAT_0   STAT_3    EOB     /ADCFLG1 /ADCFLG2  ADCFLG3 /PAGEFB   LSNAP
   ;#      STAT_3   STAT_7   /EOB
   ;#      STAT_7   STAT_4    EOB      ADCFLG1 /ADCFLG2 /ADCFLG3  PAGEFB   LSNAP
   ;#      STAT_4   STAT_7   /EOB
   ;#      STAT_7   STAT_5    EOB     /ADCFLG1  ADCFLG2 /ADCFLG3  PAGEFB   LSNAP
   ;#      STAT_5   STAT_7   /EOB
   ;#      STAT_7   STAT_6    EOB     /ADCFLG1 /ADCFLG2  ADCFLG3  PAGEFB   LSNAP
   ;#      STAT_6   STAT_0   /EOB
```

CONTROL BLOCK 2 RISC/Frame Buffers

| U104,U129 | FBREQ | Frame Buffer Request | PAL22V10 |
| U106,U128 | FBGNT | Frame Buffer Grant | PAL22V10 |
| U107,U127 | FBCTL | Frame Buffer Control | PAL22V10 |
| U175,U143 | FBDRAM | Frame Buffer DRAM Sequence | PAL16R8 |
| U198,U218 | FBWEN | Frame Buffer Write Enable | PAL20L8 |
| U177,U197 | PMEMADR | Memory Address MUX | PAL16L8 |
| U216,U217 | PMEMADR | Memory Address MUX | PAL16L8 |
| U176,U174 | FBENA | Frame Buffer Enable | PAL16L8 |

APPENDIX B

```
TITLE       ; FRAME BUFFER REQUEST
            ; LOGIC SHEET 21

;CHANGES:   CHANGE FROM LOW HALF OF DCLK40 TO HIGH HALF OF DCLK40 IN
;           R1ALI AND R2ALI EQUATIONS.
;
;
;
;
;

PATTERN   FBREQ

REVISION  6

AUTHOR    DENGLER

COMPANY   IRI VISION

DATE      15 OCT 91

CHIP      FBREQ6          PAL22V10
;         Pattern Name    PAL Type

;pins:    1               2               3               4
         DCLK40          NC              R1FB_           R1WR_

;        5               6               7               8
         R2FB_           R2WR_           BUSY_           LOCK_

;        9               10              11              12
         DONE_           RESETI_         CLK20           GND

;        13              14              15              16
         OE_             R1ALI           R1LI            R2LI

;        17              18              19              20
         R1REQ_          R2REQ_          R1WT_           XTRA02_

;        21              22              23              24
         R2WT_           XTRA01_         R2ALI           VCC

;        25
         NC

EQUATIONS

/XTRA01_ :=
/CLK20 * /LOCK_ * /DONE_ * /R1LI +
/CLK20 * /LOCK_ * /DONE_ * /XTRA02_ * /R1REQ_ +
/CLK20 * /LOCK_ * /DONE_ * /R2LI +
/CLK20 * /LOCK_ * /DONE_ * /XTRA02_ * /R2REQ_
```

```
PATTERN    FBREQ
/XTRA02_ :=
/CLK20 * R1WR_ * XTRA01_ * XTRA02_ * R1LI * /R1REQ_ +
/CLK20 * R2WR_ * XTRA01_ * XTRA02_ * R2LI * /R2REQ_ +
/CLK20 * LOCK_ * /DONE_ * /R1LI +
/CLK20 * LOCK_ * /DONE_ * /R2LI +
/CLK20 * DONE_ * /XTRA02_ * /R1REQ_ +
/CLK20 * DONE_ * /XTRA02_ * /R2REQ_ +
CLK20 * /LOCK_ * /XTRA02_ * /R1REQ_ +
CLK20 * /LOCK_ * /XTRA02_ * /R2REQ_ +
CLK20 * LOCK_ * DONE_ * /XTRA02_ * /R1REQ_ +
CLK20 * LOCK_ * DONE_ * /XTRA02_ * /R2REQ_ +
LOCK_ * /DONE_ * /XTRA02_ * /R1REQ_ +
LOCK_ * /DONE_ * /XTRA02_ * /R2REQ_

/R1LI :=
/CLK20 * /R1WR_ * XTRA01_ * XTRA02_ * R1LI * /R1REQ_ +
/CLK20 * DONE_ * /R1LI +
CLK20 * /R1LI

/R2LI :=
/CLK20 * /R2WR_ * XTRA01_ * XTRA02_ * R2LI * /R2REQ_ +
/CLK20 * DONE_ * /R2LI +
CLK20 * /R2LI

/R1REQ_ :=
CLK20 * /R1FB_ * BUSY_ * RESETI_ * R1WT_ * R2WT_ +
CLK20 * BUSY_ * XTRA02_ * R1REQ_ * /R1WT_ +
CLK20 * LOCK_ * /DONE_ * /R1LI +
CLK20 * LOCK_ * /DONE_ * /XTRA02_ * /R1REQ_ +
/LOCK_ * /R1LI +
/LOCK_ * /XTRA02_ * /R1REQ_ +
LOCK_ * DONE_ * /R1LI +
LOCK_ * DONE_ * /XTRA02_ * /R1REQ_ +
XTRA02_ * R1LI * /R1REQ_

/R2REQ_ :=
CLK20 * R1FB_ * /R2FB_ * BUSY_ * RESETI_ * R1WT_ * R2WT_ +
CLK20 * BUSY_ * XTRA02_ * R2REQ_ * /R2WT_ +
CLK20 * LOCK_ * /DONE_ * /R2LI +
CLK20 * LOCK_ * /DONE_ * /XTRA02_ * /R2REQ_ +
/LOCK_ * /R2LI +
/LOCK_ * /XTRA02_ * /R2REQ_ +
LOCK_ * DONE_ * /R2LI +
LOCK_ * DONE_ * /XTRA02_ * /R2REQ_ +
XTRA02_ * R2LI * /R2REQ_

/R1WT_ :=
CLK20 * /R1FB_ * R2FB_ * /BUSY_ * RESETI_ * R1WT_ * R2WT_ +
CLK20 * /R1FB_ * BUSY_ * RESETI_ * R1WT_ * R2WT_ +
XTRA02_ * /R1WT_ +
/XTRA02_ * /R1REQ_

/R2WT_ :=
CLK20 * R1FB_ * /R2FB_ * RESETI_ * R1WT_ * R2WT_ +
XTRA02_ * /R2WT_ +
/XTRA02_ * /R2REQ_

R1ALI = /R1FB_ * DCLK40

R2ALI = /R2FB_ * DCLK40
```

```
PATTERN    FBREQ
;#     .states
;#     STAT_1    XTRA01_   XTRA02_   R1LI   R2LI   R1REQ_  R2REQ_  R1WT_   R2WT_
;#     STAT_2    XTRA01_   XTRA02_   R1LI   R2LI   R1REQ_  R2REQ_  /R1WT_  R2WT_
;#     STAT_3    XTRA01_   XTRA02_   R1LI   R2LI   R1REQ_  R2REQ_  R1WT_   /R2WT_
;#     STAT_4    XTRA01_   XTRA02_   R1LI   R2LI  /R1REQ_  R2REQ_  /R1WT_  R2WT_
;#     STAT_5    XTRA01_   XTRA02_  /R1LI   R2LI  /R1REQ_  R2REQ_  /R1WT_  R2WT_
;#     STAT_6    XTRA01_  /XTRA02_   R1LI   R2LI   R1REQ_  R2REQ_  /R1WT_  R2WT_
;#     STAT_7    XTRA01_  /XTRA02_   R1LI   R2LI  /R1REQ_  R2REQ_  /R1WT_  R2WT_
;#     STAT_8   /XTRA01_   XTRA02_   R1LI   R2LI  /R1REQ_  R2REQ_  /R1WT_  R2WT_
;#     STAT_9    XTRA01_   XTRA02_   R1LI   R2LI   R1REQ_ /R2REQ_  R1WT_   /R2WT_
;#     STAT_10   XTRA01_   XTRA02_   R1LI  /R2LI   R1REQ_ /R2REQ_  R1WT_   /R2WT_
;#     STAT_11   XTRA01_  /XTRA02_   R1LI   R2LI   R1REQ_  R2REQ_  R1WT_   /R2WT_
;#     STAT_12   XTRA01_  /XTRA02_   R1LI   R2LI   R1REQ_ /R2REQ_  R1WT_   /R2WT_
;#     STAT_13  /XTRA01_   XTRA02_   R1LI   R2LI   R1REQ_ /R2REQ_  R1WT_   /R2WT_

;#     .function
;#     STAT_1    STAT_2    CLK20    /R1FB_    R2FB_   /BUSY_   RESETI_
;#     STAT_2    STAT_4    CLK20     BUSY_
;#     STAT_1    STAT_3    CLK20     R1FB_   /R2FB_   /BUSY_   RESETI_
;#     STAT_3    STAT_9    CLK20     BUSY_
;#     STAT_1    STAT_4    CLK20    /R1FB_    BUSY_   RESETI_
;#     STAT_4    STAT_5   /CLK20    /R1WR_
;#     STAT_5    STAT_6   /CLK20     LOCK_   /DONE_
;#     STAT_6    STAT_1
;#     STAT_4    STAT_7   /CLK20     R1WR_
;#     STAT_7    STAT_8   /CLK20    /LOCK_   /DONE_
;#     STAT_8    STAT_4
;#     STAT_5    STAT_8   /CLK20    /LOCK_   /DONE_
;#     STAT_7    STAT_6   /CLK20     LOCK_   /DONE_
;#     STAT_1    STAT_9    CLK20     R1FB_   /R2FB_    BUSY_   RESETI_
;#     STAT_9    STAT_10  /CLK20    /R2WR_
;#     STAT_10   STAT_11  /CLK20     LOCK_   /DONE_
;#     STAT_11   STAT_1
;#     STAT_9    STAT_12  /CLK20     R2WR_
;#     STAT_12   STAT_13  /CLK20    /LOCK_   /DONE_
;#     STAT_13   STAT_9
;#     STAT_10   STAT_13  /CLK20    /LOCK_   /DONE_
;#     STAT_12   STAT_11  /CLK20     LOCK_   /DONE_
```

TITLE    ; FRAME BUFFER    ~~HT~~ FBGNT
         ; LOGIC SHEET 21

PATTERN  FBGNT

REVISION 2

AUTHOR   DENGLER

COMPANY  IRI VISION

DATE     10/29/91

CHIP     FBGNT2        PAL22V10
;        Pattern Name  PAL Type

;pins:  1           2           3           4
        DCLK40_     NC          CPUREQ_     CPUGNT_

;       5           6           7           8
        R1GNT_      R2GNT_      R1FB        R2FB

;       9           10          11          12
        STERM_      RESETI_     CLK20       GND

;       13          14          15          16
        OE_         NC          CPUEN_      R1EN_

;       17          18          19          20
        R2EN_       BUSY_       DONE_       XTRA01_

;       21          22          23          24
        XTRA02_     NC          NC          VCC

;       25    DUMB PIN
        NC

EQUATIONS

/XTRA01_ :=
/STERM_ * /R1EN_ +
/STERM_ * /XTRA01_ * /BUSY_ +
/STERM_ * /R2EN_ +
/DONE_

/XTRA02_ :=
/CLK20 * /CPUREQ_ * RESETI_ * XTRA01_ * XTRA02_ * BUSY_ * DONE_ +
CLK20 * /CPUREQ_ * /R1GNT_ * /R2GNT_ * RESETI_ * XTRA01_ * XTRA02_ * BUSY_ * DONE_ +
CLK20 * /CPUREQ_ * R2GNT_ * RESETI_ * XTRA01_ * XTRA02_ * BUSY_ * DONE_ +
CLK20 * CPUREQ_ * /R1GNT_ * RESETI_ * XTRA01_ * XTRA02_ * BUSY_ * DONE_ +
CLK20 * R1GNT_ * /R2GNT_ * RESETI_ * XTRA01_ * XTRA02_ * BUSY_ * DONE_ +
/STERM_ * /CPUEN_ +
/STERM_ * /XTRA02_ * /BUSY_ +
/STERM_ * /R2EN_

```
        PATTERN     FBGNT

/CPUEN_ :=
/CPUGNT_ * R1GNT_ * R2GNT_ * XTRA01_ * XTRA02_ * CPUEN_ * R1EN_ * R2EN_ * /BUSY_ +
STERM_ * /CPUEN_

/R1EN_ :=
CPUGNT_ * /R1GNT_ * R2GNT_ * XTRA01_ * XTRA02_ * CPUEN_ * R1EN_ * R2EN_ * /BUSY_ +
STERM_ * /R1EN_

/R2EN_ :=
CPUGNT_ * R1GNT_ * /R2GNT_ * XTRA01_ * XTRA02_ * CPUEN_ * R1EN_ * R2EN_ * /BUSY_ +
STERM_ * /R2EN_

/BUSY_ :=
/STERM_ * /XTRA02_ * /BUSY_ +
/STERM_ * /XTRA01_ * XTRA02_ * /BUSY_ +
/XTRA02_ * BUSY_ +
XTRA01_ * XTRA02_ * /BUSY_

/DONE_ :=
STERM_ * /XTRA02_ * /BUSY_ +
STERM_ * /XTRA01_ * XTRA02_ * /BUSY_

;#      .states
;#      STAT_1    XTRA01_   XTRA02_   CPUEN_   R1EN_   R2EN_   BUSY_   DONE_
;#      STAT_2    XTRA01_  /XTRA02_   CPUEN_   R1EN_   R2EN_   BUSY_   DONE_
;#      STAT_3    XTRA01_   XTRA02_   CPUEN_   R1EN_   R2EN_  /BUSY_   DONE_
;#      STAT_4    XTRA01_   XTRA02_  /CPUEN_   R1EN_   R2EN_  /BUSY_   DONE_
;#      STAT_5    XTRA01_  /XTRA02_   CPUEN_   R1EN_   R2EN_  /BUSY_   DONE_
;#      STAT_6    XTRA01_   XTRA02_   CPUEN_  /R1EN_   R2EN_  /BUSY_   DONE_
;#      STAT_7   /XTRA01_   XTRA02_   CPUEN_   R1EN_   R2EN_  /BUSY_   DONE_
;#      STAT_8    XTRA01_   XTRA02_   CPUEN_   R1EN_  /R2EN_  /BUSY_   DONE_
;#      STAT_9   /XTRA01_  /XTRA02_   CPUEN_   R1EN_   R2EN_  /BUSY_   DONE_
;#      STAT_10   XTRA01_   XTRA02_   CPUEN_   R1EN_   R2EN_   BUSY_  /DONE_
;#      STAT_11  /XTRA01_   XTRA02_   CPUEN_   R1EN_   R2EN_   BUSY_   DONE_

;#      .function
;#      STAT_1    STAT_2    CLK20    /R1GNT_    RESETI_
;#      STAT_1    STAT_2    CLK20    /R2GNT_    RESETI_
;#      STAT_1    STAT_2   /CPUREQ_  RESETI_
;#      STAT_2    STAT_3
;#      STAT_3    STAT_4   /CPUGNT_   R1GNT_    R2GNT_
;#      STAT_4    STAT_5   /STERM_
;#      STAT_5    STAT_10   STERM_
;#      STAT_10   STAT_11
;#      STAT_11   STAT_1
;#      STAT_3    STAT_6    CPUGNT_  /R1GNT_    R2GNT_
;#      STAT_6    STAT_7   /STERM_
;#      STAT_7    STAT_10   STERM_
;#      STAT_3    STAT_8    CPUGNT_   R1GNT_   /R2GNT_
;#      STAT_8    STAT_9   /STERM_
;#      STAT_9    STAT_10   STERM_
```

TITLE       ; FRAME BUFFER CTRL CONTROL
            ; LOGIC SHEET 21

PATTERN     FBCTL

REVISION 1

AUTHOR      DENGLER

COMPANY     IRI VISION

DATE        9 OCT 91

CHIP        FBCTL1          PAL22V10
;           Pattern Name    PAL Type

;pins:  1           2           3           4
        DCLK40      R1GNT_      R1WR_       R2GNT_

;       5           6           7           8
        R2WR_       CPUGNT_     WRITEB_     DONE_

;       9           10          11          12
        CLK20       RESETI_     NC          GND

;       13          14          15          16
        FBWR_       R1OE_       AS0         AS1

;       17          18          19          20
        AOED_       R2OE_       CPUOE_      DS0

;       21          22          23          24
        DS1         XTRAO1_     OED_        VCC

;       25      ;FICTIONAL PIN FOR GLOBAL PRESET
        NC

EQUATIONS

/XTRAO1_ :=
/CLK20 * /DONE_ * /OED_ +
/CLK20 * /DONE_ * /R1OE_ +
/CLK20 * /DONE_ * /R2OE_ +
/CLK20 * /DONE_ * /CPUOE_ +
/CLK20 * /XTRAO1_ +
CLK20 * /R1GNT_ * /R2GNT_ * /XTRAO1_ +
CLK20 * /R1GNT_ * R2GNT_ * /CPUGNT_ * /XTRAO1_ +
CLK20 * R1GNT_ * /R2GNT_ * /CPUGNT_ * /XTRAO1_ +
CLK20 * R1GNT_ * R2GNT_ * CPUGNT_ * /XTRAO1_ +
RESETI_ * XTRAO1_ * AS0 * AS1

PATTERN    FBCTL

/AOED_ :=
CLK20 * /R1GNT_ * R2GNT_ * CPUGNT_ * /XTRA01_ +
CLK20 * R1GNT_ * /R2GNT_ * CPUGNT_ * /XTRA01_ +
CLK20 * R1GNT_ * R2GNT_ * /CPUGNT_ * /XTRA01_ +
CLK20 * /DONE_ * /OED_ +
CLK20 * /DONE_ * /R1OE_ +
CLK20 * /DONE_ * /R2OE_ +
CLK20 * /DONE_ * /CPUOE_ +
DONE_ * /OED_ +
DONE_ * /R1OE_ +
DONE_ * /R2OE_ +
DONE_ * /CPUOE_ +
/AS1 * R1OE_ * R2OE_ * OED_ +
/AS0 * AS1 * CPUOE_ * OED_

/AS0 :=
CLK20 * /R1GNT_ * R2GNT_ * CPUGNT_ * /XTRA01_ +
CLK20 * R1GNT_ * R2GNT_ * /CPUGNT_ * /XTRA01_ +
CLK20 * /DONE_ * /DS0 +
CLK20 * /DONE_ * /R1OE_ +
CLK20 * /DONE_ * /CPUOE_ +
DONE_ * /DS0 +
DONE_ * /R1OE_ +
DONE_ * /CPUOE_ +
/AS0 * R1OE_ * CPUOE_ * OED_

/AS1 :=
CLK20 * /R1GNT_ * R2GNT_ * CPUGNT_ * /XTRA01_ +
CLK20 * R1GNT_ * /R2GNT_ * CPUGNT_ * /XTRA01_ +
CLK20 * /DONE_ * /DS1 +
CLK20 * /DONE_ * /R1OE_ +
CLK20 * /DONE_ * /R2OE_ +
DONE_ * /DS1 +
DONE_ * /R1OE_ +
DONE_ * /R2OE_ +
/AS1 * R1OE_ * R2OE_ * OED_

/R1OE_ :=
/CLK20 * FBWR_ * /AS0 * /AS1 * R1OE_ * OED_ +
CLK20 * /DONE_ * /R1OE_ +
DONE_ * /R1OE_

/R2OE_ :=
/CLK20 * FBWR_ * AS0 * /AS1 * R2OE_ * OED_ +
CLK20 * /DONE_ * /R2OE_ +
DONE_ * /R2OE_

/CPUOE_ :=
/CLK20 * WRITEB_ * /AS0 * AS1 * CPUOE_ * OED_ +
CLK20 * /DONE_ * /CPUOE_ +
DONE_ * /CPUOE_

/DS0 :=
/CLK20 * /WRITEB_ * /AS0 * AS1 * CPUOE_ * OED_ +
/CLK20 * /FBWR_ * /AS0 * /AS1 * R1OE_ * OED_ +
CLK20 * /DONE_ * /DS0 +
DONE_ * /DS0

PATTERN     FBCTL

/DS1 :=
/CLK20 * /FBWR_ * /AS1 * R1OE_ * R2OE_ * OED_ +
CLK20 * /DONE_ * /DS1 +
DONE_ * /DS1

/OED_ :=
/CLK20 * /WRITEB_ * /AS0 * AS1 * CPUOE_ * OED_ +
/CLK20 * /FBWR_ * /AS1 * R1OE_ * R2OE_ * OED_ +
CLK20 * /DONE_ * /OED_ +
DONE_ * /OED_

;.input
;CLK20
;R1GNT_
;R1WR_
;R2GNT_
;R2WR_
;CPUGNT_
;WRITEB_
;DONE_
;RESETI_
;FBWR_

;.output
;XTRA01_
;AOED_
;AS0
;AS1
;R1OE_
;R2OE_
;CPUOE_
;DS0
;DS1
;OED_

```
;#      .states
;#      STAT_0   XTRA01_   AOED_  AS0   AS1  R1OE_   R2OE_   CPUOE_   DS0   DS1   OED_
;#      STAT_1  /XTRA01_   AOED_  AS0   AS1  R1OE_   R2OE_   CPUOE_   DS0   DS1   OED_
;#      STAT_2   XTRA01_  /AOED_ /AS0  /AS1  R1OE_   R2OE_   CPUOE_   DS0   DS1   OED_
;#      STAT_3   XTRA01_  /AOED_ /AS0  /AS1  R1OE_   R2OE_   CPUOE_  /DS0  /DS1  /OED_
;#      STAT_4   XTRA01_  /AOED_ /AS0  /AS1 /R1OE_   R2OE_   CPUOE_   DS0   DS1   OED_
;#      STAT_5   XTRA01_  /AOED_  AS0  /AS1  R1OE_   R2OE_   CPUOE_   DS0   DS1   OED_
;#      STAT_6   XTRA01_  /AOED_  AS0  /AS1  R1OE_   R2OE_   CPUOE_   DS0  /DS1  /OED_
;#      STAT_7   XTRA01_  /AOED_  AS0  /AS1  R1OE_  /R2OE_   CPUOE_   DS0   DS1   OED_
;#      STAT_8   XTRA01_  /AOED_ /AS0   AS1  R1OE_   R2OE_   CPUOE_   DS0   DS1   OED_
;#      STAT_9   XTRA01_  /AOED_ /AS0   AS1  R1OE_   R2OE_   CPUOE_  /DS0   DS1  /OED_
;#      STAT_10  XTRA01_  /AOED_ /AS0   AS1  R1OE_   R2OE_  /CPUOE_   DS0   DS1   OED_
```

PATTERN     FBCTL

```
;#      .function
;#      STAT_0    STAT_1     RESETI_
;#      STAT_1    STAT_2     CLK20     /R1GNT_    R2GNT_    CPUGNT_
;#      STAT_2    STAT_3     /CLK20    /FBWR_
;#      STAT_3    STAT_1     /CLK20    /DONE_
;#      STAT_2    STAT_4     /CLK20     FBWR_
;#      STAT_4    STAT_1     /CLK20    /DONE_
;#      STAT_1    STAT_5     CLK20      RIGNT_    /R2GNT_   CPUGNT_
;#      STAT_5    STAT_6     /CLK20    /FBWR_
;#      STAT_6    STAT_1     /CLK20    /DONE_
;#      STAT_5    STAT_7     /CLK20     FBWR_
;#      STAT_7    STAT_1     /CLK20    /DONE_
;#      STAT_1    STAT_8     CLK20      RIGNT_    R2GNT_    /CPUGNT_
;#      STAT_8    STAT_9     /CLK20    /WRITEB_
;#      STAT_9    STAT_1     /CLK20    /DONE_
;#      STAT_8    STAT_10    /CLK20     WRITEB_
;#      STAT_10   STAT_1     /CLK20    /DONE_
```

```
7.1  TITLE      ; FRAME BUFFER MEMORY DRAM CONTROL
                ; LOGIC SHEETS 11,12

PATTERN    FBDRAM

REVISION   4B

AUTHOR     DENGLER / SEVERSIKE

COMPANY    IRI VISION

DATE       9 OCT 91

CHIP       FBDRAM4B        PAL16R8
     ;          Pattern Name    PAL Type

;pins: 1              2              3              4              5
            CLK40          CLK20B         AS_            CBREQ_         CPUEN_

;      6              7              8              9              10
            R1EN_          R2EN_          REF            RESETC_        GND

;      11             12             13             14             15
            OE_            RAS_           XTRA02_        CLR_           STERM_

;      16             17             18             19             20
            LEID_          XTRA01_        MUX_           CAS_           VCC

EQUATIONS

/XTRA01_ :=
     /XTRA02_ * CLR_ * LEID_

/XTRA02_ :=
     /MUX_ * STERM_ * /LEID_ +
     /XTRA02_ * /CLR_

/RAS_ :=
     /REF * /CPUEN_ * /CLK20B * /R1EN_ * /R2EN_ * XTRA02_ * MUX_ * /LEID_ +
     /REF * /CPUEN_ * /CLK20B * R2EN_ * XTRA02_ * MUX_ * /LEID_ +
     /REF * CPUEN_ * /CLK20B * /R1EN_ * XTRA02_ * MUX_ * /LEID_ +
     /REF * /CLK20B * R1EN_ * /R2EN_ * XTRA02_ * MUX_ * /LEID_ +
     XTRA01_ * XTRA02_ * /RAS_ * STERM_ * CLR_ +
     RAS_ * /CAS_ +
     /XTRA02_ * LEID_

/MUX_ :=
     CLK20B * XTRA01_ * XTRA02_ * /RAS_ * MUX_ * CLR_ +
     /MUX_ * STERM_ * LEID_ +
     /STERM_ +
     /XTRA01_

/CAS_ :=
     /CLK20B * /RAS_ * /MUX_ * CAS_ +
     /CAS_ * STERM_ * CLR_ +
     RAS_ * /CLR_
```

```
PATTERN    FBDRAM

/STERM_ :=
/CAS_ * CLR_

/CLR_ :=
REF * /CLK20B * XTRA02_ * MUX_ * /LEID_ +
RAS_ * /CLR_

/LEID_ :=
/REF * CPUEN_ * R1EN_ * R2EN_ * XTRA02_ * MUX_ * /LEID_ +
REF * CPUEN_ * CLK20B * R1EN_ * R2EN_ * XTRA02_ * MUX_ * /LEID_ +
/CPUEN_ * CLK20B * XTRA02_ * MUX_ * /LEID_ +
CPUEN_ * CLK20B * /R1EN_ * XTRA02_ * MUX_ * /LEID_ +
CPUEN_ * CLK20B * R1EN_ * /R2EN_ * XTRA02_ * MUX_ * /LEID_ +
RESETC_ * RAS_ * MUX_ * CLR_ * LEID_ +
/STERM_ +
RAS_ * /MUX_ * STERM_ +
/XTRA02_ * /LEID_

;.input
;REF
;CBREQ_
;AS_
;CPUEN_
;CLK20B
;R1EN_
;RESETC_
;R2EN_

;.output
;XTRA01_
;XTRA02_
;RAS_
;MUX_
;CAS_
;STERM_
;CLR_
;LEID_

;#      .states
;#      STAT_0    XTRA01_   XTRA02_  RAS_   MUX_   CAS_   STERM_  CLR_   LEID_
;#      STAT_1    XTRA01_   XTRA02_  RAS_   MUX_   CAS_   STERM_  CLR_   /LEID_
;#      STAT_2    XTRA01_   XTRA02_ /RAS_   MUX_   CAS_   STERM_  CLR_   LEID_
;#      STAT_3    XTRA01_   XTRA02_ /RAS_  /MUX_   CAS_   STERM_  CLR_   LEID_
;#      STAT_4    XTRA01_   XTRA02_ /RAS_  /MUX_  /CAS_   STERM_  CLR_   LEID_
;#      STAT_5    XTRA01_   XTRA02_ /RAS_  /MUX_  /CAS_  /STERM_  CLR_   LEID_
;#      STAT_6    XTRA01_   XTRA02_  RAS_  /MUX_   CAS_  /STERM_  CLR_   /LEID_
;#      STAT_7    XTRA01_   XTRA02_  RAS_  /MUX_   CAS_   STERM_  CLR_   /LEID_
;#      STAT_8    XTRA01_  /XTRA02_  RAS_   MUX_   CAS_   STERM_  CLR_   /LEID_
;#      STAT_20   XTRA01_   XTRA02_  RAS_   MUX_   CAS_   STERM_ /CLR_   LEID_
;#      STAT_21   XTRA01_   XTRA02_  RAS_   MUX_  /CAS_   STERM_ /CLR_   LEID_
;#      STAT_22   XTRA01_   XTRA02_ /RAS_   MUX_  /CAS_   STERM_ /CLR_   LEID_
;#      STAT_23   XTRA01_  /XTRA02_ /RAS_   MUX_  /CAS_   STERM_ /CLR_   LEID_
;#      STAT_24   XTRA01_  /XTRA02_ /RAS_   MUX_   CAS_   STERM_  CLR_   LEID_
;#      STAT_25  /XTRA01_   XTRA02_ /RAS_   MUX_   CAS_   STERM_  CLR_   LEID_
;#      STAT_26   XTRA01_   XTRA02_  RAS_  /MUX_   CAS_   STERM_  CLR_   LEID_
```

```
PATTERN    FBDRAM

;#        .function
;#        STAT_0    STAT_1    RESETC_
;#        STAT_1    STAT_2    /REF      /CPUEN_   /CLK20B
;#        STAT_1    STAT_2    /REF      /CLK20B   /R1EN_
;#        STAT_1    STAT_2    /REF      /CLK20B   /R2EN_
;#        STAT_1    STAT_20   REF       /CLK20B
;#        STAT_2    STAT_3    CLK20B
;#        STAT_3    STAT_4    /CLK20B
;#        STAT_4    STAT_5
;#        STAT_5    STAT_6
;#        STAT_6    STAT_7
;#        STAT_7    STAT_8
;#        STAT_8    STAT_1
;#        STAT_20   STAT_21
;#        STAT_21   STAT_22
;#        STAT_23   STAT_24
;#        STAT_24   STAT_25
;#        STAT_25   STAT_26
;#        STAT_26   STAT_7
```

TITLE       ; FRAME BUFFER MEMORY WRITE ENABLE
            ; LOGIC SHEETS 11,12
            ; CHANGES: REMOVE DBExS FROM FBXWE_ EQUATIONS

PATTERN   FBWEN

REVISION  1

AUTHOR    DENGLER

COMPANY   IRI VISION

DATE      7 OCT 91

CHIP      FBWEN1      PAL20L8
;         Pattern Name  PAL Type

;pins:  1           2           3           4
       FBXA0        FBXA1       FBXDBE0     FBXDBE1

;      5           6           7           8
       FBXDBE2     FBXDBE3     FBXWR_      ASB_

;      9           10          11          12
       WRITE_      SIZE0       SIZE1       GND

;      13          14          15          16
       CLRFXREF_   CPUFBXEN_   FBXWE2_     R2FBXEN_

;      17          18          19          20
       NC          NC          NC          FBXWE0_

;      21          22          23          24
       FBXWE1_     FBXWE3_     R1FBXEN_    VCC

EQUATIONS

/FBXWE3_ = /FBXA0 * /FBXA1 * /FBXWR_ * /ASB_ * /CPUFBXEN_ * CLRFXREF_
         + /R1FBXEN_ * /FBXWR_ * CLRFXREF_
         + /R2FBXEN_ * /FBXWR_ * CLRFXREF_

/FBXWE2_ = /SIZE0 * /FBXA1 * /FBXWR_ * /ASB_ * /CPUFBXEN_ * CLRFXREF_
         + SIZE1 * /FBXA1 * /FBXWR_ * /ASB_ * /CPUFBXEN_ * CLRFXREF_
         + FBXA0 * /FBXA1 * /FBXWR_ * /ASB_ * /CPUFBXEN_ * CLRFXREF_
         + /R1FBXEN_ * /FBXWR_ * CLRFXREF_
         + /R2FBXEN_ * /FBXWR_ * CLRFXREF_

/FBXWE1_ = /FBXA0 * FBXA1 * /FBXWR_ * /ASB_ * /CPUFBXEN_ * CLRFXREF_
         + /SIZE0 * /SIZE1 * /FBXA1 * /FBXWR_ * /ASB_ * /CPUFBXEN_ * CLRFXREF_
         + /SIZE0 * FBXA0 * /FBXA1 * /FBXWR_ * /ASB_ * /CPUFBXEN_ * CLRFXREF_
         + SIZE0 * SIZE1 * /FBXA1 * /FBXWR_ * /ASB_ * /CPUFBXEN_ * CLRFXREF_
         + /R1FBXEN_ * /FBXWR_ * CLRFXREF_
         + /R2FBXEN_ * /FBXWR_ * CLRFXREF_

/FBXWE0_ = /SIZE0 * /SIZE1 * /FBXWR_ * /ASB_ * /CPUFBXEN_ * CLRFXREF_
         + SIZE1 * FBXA1 * /FBXWR_ * /ASB_ * /CPUFBXEN_ * CLRFXREF_
         + FBXA0 * FBXA1 * /FBXWR_ * /ASB_ * /CPUFBXEN_ * CLRFXREF_
         + SIZE0 * SIZE1 * FBXA0 * /FBXWR_ * /ASB_ * /CPUFBXEN_ * CLRFXREF_
         + /R1FBXEN_ * /FBXWR_ * CLRFXREF_
         + /R2FBXEN_ * /FBXWR_ * CLRFXREF_

TITLE PMEMADR -- DRAM ADDRESS-MUX PAL
    ; Logic sheets 3, 11 and 12.

PATTERN PMEMADR

REVISION NEW

AUTHOR DENGLER

COMPANY IRI VISION

DATE 15 AUG 91

CHIP     PMEMADR         PAL16L8
;        Pattern Name    PAL Type

;pins: 1           2           3           4           5
       A7          A8          A9          A10         A11

;      6           7           8           9           10
       A16         A17         A18         A19         GND

;      11          12          13          14          15
       A20         PMA9        A21         MSIZE_      PMMUX_

;      16          17          18          19          20
       PMA5        PMA6        PMA7        PMA8        VCC

EQUATIONS

/PMA5  =   PMMUX_  * /A16  * /MSIZE_
       + /PMMUX_  * /A7
       +  PMMUX_  * /A17 * MSIZE_

/PMA6  =   PMMUX_  * /A17  * /MSIZE_
       + /PMMUX_  * /A8
       +  PMMUX_  * /A18 * MSIZE_

/PMA7  =   PMMUX_  * /A18  * /MSIZE_
       + /PMMUX_  * /A9
       +  PMMUX_  * /A19 * MSIZE_

/PMA8  =   PMMUX_  * /A19  * /MSIZE_
       + /PMMUX_  * /A10
       +  PMMUX_  * /A20 * MSIZE_

/PMA9  =   PMMUX_  * /A20  * /MSIZE_
       + /PMMUX_  * /A11
       +  PMMUX_  * /A21 * MSIZE_

TITLE      ; FRAME BUFFER ~~ENABLE~~ ENABLE
           ; LOGIC SHEETS 11,12

PATTERN    FBENA

REVISION   NEW

AUTHOR     DENGLER

COMPANY    IRI VISION

DATE       8/22/91

CHIP       FBENA       PAL16L8

| ;pins | 1<br>CPUEN_ | 2<br>DLYDS_ | 3<br>WRITEB_ | 4<br>NC | 5<br>DSB_ |
|---|---|---|---|---|---|
| ; | 6<br>R1EN_ | 7<br>NC | 8<br>NC | 9<br>R2EN_ | 10<br>GND |
| ; | 11<br>NC | 12<br>NC | 13<br>NC | 14<br>FBOE_ | 15<br>NC |
| ; | 16<br>NC | 17<br>NC | 18<br>NC | 19<br>NC | 20<br>VCC |

EQUATIONS

/FBOE_ = /CPUEN_ * /DSB_ * WRITEB_ + /R1EN_ + /R2EN_

```
1
2  ;
3  ;
4
5  ;_moment:
6  ;This Motorola MC68100 machine encoded Algorithm purposes to find the moment
7  ; of a video image in a SRAM with the following understandings:
8  ;    1) Pixel 0,0  is at memory 0
9  ;    2) Two Pixel values are stored in one 32 bit Word (4 byte Word)
10 ;    3) The Image is from a 512(0..511) by "n" rows video, thus the code may
11 ;       need to be altered for "n"  .
12 ;
13 ;    4) From assumption "1","2", and "3" above this algo assumes:
14 ;      - a) a new row on a video column starts at Modulo 400 bytes
15 ;         b) vertically adjacent pixels are Modulo 400 bytes apart
16 ;         c) currently the code assumes "n" = 29 (i.e 0 to 28)
17 ;
18 ;    5) The Pixel values put in the SRAM by an AD Convertor are
19 ;       scaled to an appropriately small value so an overflow
20 ;       will not occur, otherwise it is not detected
21 ;    6) The Algo is optimized if the above scale is performed
22 ;       and if the AD Convertor converts "insignificant" low
23 ;       values to zero to quickly branch and load
24 ;    7) Currently the Algo writes the result for a column
25 ;       back to row 0 of that column
26 ;
27 ;
28 ;Assumed Pixel Orientation from Video Image
29 ;For [r,c] : Where r= "to the horizontal row" and  c = "to the vertical column"
30 ; |-----------------------------------------------------------------------|
31 ; | [0,0] ; [0,1] ; [0,2] ; [0,3] ; [0,4] ; [0,5] . . . . . [0,511] |
32 ; | [1,0] ; [1,1] ; [1,2] ; [1,3] ; [1,4] ; [1,5] . . . . . [1,511] |
33 ; | [2,0] ; [2,1] ; [2,2] ; [2,3] ; [2,4] ; [2,5] . . . . . [2,511] |
34 ; | [3,0] ; [3,1] ; [3,2] ; [3,3] ; [3,4] ; [3,5] . . . . . [3,511] |
35 ; | [4,0] ; [4,1] ; [4,2] ; [4,3] ; [4,4] ; [4,5] . . . . . [4,511] |
36 ; | [5,0] ; [5,1] ; [5,2] ; [5,3] ; [5,4] ; [5,5] . . . . . [5,511] |
37 ; |   .   ;   .   ;   .   ;   .   ;   .   ;   .   . . . . .   .    |
38 ; |   .   ;   .   ;   .   ;   .   ;   .   ;   .   . . . . .   .    |
39 ; |   .   ;   .   ;   .   ;   .   ;   .   ;   .   . . . . .   .    |
40 ; |   .   ;   .   ;   .   ;   .   ;   .   ;   .   . . . . .   .    |
41 ; |   .   ;   .   ;   .   ;   .   ;   .   ;   .   . . . . .   .    |
42 ; |   .   ;   .   ;   .   ;   .   ;   .   ;   .   . . . . .   .    |
43 ; | [n,0] ; [n,1] ; [n,2] ; [n,3] ; [n,4] ; [n,5] . . . . . [n,511] |
44 ; |-----------------------------------------------------------------------|
45 ; for "n" video rows where n < 59
46 ;
47 ;
48 ;
49 ;
50 ;
51 ;
```

APPENDIX C

```
61 ;
62 ;
63 ;To find the moment for n horizontal video rows
64 ;The above Pixel Image should map onto the 32 bit WORD ADDRESSES of
65 ;SRAM as follows in HEXIDECIMAL:
66 ; !-----------------------------------------------------------------!
67 ; ! [00]    ; [04]   ; [08]   ; [0c]   ; [10]   ; [14] . . . . . [03fc] !
68 ; ! [400]   ; [404]  ; [408]  ; [40c]  ; [410]  ; [414] . . . . . [07fc] !
69 ; ! [800]   ; [804]  ; [808]  ; [80c]  ; [810]  ; [814] . . . . . [0bfc] !
70 ; ! [c00]   ; [c04]  ; [c08]  ; [c0c]  ; [c10]  ; [c14] . . . . . [0ffc] !
71 ; ![1000]   ;[1004]  ;[1008]  ;[100c]  ;[1010]  ;[1014] . . . . . [13fc] !
72 ; ![1400]   ;[1404]  ;[1408]  ;[140c]  ;[1410]  ;[1414] . . . . . [17fc] !
73 ; !    .    ;   .    ;   .    ;   .    ;   .    ;   .   . . . . .   .   !
74 ; !    .    ;   .    ;   .    ;   .    ;   .    ;   .   . . . . .   .   !
75 ; !    .    ;   .    ;   .    ;   .    ;   .    ;   .   . . . . .   .   !
76 ; !    .    ;   .    ;   .    ;   .    ;   .    ;   .   . . . . .   .   !
77 ; !    .    ;   .    ;   .    ;   .    ;   .    ;   .   . . . . .   .   !
78 ; !    .    ;   .    ;   .    ;   .    ;   .    ;   .   . . . . .   .   !
79 ; ![M+000]  ;[M+004] ;[M+008] ;[M+00c] ;[M+010] ;[M+014]. . . . . [M+3fc]!
80 ; !-----------------------------------------------------------------!
81 ; for M = n X 400
82
```

3D SOLDER PASTE VISION INSPECTION: A NOVEL APPROACH

BY

GEORGE T. AYOUB

IRI VISION
CARLSBAD, CALIFORNIA

APPENDIX D

3D SOLDER PASTE VISION INSPECTION: A NOVEL APPROACH

The advent of fine pitch devices ( 25 mils and smaller) has created new challenges in pcb manufacturing. Now more than ever before, the process parameters need to be controlled properly, otherwise the board yield and field reliability suffers greatly. In essence, the fine pitch technology increases significantly the number of pads per unit area making certain sections of the pcb very densily populated with an extremely small pad size and pad to pad distance. This means a tighter tolerance specifications which, when coupled with the prevalent increase in the number of components per board, generally results in a higher probability of defect per board. Therefore, in order to assure the same or higher quality demand with respect to regular 50 mils pitch surface mount, the probability of defect per pad/component must decrease substantially. This requires a focused effort, in tuning properly the process parameters, that must be applied at all phases of the manufacturing process. Failing that, the quality cost of the product becomes prohibitive.

A VARIETY OF PARAMETERS

One of the leading causes of defect is the paste application process. Small variations in the process parameters affect considerably the defect rate. The main parameters for the paste placement process are related to three main categories:

1) to the chemical material composition of the paste itself like solder powder surface oxidizing treatment, particle size, solvent content, viscosity and storage temperature.

2) to the screen printing machinery like a) squeegee type, blade hardness, angle of attack and pressure, snap-off-height, stroke length and speed, and b) stencil material type and manufacturing quality, opening size and thickness, stencil-to-circuit alignment and registration.

3) to the pc board itself like a) mask type and compatibility with the solder paste, and b) board warpage and stretch.

This variety of parameters need to be balanced carefully in order for the screen printing process to deliver the best results. This task necessitates the use of an inpection station, which is part of a process feedback loop, that measures the paste characteristics after placement. As seen below, the type, quality, quantity and timeliness of data are important to control the defect rate to an acceptable minimum.

TYPE AND QUALITY OF THE MEASUREMENTS

The most common type of defects for the paste process that need to be controlled effectively are: bridging, misregistration of the solder paste on the pad and insufficient or excess solder conditions. The defect characteristics are related to the volume and height of the paste, pad area coverage, x and y translation and shape of the paste. The volume and height of the paste are extremely important parameters that affects directly the soldaribility of the component. The volume measurement help to identify conditions of insufficient or excess solder. The height profile can help in determining abnormal conditions due to obstruction of the paste flow or insufficient pressure. The x and y translation are registration parameters that are directly related to the registration of the stencil with respect to the board. The pad area coverage measurement provides the ability to check to what degree the area of the paste covers the pad. This is useful to prevent cases of poor soldariblity because the paste covers a small percentage of the pad although the volume and translation are within norm. Finally, the shape of the paste blob can identify problems early on like slumping of the paste or "dog ears" that may lead to bridging or poor soldaribility. Therefore the shape of the paste is a quality parameter that can be used effectively to control the process and prevent problems from happening.

In order to detect pad to pad bridges, it is important that the measurement be taken not only on the pads or their proximities, but also in places where solder bridges are most likely to occur, like for example between two fine-pitch pads. Moreover, The measured parameters can be used alone or in combination to differentiate between critical situations and border line situations which are acceptable to the process. For example small solder paste bridges may typically be pulled towards the pad during reflow and therefore do not constitute a source of error for the process. On the other hand large bridges cause defects to happen in the soldering operation. The inspection system has to have the ability to differentiate therefore between small and large bridges.

Finally, the paste autoinspector has to go beyond the above steps and be more than a measurement and an inspection system: It has to be able to statistically analyse the data and look for patterns in the data and in the defect occurences. Only then, it will be able to detect conditions like uneven height of the paste from one end of the board to another end, which points to problems in the control of squeegee pressure and/or board warpage. Without using the statistical correlations and relating it to the process parameters, the full benefit of the paste autoinspector remains unrealized.

IN-LINE INSPECTION AND MEASUREMENT

The automated paste autoinspector plays a dual role as an inspection system and as a measurement system. As an inspection system, it identifies and reports the defects, thus contributing directly to an increase in the yield of the process. As a measurement system, it permits to maintain a high product quality level by relating the measurements to the process parameters and feeding back the information necessary to control the process. "Closing the loop" on the process assures that changes in the process are identified early on and that the process parameters are set at their optimum level. The result is higher yields and top quality products.

In order for the inspection system to be effective, it is necessary that the above measurements are done in real time. As the defect is passed along from one operation to another, the production loss increases exponentially. Even a sampling method of measurement is inadequate in many cases because of the costly production loss when one of the process parameters is upset generating a stream of consistent defects. Another reason why off-line sampling is inadequate is because of the nature of the screening process generating random defects that will go undetected with a program involving an off-line sampling technique. Therefore, in its role as an inspection system, the paste autoinspector is effective when it is applied in-line identifying the random defects at the earliest point when they are generated. This capability permits to minimize rework time and costs and is consistent with the "zero defect" philosophy adopted by many production managers. As a measurement system part of a feedback loop, the paste autoinspector is also more effective when used in-line permitting a timely control of the process parameters. This capability permits a consistent, stable and optimized settings of the process parameter values.

The in-line mode of operation for the paste inspection puts stringent requirements on the performance of the paste inspector. In effect, the false rejects rate for an in-line system need normally to be significantly smaller than for an off-line system. Keeping the false reject low while still maintaining a low false accept rate, requires repeatability and accuracy from the inspection system as well as enough intelligence to treat border line cases adequately. Normally, the volume measurement is specified to an accuracy of 10% while the repeatability is in the range of 1% to 2%. An error analysis would reveal that this is not a simple task and would require a careful choice of the sampling and resolution of the system.

THE MAGNITUDE OF THE IMAGE PROCESSING PROBLEM

Most paste inspection systems in the late eighties failed to meet the above requirements. The reason is that either they were not fully automated, or they lacked the speed to work in-line, or because their data quality in terms of measurement accuracy and statistical analysis was inadequate to effectively meet the production requirements for an SMT line. The advent of 3D laser triangulation systems went a long way to meet the above requirements, but however, still falls short on meeting the production speed when used in-line on a medium to high volume SMT production line. The 3D non-contact range sensor described in here is designed to fill this gap by working in-line and providing quality data supplemented by statistical analysis. To achieve this task many barriers in electro-optics, camera acquisition, image processing hardware and algorithm design had to be broken.

To get an idea of the magnitude of the problem lets take a concrete case of a system now being designed by IRI VISION for a high volume electronic manufacturer. The system basically consists of 8 cameras acquiring simultaneously eight images every 3 mils of displacement for a 5 inch lenght board. The inspection has to be completed in about 4 seconds. The data rate is therefore about 874 million pixels per second. Fortunately only about 20% of the pixels fall into interesting areas and therefore need to be processed. This reduces the useful data rate to about 175 million pixels per second which still presents a formidable computational task that dictates the use of parallel processing. In this case a total of 24 processors were used in parallel (including 16 RISK processors) to complete this task.

3D RANGE SENSOR: THEORY OF OPERATION

The 3D paste height, area, displacement and volume measurements are done by means of a non-contact range sensor based on a triangulation approach, using a laser-line beam and orthogonal camera sensors attached to an image processing computer. A focused laser line-beam, projected on the substrate at an angle of about 60 degrees from the vertical, scatters back light to the orthogonal camera sensor array. The illuminated line appearing in the image is then displaced in proportion to the height of the paste (see figure 1). The acquisition/processing proceeds as follows:

1) The substrate is presented to the sensor and the solid state laser diodes are pulsed to generate a laser-line beam. The camera acquires a 2D image of 512 pixels long in the horizontal direction and adjustable width in the vertical direction which is then stored in memory.

2) A processing algorithm finds the projected line contour and determines its position in the image coordinates by scanning every 512 positions in the vertical direction. As a result the contour position in the image coordinates is stored in a 512 line for further processing ( see figure 2).

3) The substrate, mounted on a micro-positioning stage, is moved a micro-step and step 1 and 2 are repeated until the whole substrate is scanned by this manner. The results stored in memory are referred to as the compressed height image.

4) After several paste blobs have been scanned by the laser-line a processing algorithm working on the compressed height image of each camera sensor measures the height, area, displacement and volume of the paste. The height is measured at each point by calculating the local displacement in sub-pixel accuracy with respect to a base line on the substrate. The area calculation is determined by finding the edges of the paste and counting the number of pixels internal to the edges. The paste displacement is calculated by c`omparing the mean position of the paste blob with respect to the database. The volume is then readily calculated by integrating the height times the area results obtained previously and taking into accounts the stage microsteps and field of view quantizations.

5) Step 4 is repeated for each camera and the results for the paste height, area, volume and displacement are aggregated for each blob and for the whole substrate and meaningful descriptive statistics are calculated.

CHARACTERISTICS OF THE APPROACH

1. High Intensity Pulsed Laser line:

The laser diodes, operating in the pulsed mode are able to achieve a higher degree of intensity level permitting an increase in the signal to noise ratio. Furthermore, the output intensity of the laser diodes are focused and summed up in order to achieve an even higher constant intensity laser line across the whole useful line width of the beam.

2. Variable Line Width Camera

The number of 512 lines acquired by the camera can be changed at will in order to accomodate the highest peak expected in the measured object. For example, with a 1 mil per pixel field of view, and 60 degrees from the vertical projected laser line beam, the width of the image field should be no less than 26 pixels in total when the highest peak is expected to be 15 mils, and no less than 17 pixels when the highest peak is expected to be 10 mils.

3. Variable Line Sampling Resolution

The distance between two consecutives lines determines the maximum possible spatial bandwith measurement along the direction of movement of the stage that can be achieved. The micro steps of the stage holding the substrate can be varied in order to achieve an optimum sampling rate in the direction of stage movement consistent with the highest spatial frequency of the paste surface and the processing speed available to the sensor. If the highest peak-valley distance of interest is denoted by D, then the sampling in the direction of the stage movement should be less than D/2, according to Shannon theorem, in order to avoid aliasing. When looking at the big features of a slow varying surface the sampling distance can be increased, and vise-versa when the paste surface is jittery, an accurate measurement is achieved by having a small sampling rate in the direction of movement. Note that the sampling rate along the line direction is determined by the optics (Field of View) and the resolution of the camera.

4. Gray Scale Processing of the Laser Line

Every single line in the 512 long image is processed in gray-scale and not binarized. This makes a big difference on obtaining accurate and repeatable results and permits to measure heights smaller in magnitude than the line width. It also permits to achieve robustness to noise and other artifacts due to shadowing.

The gray scale processing consist of calculating the center of gravity of the line position weighted by the image gray scale. In fact, the processing would work with any function of the gray scale that is convolved with the position (one dimensional convolution). However, the center of gravity weighting scheme was chosen because of its simplicity to calculate and its robustness to various kinds of noises.

5. Super Sampling

It is possible to achieve even higher resolution than the width of the laser line. This will be referred to as "Super-Sampling". This is not achievable with other triangulation methods that do not use gray scale processing for the height calculation. Super-Sampling is achievable because it is possible to deconvolve the processed measurements to yield the height for every micro step of the substrate movement. In effect, mathematically the image processing operation for each line corresponds to a convolution of the gray scale with the position. It is then possible to deconvolve several adjacent lines to yield the position of the height at each pixel position although the width of the laser line is bigger than one pixel.

6. Unbiased Measurements of the Height

When the laser line falls on corner where one part of the line is elevated with respect to the remaining part, the gray scale processing still yields an unbiased result of the height measurement, while traditional measurements not using gray scale yield a biased result for the height (see figure 3).

7. Robustness to Symmetric Noise

Scattering on some kind of substrates may yield symmetric noise that surrounds the laser line (see figure 4). The center of gravity calculation is immune to this kind of noise.

8. Robustness to Shadow Artifacts

Shadows normally occur because the laser is illuminating the substrate at an angle. Therefore any elevation on the substrate will shadow part of the substrate. When the shadow happens to be on a useful part of the substrate that need to be measured, it presents a problem that most of the triangulation techniques have difficulties to deal with. The gray scale processing using the center of gravity calculation for the height yields a best estimate of the height that is consistent with the illumination and object geometry (see figure 5).

9. Efficient Organisation of the Processing:

Processing the raw images from the laser is done in two steps: First an intermediate image which is the compressed height image is derived from the raw image. This compressed image serves then as input for the volume, area, average height and the paste displacement calculations. This division of work is a very efficient way for dealing with the huge amount of pixels that need to be processed and permits parallel processing on the two riskd and 68030 processors to take place within the MVP board.

VOLUME, AREA, HEIGHT AND PASTE DISPLACEMENT ALGO

Please refer to the flowchart in the following explanations.

B0: COMPRESSED HEIGHT IMAGE (INPUT):

The algorithm input is the compressed height image which is the result of the image processing done by the risk processors on the raw image (see theory of operation). In this image, the gray scale is proportional to the height. Note also that this image consists of two parts: "Sunset" and "Sunrise" which are related to the "Sunset" and "Sunrise" lasers.

B1: PROCESS "SUNSET" RESULTS SO AS TO BE CONSISTENT WITH "SUNRISE" RESULTS:

The "Sunset" results differ from the "Sunrise" results by the fact that their base lines do not coincide and height displacement increase run in opposite directions in the frame buffer (see figure). They need to be translated so as the base line coincides) and flipped in order that the height displacement be consistent with itself in both "Sunset" and "Sunrise" results.

B2: CAD DATABASE:

The CAD database of the pad location is resident in memory and is used as a reference for the paste and the substrate average height calculations.

B3: FIND BASE NEXT TO PASTE:

The information from the database is used to find a substrate base location where no paste is present. Starting from a large search area for the base around the pad, the abscence of paste is determined when the gray scale is relatively low and uniform in the area considered for the base substrate. Statistical techniques are used to test for uniformity of the height.

B4: ESTIMATE AVERAHE HEIGHT OF SUBSTRATE:

The substrate average height is calculated in the area where the substrate base has been determined.

1-57/2

What is claimed is:

1. A method of determining the geometric dimension of a minute particle disposed on the top surface of a substrate, comprising:

generating a plurality of coincident light beams arranged in a row;

directing said plurality of coincident light beams toward the substrate and the minute particle;

viewing said plurality of coincident light beams as they are reflected from the minute particle and the substrate;

determining the gray scale intensity levels of each of the beams reflecting from the minute particle and substrate;

determining a weighted average gray scale value of the plurality of reflected beams;

calculating the center of intensity of the beams reflecting from the minute particle and the substrate; and determining a weighted average dimension of the minute particle based on the calculated center of intensity.

2. A method according to claim 1, wherein the step of directing said plurality of coincident light beams includes the steps of:

directing a set of forward laser beams toward the surface of the substrate;

directing the set of forward laser beams rearwardly downwardly at an angle $\theta_{ss}$ relative to the horizontal plane of the substrate;

projecting a set of rear laser beams toward the surface of the substrate; and directing the set of rear laser beams forwardly downwardly at an angle $\theta_{SR}$ relative to the horizontal plane of the substrate.

3. A method according to claim 2, wherein $\theta_{SS}$ is between about 1 degree and about 89 degrees.

4. A method according to claim 3, wherein $\theta_{SS}$ is between about 15 degrees and about 75 degrees.

5. A method according to claim 4, wherein $\theta_{SS}$ is about 60 degrees.

6. A method according to claim 2, wherein $\theta_{SS}$ is between about 180 degrees and about 0 degrees.

7. A method of determining the geometric dimensions of a minute particle according to claim 1, wherein the step of viewing includes:

forming an image of said plurality of coincident light beams;

splitting the image of said beams into a pair of images;

reflecting said pair of images to form a group of image segments; and developing a pixel image voltage in response to viewing in a predetermined order each segment, wherein each voltage developed is indicative of the gray scale intensity level of the corresponding beam reflecting from the minute particles and substrate.

8. A method of determining the geometric dimension of a minute particle according to claim 1, wherein the step of determining a dimension of the minute particle includes determining the height of the minute particle.

9. A method of determining the geometric dimension of a minute particle according to claim 8, further comprising:

using camera means for viewing the plurality of coincident light beams reflecting from the substrate and the minute particle;

storing the determined height of the minute particle;

moving said camera means and the substrate relative to one another to permit the substrate to be scanned by said plurality of coincident light beams;

repeating the steps of generating, directing, viewing, determining, determining, determining, storing and moving until substantially the entire top surface of the substrate has been scanned by said plurality of coincident light beams;

retrieving the stored determined height information; and calculating the volume of the minute particle disposed on the top surface of the substrate.

10. A method according to claim 9, wherein the step of calculating the volume includes the step of:

calculating the area of the minute particle disposed on the top surface of the substrate.

11. A method according to claim 8, wherein the step of determining the height includes the step of determining the distance between the center of intensity of each beam reflecting from the minute particle and the center of intensity of each beam reflecting from the substrate.

12. A method according to claim 1, wherein the minute particle is an irregular shaped article.

13. A method according to claim 12, wherein the irregular shaped article is a paste blob having a given area.

14. A method according to claim 13, wherein the given area of the paste blob is calculated by averaging the gray scale values determined relative to a set of determined boundary values for the paste blob.

15. A method of determining the geometric dimensions of minute particles disposed on the top surface of a substrate, comprising:

using a plurality of cameras for observing elongated beams of reflected light;

mounting said plurality of cameras in groups of at least two cameras each, each group being spaced apart from every other group and being aligned parallel with every other group;

separating elongated beams of reflected light into a reflected beam and a transmitted beam, said transmitted beam being observed by the cameras in one of said groups;

deflecting said reflected beam to be received by another one of said groups and for preventing every other group from observing said reflected beam;

illuminating a given area of the substrate and the minute particles within said area with a forward laser beam and a rear laser beam;

viewing reflected forward laser beam images and reflected rear laser beam images by said cameras;

viewing orthogonally the reflected beam images as they are reflected from the minute particles and the substrate in said given area;

determining the gray scale intensity levels of the beam images reflecting from the minute particles and substrate in said given area;

determining the distance between the intensity center of the beam image reflecting from the minute particles and the intensity center of the beam image reflecting from the substrate;

determining the height of the minute particles within said given area;

storing the determined height of the minute particles within said given area;

moving said camera means and the substrate relative to one another to permit another area of the substrate to be scanned by said forward laser beam and said rear laser beam;

repeating the steps of illuminating, using, viewing, determining, determining, storing and moving until substantially the entire top surface of the substrate has been scanned by said forward and rear laser beams;

retrieving the stored determined height information;

calculating the area of each minute particle disposed on the top surface of the substrate; and calculating the volume of each minute particle disposed on the top surface of the substrate.

* * * * *